US006960581B2

(12) United States Patent
Betageri et al.

(10) Patent No.: US 6,960,581 B2
(45) Date of Patent: Nov. 1, 2005

(54) GLUCOCORTICOID MIMETICS, METHODS OF MAKING THEM, PHARMACEUTICAL FORMULATIONS, AND USES THEREOF

(75) Inventors: Rajashekhar Betageri, Bethel, CT (US); David S. Thomson, Ridgefield, CT (US); Yan Zhang, Hillsborough, NJ (US); Renee Michele Zindell, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/336,340

(22) Filed: Jan. 3, 2003

(65) Prior Publication Data

US 2003/0232823 A1 Dec. 18, 2003

Related U.S. Application Data

(60) Provisional application No. 60/348,486, filed on Jan. 14, 2002, and provisional application No. 60/379,078, filed on May 9, 2002.

(51) Int. Cl.$^7$ .................... C07D 265/02; C07D 307/83; A61K 31/536
(52) U.S. Cl. .................. 514/230.5; 544/63; 549/304; 564/162; 564/163; 564/167; 564/200
(58) Field of Search .......................................... 544/63

(56) References Cited

U.S. PATENT DOCUMENTS

| | | | |
|---|---|---|---|
| 4,880,839 | A | 11/1989 | Tucker |
| 5,039,691 | A | 8/1991 | Spagnuolo et al. |
| 6,323,199 | B1 | 11/2001 | Lehmann et al. |
| 6,329,534 | B1 | 12/2001 | Kym et al. |
| 6,380,223 | B1 | 4/2002 | Dow et al. |
| 6,436,986 | B1 | 8/2002 | Kym et al. |
| 6,506,766 | B1 | 1/2003 | Coghlan et al. |
| 6,583,180 | B2 | 6/2003 | Link et al. |
| 2002/0077356 | A1 | 6/2002 | Jaroch et al. |
| 2002/0156311 | A1 | 10/2002 | Link et al. |
| 2003/0232823 | A1 | 12/2003 | Betageri et al. |
| 2004/0010020 | A1 | 1/2004 | Kirrane, Jr. et al. |
| 2004/0010148 | A1 | 1/2004 | Kirrane, Jr. et al. |
| 2004/0023999 | A1 | 2/2004 | Bekkali et al. |
| 2004/0029932 | A1 | 2/2004 | Bekkali et al. |
| 2004/0097574 | A1 | 5/2004 | Marshall |

FOREIGN PATENT DOCUMENTS

| | | |
|---|---|---|
| BE | 900594 | 9/1984 |
| EP | 0 154 528 A2 | 3/1985 |
| EP | 0 154 528 A3 | 3/1985 |
| EP | 0 253 500 | 2/1991 |
| EP | 0 253 503 | 12/1991 |
| GB | 2 146 987 A | 9/1984 |
| WO | WO 96/19458 | 6/1996 |
| WO | WO 97/27852 | 8/1997 |
| WO | WO 98/54159 | * 12/1998 |
| WO | WO 99/41256 | 2/1999 |
| WO | WO 00/32584 | 6/2000 |
| WO | WO 00/66522 | 11/2000 |
| WO | WO 02/02565 | 1/2002 |
| WO | WO 02/10143 | 2/2002 |
| WO | WO 02064550 | 8/2002 |

OTHER PUBLICATIONS

Bekkali, Y., et al; Application entitled Glucocorticoid Mimetics, Methods of Making Them, Pharmaceutical Compositions and Uses Therof, accorded U.S. Appl. No. 10/639, 131.

Kuzmich, D., et al; Application entitled Glucocorticoid Mimetics, Methods of Making Them, Pharmaceutical Compositions and Uses Thereof, accords U.S. Appl. No. 10/739, 208.

Cywin, C. et al; Application entitled Glucocorticoid Mimetics, Methods of making Them, Pharmaceutical Compositions and Uses Thereof, accorded U.S. Appl. No. 10/785, 222.

Hamann, Lawrence, et al ; Discovery of a potent, Orally active, Nonsteroidal Androgen Receptor Agonist: 4–Ethyl–1,2,3,4–tetrahydro–6–(trifluoromathyl)–8–pyridono[5,6–g]–quinoline(LG121071), J. Med Chem, 1999, 42, 210–212.

Pooley, Charlotte, et al; Discovery and Preliminary SAR Studies of a Novel Nonsteroidal Progesterone Receptor Antagonist Pharmacophore, J. Med. Chem 1998, 41, 3461–3466.

Edwards, James, P. et al; 5–Aryl–1,2–dihydro–5H–chromeno[3,4–f]quinolines as Potent, Orally Active, Nonsteroidal Progestgerone Receptor Agonists; The Effect of D–Ring Substituents, J. Med. Chem 1998, 42, 303–310.

Zhi, Lin, et al; 5–Aryl–1,2–dihydro–5H–chromeno[3,4–f] quinolines; A Novel Class of Nonsteroidal Human Progesterone Receptor Agonists, J. Med. Chem 1998, 41, 291–302.

(Continued)

Primary Examiner—Richard L. Raymond
Assistant Examiner—Kahsay Habte
(74) Attorney, Agent, or Firm—Michael P. Morris; Timothy X. Witkowski; Thomas C. Blankinship

(57) ABSTRACT

A compound of Formula (I)

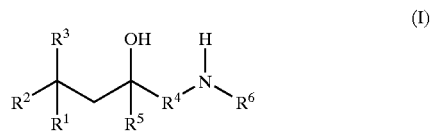

wherein $R^1$, $R^2$, $R^3$, $R^4$, $R^5$, and $R^6$ are as defined herein, or a tautomer, prodrug, solvate, or salt thereof, pharmaceutical compositions containing such compounds, and methods of modulating the glucocorticoid receptor function and methods of treating disease-states or conditions mediated by the glucocorticoid receptor function or characterized by inflammatory, allergic, or proliferative processes in a patient using these compounds.

12 Claims, No Drawings

OTHER PUBLICATIONS

Zhi, Lin; et al 5–Aryl–1,2,3,4–tetrahydrochromeno[3,4–f]quinolin–3–ones as a Novel Class Of Nonsteroidal Progesterone Receptor Agonists; Effect of A–Ring Modification, J. Med. Chem 1999, 42, 1466–1472.

Tegley, Christopher, et al; 5–Benzylidene 1,2–Dihydrochromeno[3,4–f]quinolines, A Novel Class Of Nonsteroidal Human Progesterone Receptor Agonists; J. Med. Chem 1998, 41, 4354–4359.

Edwards, James, P. et al; Preparation, Resolution and Biological Evaluation of 5–Aryl–1,2–dihydro–5H–chromeno[3,4–f]quinolines as Potent, Orally Active, Nonsteroidal Progesterone Receptor Agonists; J. Med. Chem. 1998, 41, 2779–2785.

Hamann, Lawrence, et al; Synthesis and Biological Activity of a Novel Series of Nonsteroidal, Peripherally Selective androgen Receptor Antagonist Derived from 1,2–Dihydropyridono[5–6–g] quinolines J. Med. Chem 1998, 41, 623–639.

English Translation of WO/02/10143.

* cited by examiner

GLUCOCORTICOID MIMETICS, METHODS OF MAKING THEM, PHARMACEUTICAL FORMULATIONS, AND USES THEREOF

RELATED APPLICATIONS

This application claims benefit under 35 U.S.C. § 119(e) of prior provisional applications U.S. Ser. No. 60/379,078, filed May 9, 2002, and U.S. Ser. No. 60/348,486, filed Jan. 14, 2002. Both of these provisional applications are hereby incorporated by reference herein in their entireties.

FIELD OF THE INVENTION

The present invention relates to glucocorticoid mimetics or ligands, methods of making such compounds, their use in pharmaceutical compositions, and their use in modulating the glucocorticoid receptor function, treating disease-states or conditions mediated by the glucocorticoid receptor function in a patient in need of such treatment, and other uses.

BACKGROUND OF THE INVENTION

Glucocorticoids, a class of corticosteroids, are endogenous hormones with profound effects on the immune system and multiple organ systems. They suppress a variety of immune and inflammatory functions by inhibition of inflammatory cytokines such as IL-1, IL-2, IL-6, and TNF, inhibition of arachidonic acid metabolites including prostaglandins and leukotrienes, depletion of T-lymphocytes, and reduction of the expression of adhesion molecules on endothelial cells (P. J. Barnes, Clin. Sci., 1998, 94, pp. 557–572; P. J. Barnes et al., Trends Pharmacol. Sci., 1993, 14, pp. 436–441). In addition to these effects, glucocorticoids stimulate glucose production in the liver and catabolism of proteins, play a role in electrolyte and water balance, reduce calcium absorption, and inhibit osteoblast function.

The anti-inflammatory and immune suppressive activities of endogenous glucocorticoids have stimulated the development of synthetic glucocorticoid derivatives including dexamethasone, prednisone, and prednisolone (L. Parente, *Glucocorticoids*, N. J. Goulding and R. J. Flowers (eds.), Boston: Birkhauser, 2001, pp. 35–54). These have found wide use in the treatment of inflammatory, immune, and allergic disorders including rheumatic diseases such as rheumatoid arthritis, juvenile arthritis, and ankylosing spondylitis, dermatological diseases including psoriasis and pemphigus, allergic disorders including allergic rhinitis, atopic dermatitis, and contact dermatitis, pulmonary conditions including asthma and chronic obstructive pulmonary disease (COPD), and other immune and inflammatory diseases including Crohn disease, ulcerative colitis, systemic lupus erythematosus, autoimmune chronic active hepatitis, osteoarthritis, tendonitis, and bursitis (J. Toogood, *Glucocorticoids*, N. J. Goulding and R. J. Flowers (eds.), Boston: Birkhauser, 2001, pp. 161–174). They have also been used to help prevent rejection in organ transplantation.

Unfortunately, in addition to the desired therapeutic effects of glucocorticoids, their use is associated with a number of adverse side effects, some of which can be severe and life-threatening. These include alterations in fluid and electrolyte balance, edema, weight gain, hypertension, muscle weakness, development or aggravation of diabetes mellitus, and osteoporosis. Therefore, a compound that exhibited a reduced side effect profile while maintaining the potent anti-inflammatory effects would be particularly desirable, especially when treating a chronic disease.

The effects of glucocorticoids are mediated at the cellular level by the glucocorticoid receptor (R. H. Oakley and J. Cidlowski, *Glucocorticoids*, N. J. Goulding and R. J. Flowers (eds.), Boston: Birkhauser, 2001, pp. 55–80). The glucocorticoid receptor is a member of a class of structurally related intracellular receptors that when coupled with a ligand can function as a transcription factor that affects gene expression (R. M. Evans, Science, 1988, 240, pp. 889–895). Other members of the family of steroid receptors include the mineralocorticoid, progesterone, estrogen, and androgen receptors. In addition to the effects mentioned above for glucocorticoids, hormones that act on this receptor family have a profound influence on body homeostasis, mineral metabolism, the stress response, and development of sexual characteristics. *Glucocorticoids*, N. J. Goulding and R. J. Flowers (eds.), Boston: Birkhauser, 2001, is hereby incorporated by reference in its entirety to better describe the state of the art.

A molecular mechanism which accounts for the beneficial anti-inflammatory effects and the undesired side effects has been proposed (e.g., S. Heck et al., EMBO J., 1994, 17, pp. 4087–4095; H. M. Reichardt et al., Cell, 1998, 93, pp. 531–541; F. Tronche et al., Curr. Opin. in Genetics and Dev., 1998, 8, pp. 532–538). Many of the metabolic and cardiovascular side effects are thought to be the result of a process called transactivation. In transactivation, the translocation of the ligand-bound glucocorticoid receptor to the nucleus is followed by binding to glucocorticoid response elements (GREs) in the promoter region of side effect-associated genes, for example, phosphoenolpyruvate carboxy kinase (PEPCK) in the case of increased glucose production. The result is an increased transcription rate of these genes which is believed to result, ultimately, in the observed side effects. The anti-inflammatory effects are thought to be due to a process called transrepression. In general, transrepression is a process independent of DNA binding that results from inhibition of NF-kB and AP-1-mediated pathways, leading to down regulation of many inflammatory and immune mediators. Additionally, it is believed that a number of the observed side effects may be due to the cross-reactivity of the currently available glucocorticoids with other steroid receptors, particularly the mineralocorticoid and progesterone receptors.

Thus, it may be possible to discover ligands for the glucocorticoid receptor that are highly selective and, upon binding, can dissociate the transactivation and transrepression pathways, providing therapeutic agents with a reduced side effect profile. Assay systems to determine effects on transactivation and transrepression have been described (e.g., C. M. Bamberger and H. M. Schulte, Eur. J. Clin. Invest., 2000, 30 (suppl. 3), pp. 6–9). Selectivity for the glucocorticoid receptor may be determined by comparing the binding affinity for this receptor with that of other steroid family receptors including those mentioned above.

Glucocorticoids also stimulate the production of glucose in the liver by a process called gluconeogenesis and it is believed that this process is mediated by transactivation events. Increased glucose production can exacerbate type II diabetes, therefore a compound that selectivity inhibited glucocorticoid mediated glucose production may have therapeutic utility in this indication (J. E. Freidman et al., J. Biol. Chem., 1997, 272, pp. 31475–31481).

Novel ligands for the glucocorticoid receptor have been described in the scientific and patent literature. For example, PCT International Publication No. WO 99/33786 discloses triphenylpropanamide compounds with potential use in treating inflammatory diseases. PCT International Publication No. WO 00/66522 describes non-steroidal compounds as selective modulators of the glucocorticoid receptor potentially useful in treating metabolic and inflammatory diseases. PCT International Publication No. WO 99/41256 describes tetracyclic modulators of the glucocorticoid receptor potentially useful in treating immune, autoimmune, and inflammatory diseases. U.S. Pat. No. 5,688,810 describes various non-steroidal compounds as modulators of glucocorticoid and other steroid receptors. PCT International Publication No. WO 99/63976 describes a non-steroidal, liver-selective glucocorticoid antagonist potentially useful in the treatment of diabetes. PCT International Publication No. WO 00/32584 discloses non-steroidal compounds having anti-inflammatory activity with dissociation between anti-inflammatory and metabolic effects. PCT International Publication No. WO 98/54159 describes non-steroidal cyclically substituted acylanilides with mixed gestagen and androgen activity. U.S. Pat. No. 4,880,839 describes acylanilides having progestational activity and EP 253503 discloses acylanilides with antiandrogenic activity. PCT International Publication No. WO 97/27852 describes amides that are inhibitors of farnesyl-protein transferase.

A compound that is found to interact with the glucocorticoid receptor in a binding assay could be an agonist or an antagonist. The agonist properties of the compound could be evaluated in the transactivation or transrepression assays described above. Given the efficacy demonstrated by available glucocorticoid drugs in inflammatory and immune diseases and their adverse side effects, there remains a need for novel glucocorticoid receptor agonists with selectivity over other members of the steroid receptor family and a dissociation of the transactivation and transrepression activities. Alternatively, the compound may be found to have antagonist activity. As mentioned above, glucocorticoids stimulate glucose production in the liver. Increased glucose production induced by glucocorticoid excess can exacerbate existing diabetes, or trigger latent diabetes. Thus a ligand for the glucocorticoid receptor that is found to be an antagonist may be useful, inter alia, for treating or preventing diabetes.

SUMMARY OF THE INVENTION

The instant invention is directed to compounds of Formula (I)

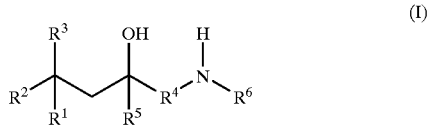

(I)

wherein:
$R^1$ is an aryl or heteroaryl group, each optionally independently substituted with one to three substituent groups,
  wherein each substituent group of $R^1$ is independently $C_1$–$C_5$ alkyl, $C_2$–$C_5$ alkenyl, $C_2$–$C_5$ alkynyl, $C_3$–$C_8$ cycloalkyl, aryl, $C_1$–$C_5$ alkoxy, aryloxy, $C_1$–$C_5$ alkanoyl, aroyl, $C_1$–$C_5$ alkoxycarbonyl, $C_1$–$C_5$ alkanoyloxy, aminocarbonyloxy, $C_1$–$C_5$ alkylaminocarbonyloxy, $C_1$–$C_5$ dialkylaminocarbonyloxy, aminocarbonyl, $C_1$–$C_5$ alkylaminocarbonyl, $C_1$–$C_5$ dialkylaminocarbonyl, $C_1$–$C_5$ alkanoylamino, $C_1$–$C_5$ alkoxycarbonylamino, $C_1$–$C_5$ alkylsulfonylamino, $C_1$–$C_5$ alkylaminosulfonyl, $C_1$–$C_5$ dialkylaminosulfonyl, halogen, hydroxy, carboxy, cyano, trifluoromethyl, nitro, amino wherein the nitrogen atom is optionally independently mono- or di-substituted by $C_1$–$C_5$ alkyl or aryl; or ureido wherein either nitrogen atom is optionally independently substituted with $C_1$–$C_5$ alkyl; or $C_1$–$C_5$ alkylthio wherein the sulfur atom is optionally oxidized to a sulfoxide or sulfone,
  wherein each substituent group of $R^1$ is optionally independently substituted with one to three substituent groups selected from methyl, halogen, hydroxy, oxo, cyano, trifluoromethyl, and amino;
$R^2$ and $R^3$ are each independently hydrogen or $C_1$–$C_5$ alkyl, or $R^2$ and $R^3$ together with the carbon atom they are commonly attached to form a $C_3$–$C_8$ spiro cycloalkyl ring;
$R^4$ is $CH_2$ or $C$=$O$;
$R^5$ is carbocycle, heterocyclyl, aryl, heteroaryl, carbocycle-$C_1$–$C_8$ alkyl, aryl-$C_1$–$C_8$ alkyl, aryl-$C_1$–$C_8$ haloalkyl, heterocyclyl-$C_1$–$C_8$ alkyl, heteroaryl-$C_1$–$C_8$ alkyl, carbocycle-$C_2$–$C_8$ alkenyl, aryl-$C_2$–$C_8$ alkenyl, heterocyclyl-$C_2$–$C_8$ alkenyl, or heteroaryl-$C_2$–$C_8$ alkenyl, each optionally independently substituted with one to three substituent groups,
  wherein each substituent group of $R^5$ is independently $C_1$–$C_5$ alkyl, $C_2$–$C_5$ alkenyl, $C_2$–$C_5$ alkynyl, $C_3$–$C_8$ cycloalkyl, phenyl, $C_1$–$C_5$ alkoxy, phenoxy, $C_1$–$C_5$ alkanoyl, aroyl, $C_1$–$C_5$ alkoxycarbonyl, $C_1$–$C_5$ alkanoyloxy, aminocarbonyloxy, $C_1$–$C_5$ alkylaminocarbonyloxy, $C_1$–$C_5$ dialkylaminocarbonyloxy, aminocarbonyl, $C_1$–$C_5$ alkylaminocarbonyl, $C_1$–$C_5$ dialkylaminocarbonyl, $C_1$–$C_5$ alkanoylamino, $C_1$–$C_5$ alkoxycarbonylamino, $C_1$–$C_5$ alkylsulfonylamino, $C_1$–$C_5$ alkylaminosulfonyl, $C_1$–$C_5$ dialkylaminosulfonyl, halogen, hydroxy, carboxy, cyano, trifluoromethyl, nitro, amino wherein the nitrogen atom is optionally independently mono- or di-substituted by $C_1$–$C_5$ alkyl; or ureido wherein either nitrogen atom is optionally independently substituted with $C_1$–$C_5$ alkyl; or $C_1$–$C_5$ alkylthio wherein the sulfur atom is optionally oxidized to a sulfoxide or sulfone; and
$R^6$ is an aryl group optionally independently substituted with one to three substituent groups or is group A or group B:

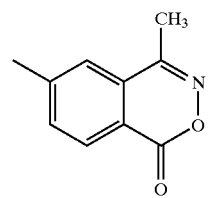

A

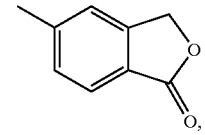

B wherein each substituent group of $R^6$ is independently $C_1$–$C_5$ alkyl, $C_2$–$C_5$ alkenyl, $C_2$–$C_5$ alkynyl, $C_3$–$C_8$ cycloalkyl, $C_1$–$C_5$ alkoxy, $C_1$–$C_5$ alkanoyl, $C_1$–$C_5$ alkoxycarbonyl, $C_1$–$C_5$ alkanoyloxy, aminocarbonyloxy, $C_1$–$C_5$ alkylaminocarbonyloxy, $C_1$–$C_5$ dialkylaminocarbonyloxy, aminocarbonyl, $C_1$–$C_5$ alkylaminocarbonyl, $C_1$–$C_5$ dialkylaminocarbonyl, $C_1$–$C_5$ alkanoylamino, $C_1$–$C_5$ alkoxycarbonylamino, $C_1$–$C_5$ alkylsulfonylamino, $C_1$–$C_5$ alkylaminosulfonyl, $C_1$–$C_5$ dialkylaminosulfonyl, halogen, hydroxy, carboxy, cyano, trifluoromethyl, nitro, amino wherein the nitrogen atom is optionally independently mono- or di-substituted by $C_1$–$C_5$ alkyl; or ureido wherein either nitrogen atom is optionally independently substituted with $C_1$–$C_5$ alkyl; or $C_1$–$C_5$ alkylthio wherein the sulfur atom is optionally oxidized to a sulfoxide or sulfone,
or a tautomer, prodrug, solvate, or salt thereof.

Another aspect of the invention includes compounds of Formula (I), wherein:

$R^1$ is phenyl, naphthyl, indanyl, indenyl, chromanyl, dihydrobenzofuranyl, dihydroindolyl, dihydroquinolinyl, dihydroisoquinolinyl, tetrahydroquinolinyl, tetrahydroisoquinolinyl, thienyl, furanyl, pyrrolyl, pyridinyl, pyrimidinyl, pyrazinyl, indolyl, benzofuranyl, or benzothienyl, each optionally independently substituted with one to three substituent groups, wherein each substituent group of $R^1$ is independently $C_1$–$C_3$ alkyl, $C_2$–$C_3$ alkenyl, $C_2$–$C_3$ alkynyl, $C_1$–$C_3$ alkoxy, $C_1$–$C_3$ alkanoyl, $C_1$–$C_3$ alkanoylamino, halogen, hydroxy, cyano, trifluoromethyl, amino wherein the nitrogen atom is optionally independently mono- or di-substituted by $C_1$–$C_3$ alkyl; or $C_1$–$C_3$ alkylthio wherein the sulfur atom is optionally oxidized to a sulfoxide or sulfone, wherein each substituent group of $R^1$ is optionally independently substituted with one to three substituent groups selected from methyl, fluoro, chloro, bromo, hydroxy, oxo, cyano, trifluoromethyl, and amino;

$R^2$ and $R^3$ are each independently $C_1$–$C_3$ alkyl, or $R^2$ and $R^3$ together with the carbon atom they are commonly attached to form a $C_3$–$C_6$ spiro cycloalkyl ring;

$R^4$ is $CH_2$ or C=O;

$R^5$ is cyclopropyl, cyclobutyl, cyclopentyl, cyclohexyl, cyclopentylmethyl, cyclohexylmethyl, benzyl, cyclopentylethyl, cyclohexylethyl, phenethyl, or phenyldifluoromethyl, each optionally independently substituted with one to three substituent groups, wherein each substituent group of $R^5$ is independently methyl, methoxy, hydroxy, halogen, cyano, or trifluoromethyl; and $R^6$ is a phenyl group optionally independently substituted with one to three substituent groups or is group A or group B:

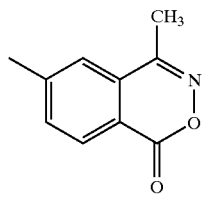

A

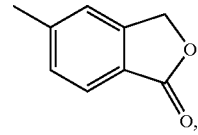

B wherein each substituent group of $R^6$ is independently methyl, methoxy, halogen, cyano, or trifluoromethyl, or a tautomer, prodrug, solvate, or salt thereof.

Yet another aspect of the invention includes compounds of Formula (I) as set forth above, wherein $R^6$ is an aryl group optionally substituted with one to three substituent groups and wherein each substituent group of $R^6$ is independently: $C_1$–$C_5$ alkyl, $C_2$–$C_5$ alkenyl, $C_2$–$C_5$ alkynyl, $C_3$–$C_8$ cycloalkyl, $C_1$–$C_5$ alkoxy, $C_1$–$C_5$ alkanoyl, $C_1$–$C_5$ alkoxycarbonyl, $C_1$–$C_5$ alkanoyloxy, $C_1$–$C_5$ alkylaminocarbonyloxy, $C_1$–$C_5$ dialkylaminocarbonyloxy, $C_1$–$C_5$ alkylaminocarbonyl, $C_1$–$C_5$ dialkylaminocarbonyl, $C_1$–$C_5$ alkanoylamino, $C_1$–$C_5$ alkoxycarbonylamino, $C_1$–$C_5$ alkylsulfonylamino, $C_1$–$C_5$ alkylaminosulfonyl, $C_1$–$C_5$ dialkylaminosulfonyl, halogen, hydroxy, carboxy, cyano, trifluoromethyl, nitro, amino wherein the nitrogen atom is optionally independently mono- or di-substituted by $C_1$–$C_5$ alkyl; or ureido wherein either nitrogen atom is optionally independently substituted with $C_1$–$C_5$ alkyl; or $C_1$–$C_5$ alkylthio wherein the sulfur atom is optionally oxidized to a sulfoxide or sulfone.

The following are representative compounds according to the invention:

| Compound Name | Compound Structure |
| --- | --- |
| 2-Benzyl-2-hydroxy-4-methyl-4-phenylpentanoic acid(1-oxo-1,3-dihydroisobenzofuran-5-yl)amide | 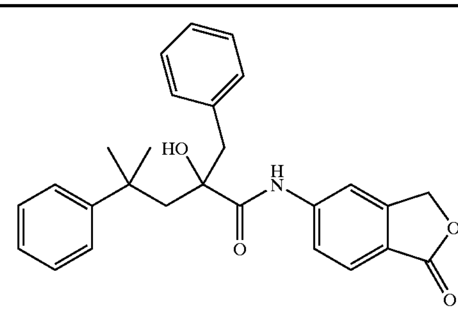 |
| 2-Hydroxy-4-methyl-2,4-diphenylpentanoic acid(1-oxo-1,3-dihydroisobenzofuran-5-yl)amide | 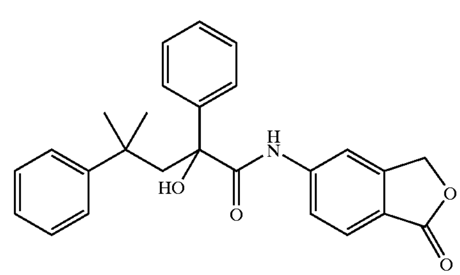 |

-continued

| Compound Name | Compound Structure |
|---|---|
| 2-Hydroxy-4-methyl-2-phenethyl-4-phenylpentanoic acid(1-oxo-1,3-dihydroisobenzofuran-5-yl)amide | 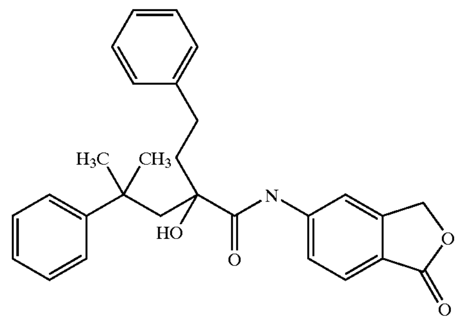 |
| 2-Hydroxy-2-(3-methoxybenzyl)-4-methyl-4-phenylpentanoic acid(1-oxo-1,3-dihydroisobenzofuran-5-yl)amide | 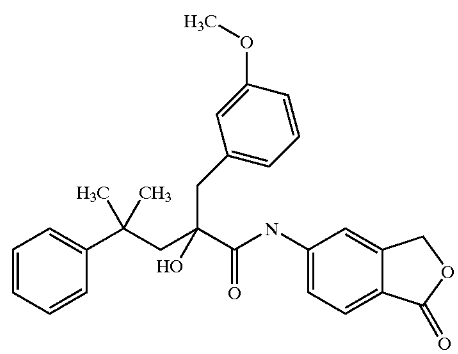 |
| 2-Hydroxy-2-(4-methoxybenzyl)-4-methyl-4-phenylpentanoic acid(1-oxo-1,3-dihydroisobenzofuran-5-yl)amide | 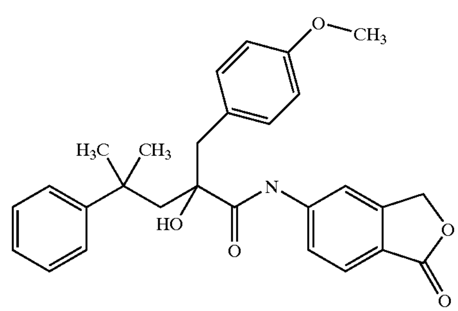 |
| 2-Hydroxy-2-[2-(4-methoxyphenyl)ethyl]-4-methyl-4-phenylpentanoic acid(1-oxo-1,3-dihydroisobenzofuran-5-yl)amide | 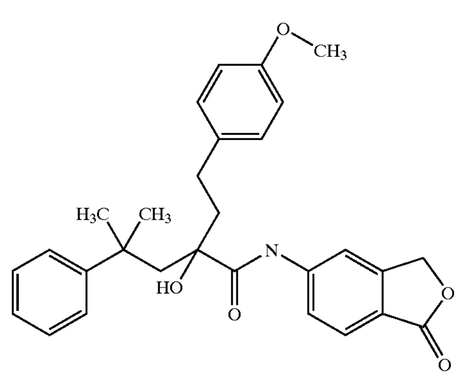 |

-continued

| Compound Name | Compound Structure |
|---|---|
| 2-Cyclohexylmethyl-2-hydroxy-4-methyl-4-phenylpentanoic acid(1-oxo-1,3-dihydroisobenzofuran-5-yl)amide | 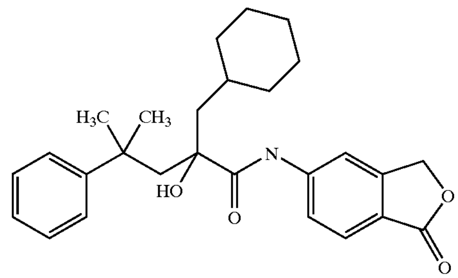 |
| 2-(4-tert-Butylbenzyl)-2-hydroxy-4-methyl-4-phenylpentanoic acid(1-oxo-1,3-dihydroisobenzofuran-5-yl)amide | 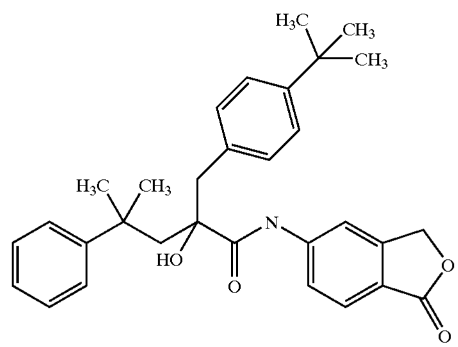 |
| 2-Biphenyl-4-ylmethyl-2-hydroxy-4-methyl-4-phenylpentanoic acid(1-oxo-1,3-dihydroisobenzofuran-5-yl)amide | 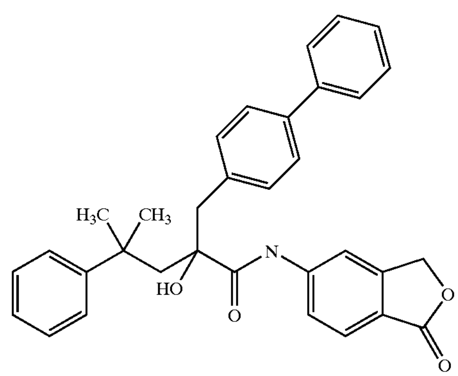 |
| 2-Hydroxy-4-methyl-2-naphthalen-2-ylmethyl-4-phenylpentanoic acid(1-oxo-1,3-dihydroisobenzofuran-5-yl)amide | 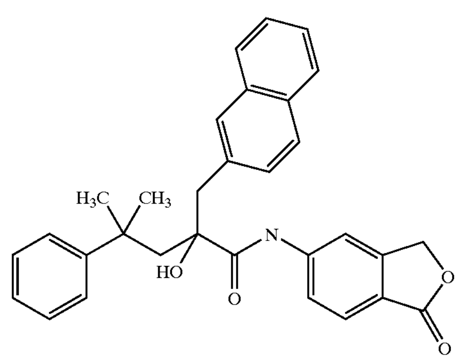 |

-continued

| Compound Name | Compound Structure |
|---|---|
| 2-Hydroxy-2-(3-hydroxybenzyl)-4-methyl-4-phenylpentanoic acid(1-oxo-1,3-dihydroisobenzofuran-5-yl)amide | 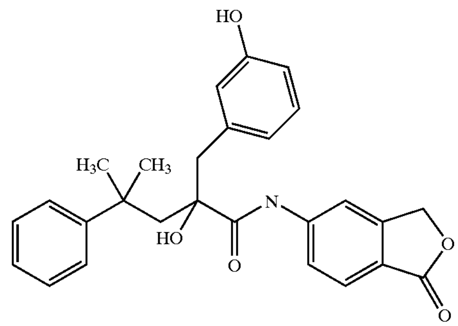 |
| 2-Hydroxy-4-methyl-2-(2-methyl-2-phenylpropyl)-4-phenylpentanoic acid(1-oxo-1,3-dihydroisobenzofuran-5-yl)amide | 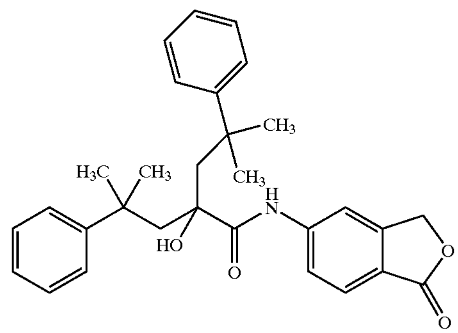 |
| 2-Benzyl-4-(5-fluoro-2-methoxyphenyl)-2-hydroxy-4-methylpentanoic acid(1-oxo-1,3-dihydroisobenzofuran-5-yl)amide | 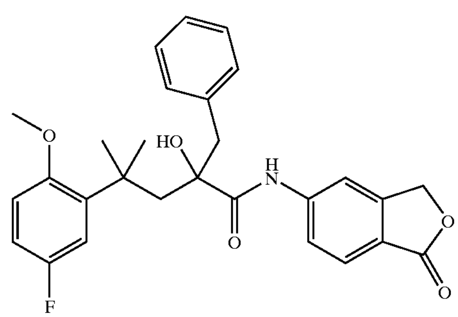 |
| 2-Cyclohexylmethyl-4-(5-fluoro-2-methoxyphenyl)-2-hydroxy-4-methylpentanoic acid(1-oxo-1,3-dihydroisobenzofuran-5-yl)amide | 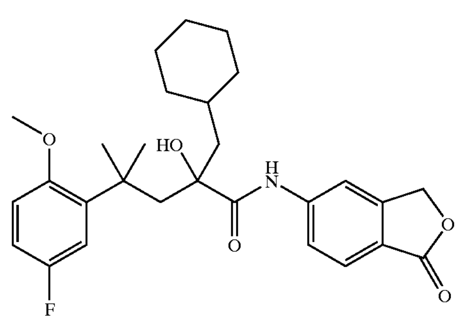 |

-continued

| Compound Name | Compound Structure |
|---|---|
| 2-Benzyl-4-(5-fluoro-2-hydroxyphenyl)-2-hydroxy-4-methylpentanoic acid (1-oxo-1,3-dihydroisobenzofuran-5-yl)amide | 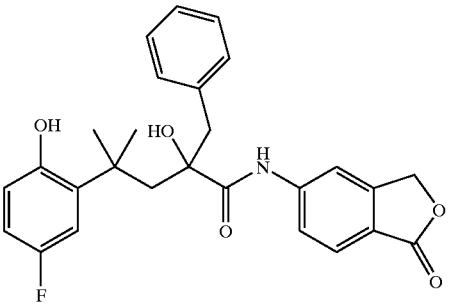 |
| 2-Cyclohexylmethyl-4-(5-fluoro-2-hydroxyphenyl)-2-hydroxy-4-methylpentanoic acid(1-oxo-1,3-dihydroisobenzofuran-5-yl)amide | 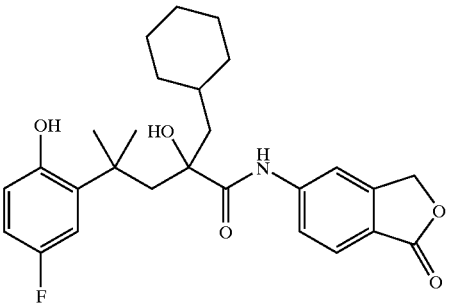 |
| 4-(5-Fluoro-2-hydroxyphenyl)-2-hydroxy-4-methyl-2-(2-methyl-2-phenylpropyl)pentanoic acid(1-oxo-1,3-dihydroisobenzofuran-5-yl)amide | 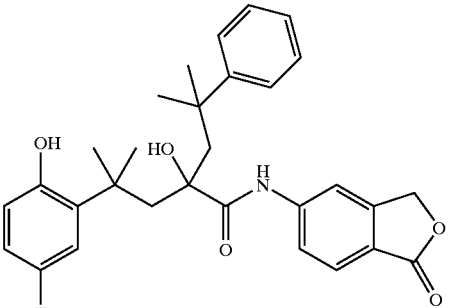 |
| 2-(2-Chloro-6-fluorobenzyl)-4-(5-fluoro-2-methoxyphenyl)-2-hydroxy-4-methylpentanoic acid(1-oxo-1,3-dihydroisobenzofuran-5-yl)amide | 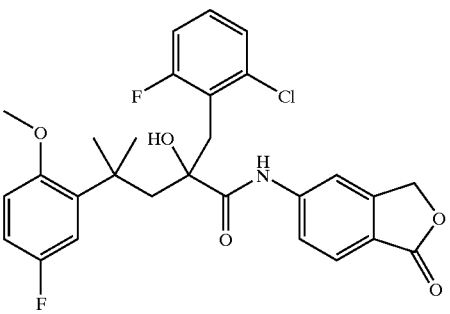 |

-continued

| Compound Name | Compound Structure |
|---|---|
| 2-(3-Fluorobenzyl)-4-(5-fluoro-2-methoxyphenyl)-2-hydroxy-4-methylpentanoic acid(1-oxo-1,3-dihydroisobenzofuran-5-yl)amide | 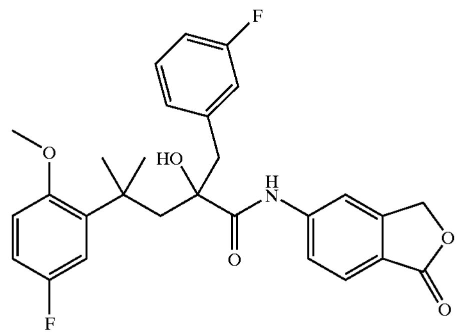 |
| 2-(2-Fluorobenzyl)-4-(5-fluoro-2-methoxyphenyl)-2-hydroxy-4-methylpentanoic acid(1-oxo-1,3-dihydroisobenzofuran-5-yl)amide | 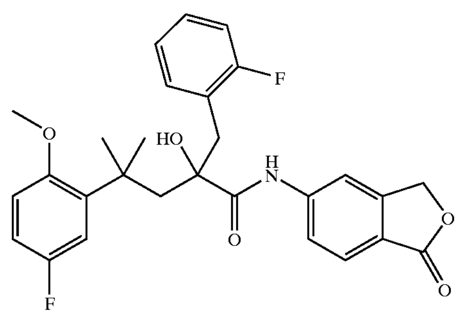 |
| 2-(3,4-Difluorobenzyl)-4-(5-fluoro-2-methoxyphenyl)-2-hydroxy-4-methylpentanoic acid(1-oxo-1,3-dihydroisobenzofuran-5-yl)amide | 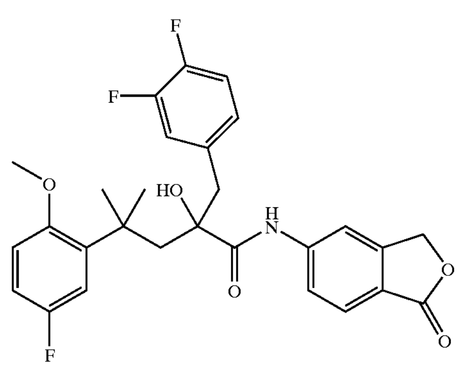 |
| 2-(2-Chloro-6-fluorobenzyl)-4-(5-fluoro-2-hydroxyphenyl)-2-hydroxy-4-methylpentanoic acid(1-oxo-1,3-dihydroisobenzofuran-5-yl)amide | 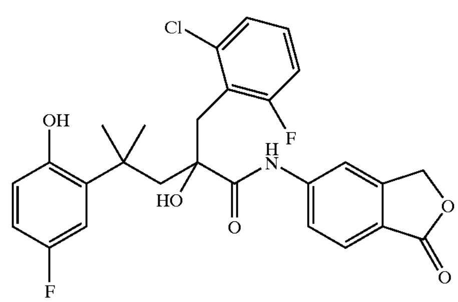 |

-continued

| Compound Name | Compound Structure |
|---|---|
| 2-(3-Fluorobenzyl)-4-(5-fluoro-2-hydroxyphenyl)-2-hydroxy-4-methylpentanoic acid(1-oxo-1,3-dihydroisobenzofuran-5-yl)amide | 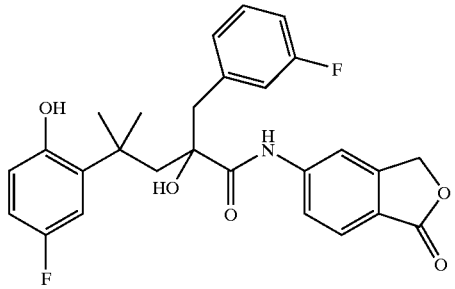 |
| 2-(2-Fluorobenzyl)-4-(5-fluoro-2-hydroxyphenyl)-2-hydroxy-4-methylpentanoic acid(1-oxo-1,3-dihydroisobenzofuran-5-yl)amide | 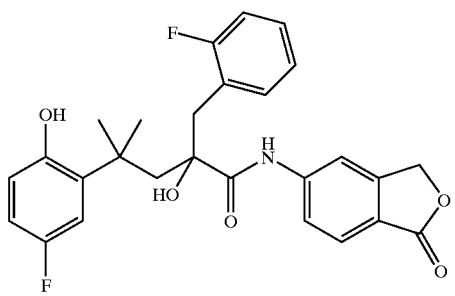 |
| 2-(3,4-Difluorobenzyl)-4-(5-fluoro-2-hydroxyphenyl)-2-hydroxy-4-methylpentanoic acid(1-oxo-1,3-dihydroisobenzofuran-5-yl)amide | 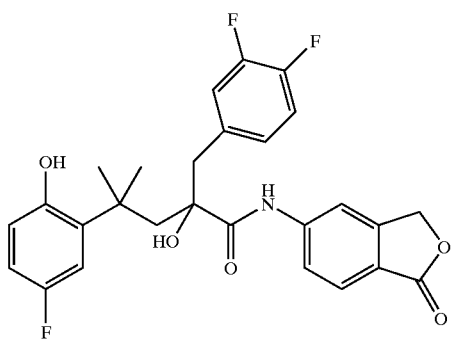 |
| 2-(4-Fluorobenzyl)-4-(5-fluoro-2-methoxyphenyl)-2-hydroxy-4-methylpentanoic acid(1-oxo-1,3-dihydroisobenzofuran-5-yl)amide | 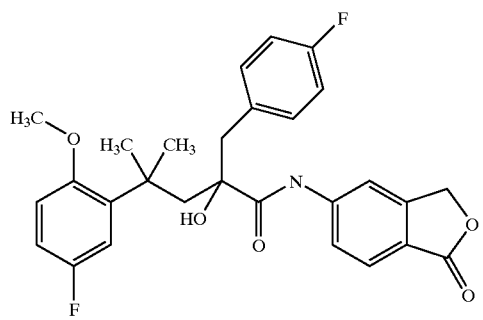 |

-continued

| Compound Name | Compound Structure |
|---|---|
| 4-(5-Fluoro-2-methoxyphenyl)-2-hydroxy-4-methyl-2-(3-methylbenzyl)pentanoic acid(1-oxo-1,3-dihydroisobenzofuran-5-yl)amide | 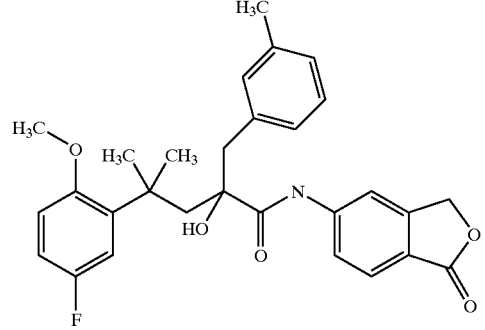 |
| 2-(4-Fluorobenzyl)-4-(5-fluoro-2-hydroxyphenyl)-2-hydroxy-4-methylpentanoic acid(1-oxo-1,3-dihydroisobenzofuran-5-yl)amide | 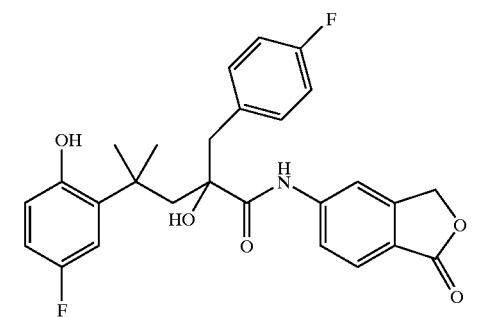 |
| 4-(5-Fluoro-2-hydroxyphenyl)-2-hydroxy-4-methyl-2-(3-methylbenzyl)pentanoic acid(1-oxo-1,3-dihydroisobenzofuran-5-yl)amide | 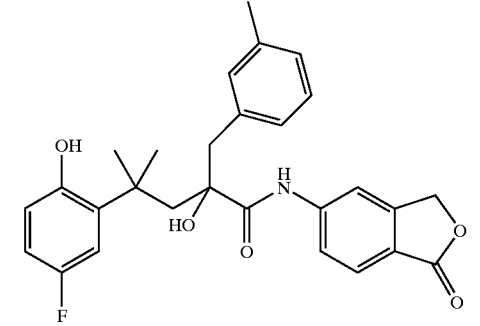 |
| 2-(3,5-Difluorophenyl)-4-(5-fluoro-2-hydroxyphenyl)-2-hydroxy-4-methylpentanoic acid(1-oxo-1,3-dihydroisobenzofuran-5-yl)amide | 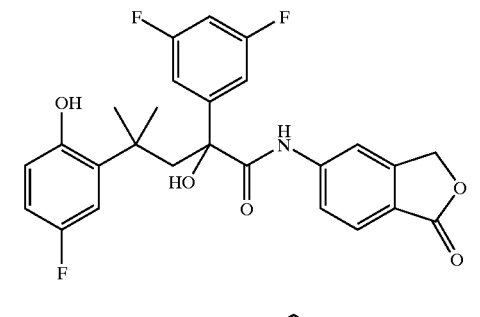 |
| 2-Benzyl-4-(5-fluoro-2-methoxyphenyl)-2-hydroxy-4-methylpentanoic acid(4-methyl-1-oxo-1H-benzo[d][1,2]oxazin-6-yl)amide | 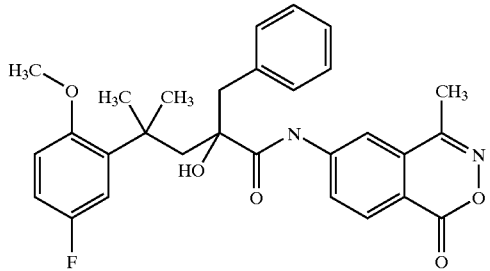 |

-continued

| Compound Name | Compound Structure |
| --- | --- |
| 2-Benzyl-4-(5-fluoro-2-hydroxyphenyl)-2-hydroxy-4-methylpentanoic acid(4-methyl-1-oxo-1H-benzo[d][1,2]oxazin-6-yl)amide | 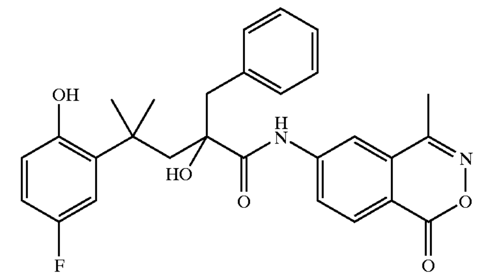 |
| 2-Cyclohexylmethyl-4-(5-fluoro-2-methoxyphenyl)-2-hydroxy-4-methylpentanoic acid(4-methyl-1-oxo-1H-benzo[d][1,2]oxazin-6-yl)amide | 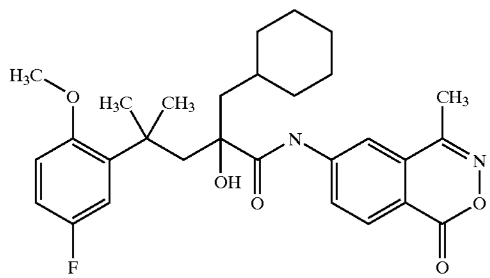 |
| 2-Benzyl-4-(5-fluoro-2-methoxyphenyl)-2-hydroxy-4-methylpentanoic acid(3,5-dichlorophenyl)amide | 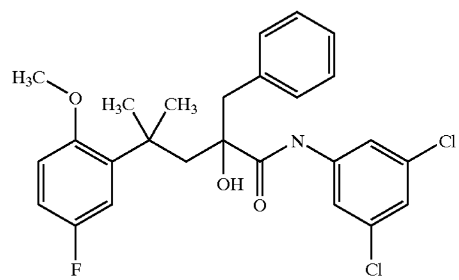 |
| 4-(5-Fluoro-2-methoxyphenyl)-2-hydroxy-4-methyl-2-(2-methylbenzyl)pentanoic acid(1-oxo-1,3-dihydroisobenzofuran-5-yl)amide | 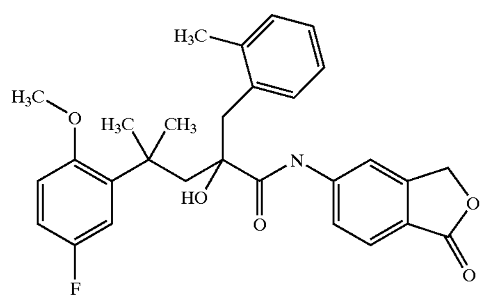 |
| 2-(3,5-Dimethylbenzyl)-4-(5-fluoro-2-methoxyphenyl)-2-hydroxy-4-methylpentanoic acid(1-oxo-1,3-dihydroisobenzofuran-5-yl)amide | 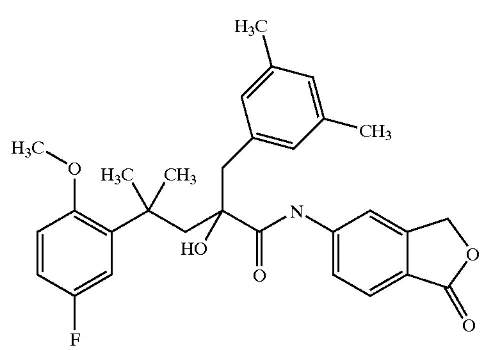 |

-continued

| Compound Name | Compound Structure |
|---|---|
| 2-(2,5-Difluorobenzyl)-4-(5-fluoro-2-methoxyphenyl)-2-hydroxy-4-methylpentanoic acid(1-oxo-1,3-dihydroisobenzofuran-5-yl)amide | 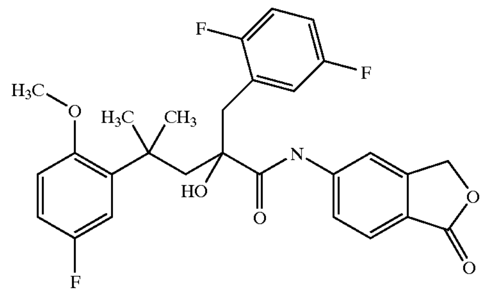 |
| 2-(2,5-Difluorobenzyl)-4-(5-fluoro-2-hydroxyphenyl)-2-hydroxy-4-methylpentanoic acid(1-oxo-1,3-dihydroisobenzofuran-5-yl)amide | 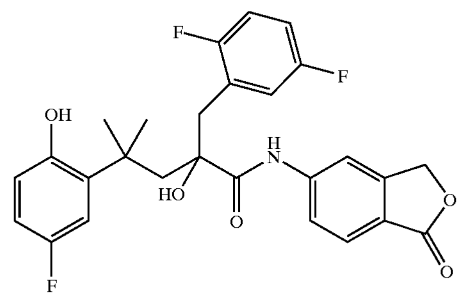 |
| 4-(5-Fluoro-2-hydroxyphenyl)-2-hydroxy-4-methyl-2-(2-methylbenzyl)pentanoic acid(1-oxo-1,3-dihydroisobenzofuran-5-yl)amide | 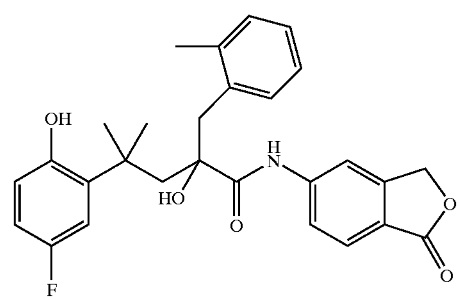 |
| 2-(3,5-Dimethylbenzyl)-4-(5-fluoro-2-hydroxyphenyl)-2-hydroxy-4-methylpentanoic acid(1-oxo-1,3-dihydroisobenzofuran-5-yl)amide | 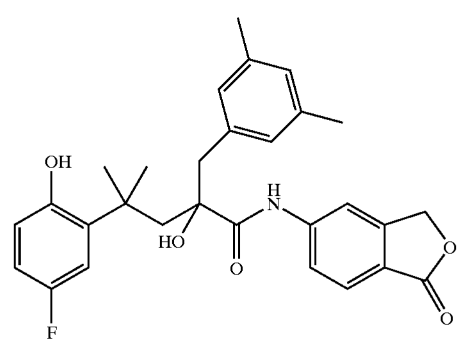 |
| 2-Cyclohexylmethyl-4-(5-fluoro-2-methoxyphenyl)-2-hydroxy-4-methylpentanoic acid(3,5-dichlorophenyl)amide | 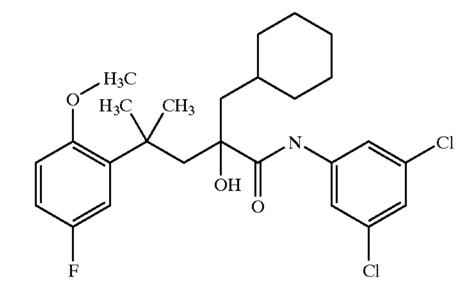 |

-continued

| Compound Name | Compound Structure |
|---|---|
| 2-Cyclohexylmethyl-4-(5-fluoro-2-hydroxyphenyl)-2-hydroxy-4-methylpentanoic acid(4-methyl-1-oxo-1H-benzo[d][1,2]oxazin-6-yl)amide | 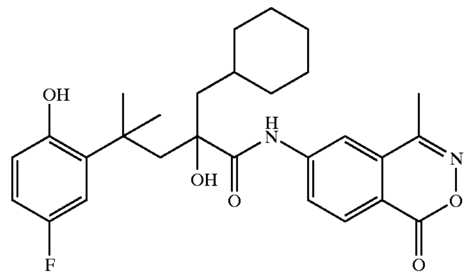 |
| 2-Benzyl-4-(5-fluoro-2-hydroxyphenyl)-2-hydroxy-4-methylpentanoic acid(3,5-dichlorophenyl)amide | 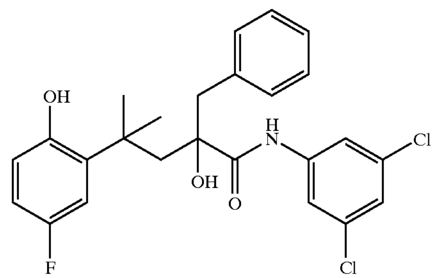 |
| 2-Cyclohexylmethyl-4-(5-fluoro-2-hydroxyphenyl)-2-hydroxy-4-methylpentanoic acid(3,5-dichlorophenyl)amide | 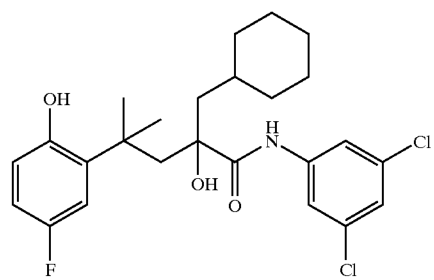 |
| 2-Benzyl-4-(5-fluoro-2-methoxyphenyl)-2-hydroxy-4-methylpentanoic acid phenylamide | 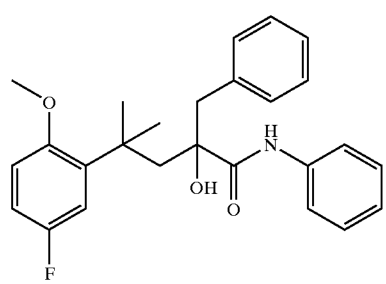 |
| 2-Cyclohexylmethyl-4-(5-fluoro-2-methoxyphenyl)-2-hydroxy-4-methylpentanoic acid phenylamide | 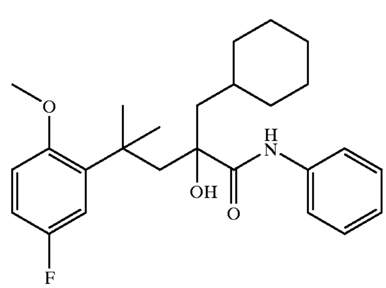 |

-continued

| Compound Name | Compound Structure |
|---|---|
| 2-(3-Chlorobenzyl)-4-(5-fluoro-2-hydroxyphenyl)-2-hydroxy-4-methylpentanoic acid(1-oxo-1,3-dihydroisobenzofuran-5-yl)amide | 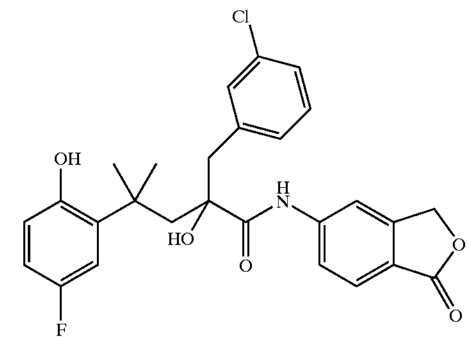 |
| 4-(5-Fluoro-2-methoxyphenyl)-2-hydroxy-2-[2-(4-methoxyphenyl)ethyl]-4-methylpentanoic acid(1-oxo-1,3-dihydroisobenzofuran-5-yl)amide | 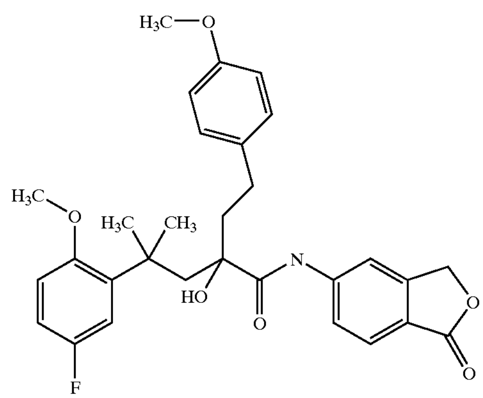 |
| 4-(5-Fluoro-2-methoxyphenyl)-2-hydroxy-2-(2-methoxybenzyl)-4-methylpentanoic acid(1-oxo-1,3-dihydroisobenzofuran-5-yl)amide | 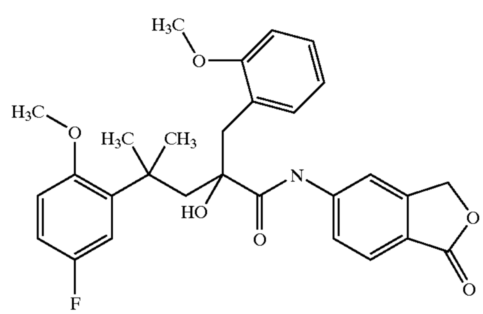 |
| 2-Benzyl-4-(5-fluoro-2-hydroxyphenyl)-2-hydroxy-4-methylpentanoic acid phenylamide | 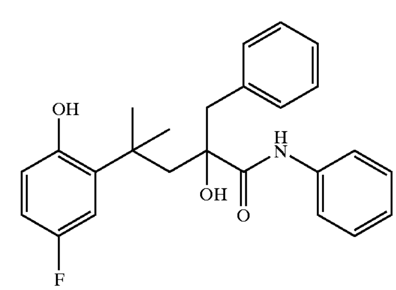 |

| Compound Name | Compound Structure |
|---|---|
| 2-Cyclohexylmethyl-4-(5-fluoro-2-hydroxyphenyl)-2-hydroxy-4-methylpentanoic acid phenylamide | 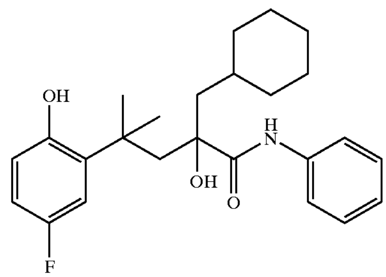 |
| 4-(5-Fluoro-2-methoxyphenyl)-2-hydroxy-4-methyl-2-phenethylpentanoic acid(1-oxo-1,3-dihydroisobenzofuran-5-yl)amide | 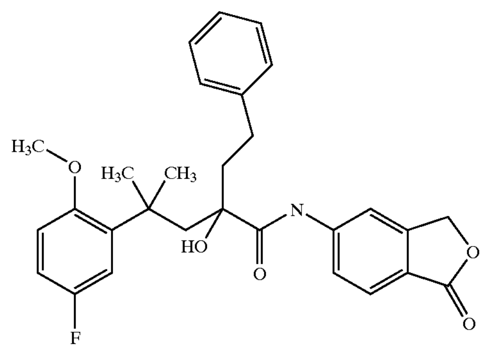 |
| 2-(2-Chlorobenzyl)-4-(5-fluoro-2-methoxyphenyl)-2-hydroxy-4-methylpentanoic acid(1-oxo-1,3-dihydroisobenzofuran-5-yl)amide | 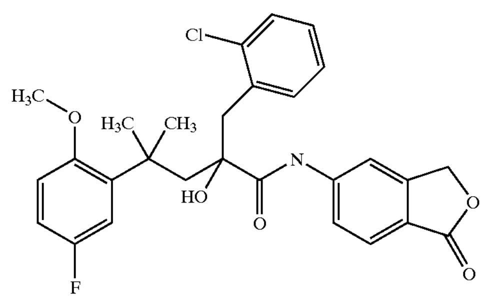 |
| 4-(5-Fluoro-2-hydroxyphenyl)-2-hydroxy-4-methyl-2-phenethylpentanoic acid(1-oxo-1,3-dihydroisobenzofuran-5-yl)amide | 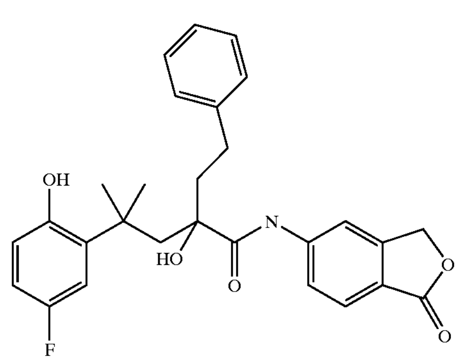 |

-continued

| Compound Name | Compound Structure |
|---|---|
| 4-(5-Fluoro-2-hydroxyphenyl)-2-hydroxy-2-[2-(4-hydroxyphenyl)ethyl]-4-methylpentanoic acid(1-oxo-1,3-dihydroisobenzofuran-5-yl)amide | 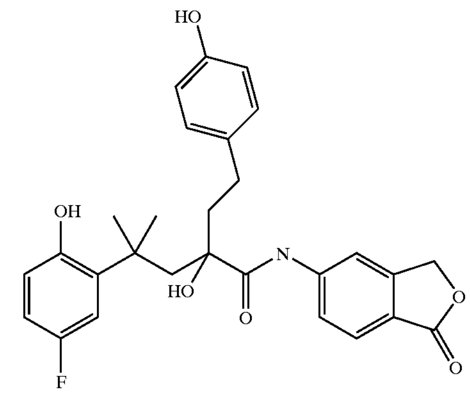 |
| 2-(2-Chlorobenzyl)-4-(5-fluoro-2-hydroxyphenyl)-2-hydroxy-4-methylpentanoic acid(1-oxo-1,3-dihydroisobenzofuran-5-yl)amide | 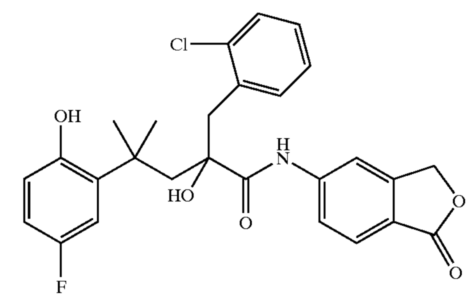 |
| 4-(5-Fluoro-2-hydroxyphenyl)-2-hydroxy-2-(2-hydroxybenzyl)-4-methylpentanoic acid(1-oxo-1,3-dihydroisobenzofuran-5-yl)amide | 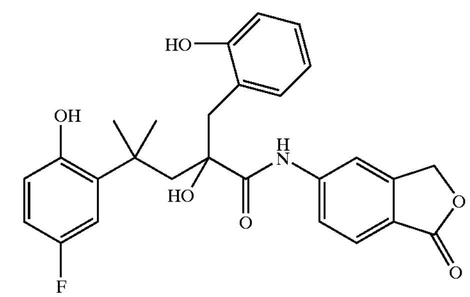 |
| 2-(2-Bromobenzyl)-4-(5-fluoro-2-methoxyphenyl)-2-hydroxy-4-methylpentanoic acid(1-oxo-1,3-dihydroisobenzofuran-5-yl)amide | 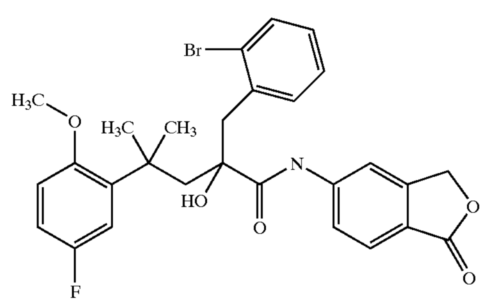 |
| 2-(2-Bromobenzyl)-4-(5-fluoro-2-hydroxyphenyl)-2-hydroxy-4-methylpentanoic acid(1-oxo-1,3-dihydroisobenzofuran-5-yl)amide | 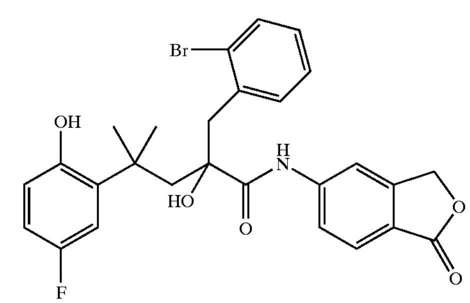 |

-continued

| Compound Name | Compound Structure |
|---|---|
| 2-Benzyl-4-(5-fluoro-2-methoxyphenyl)-2-hydroxy-4-methylpentanoic acid(3,5-dimethylphenyl)amide | 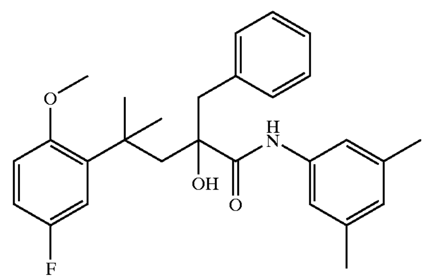 |
| 2-Cyclohexylmethyl-4-(5-fluoro-2-methoxyphenyl)-2-hydroxy-4-methylpentanoic acid(3,5-dimethylphenyl)amide | 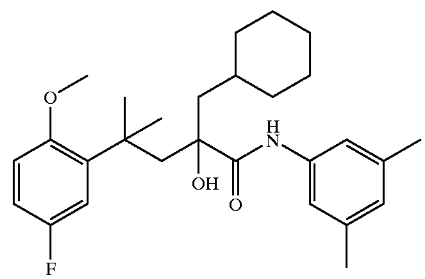 |
| 2-Benzyl-4-(5-fluoro-2-methoxyphenyl)-2-hydroxy-4-methylpentanoic acid(3,5-bis-trifluoromethylphenyl)amide | 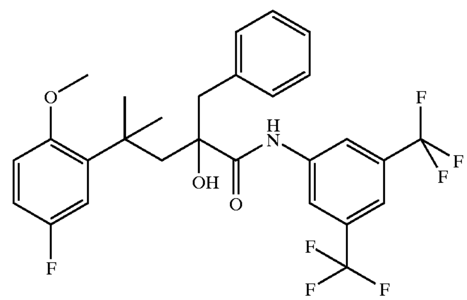 |
| 2-Cyclohexylmethyl-4-(5-fluoro-2-methoxyphenyl)-2-hydroxy-4-methylpentanoic acid(3,5-bis-trifluoromethylphenyl)amide | 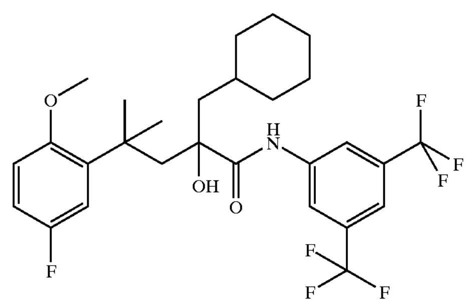 |
| 2-Benzyl-4-(5-fluoro-2-methoxyphenyl)-2-hydroxy-4-methylpentanoic acid(3,5-dimethoxyphenyl)amide | 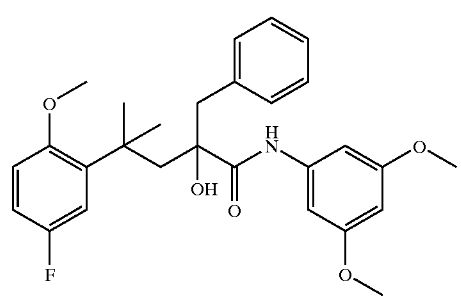 |

-continued

| Compound Name | Compound Structure |
| --- | --- |
| 2-Cyclohexylmethyl-4-(5-fluoro-2-methoxyphenyl)-2-hydroxy-4-methylpentanoic acid(3,5-dimethoxyphenyl)amide | 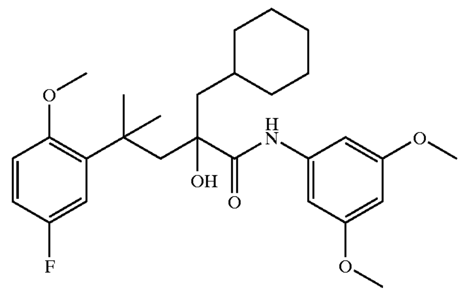 |
| 2-Benzyl-4-(5-fluoro-2-hydroxyphenyl)-2-hydroxy-4-methylpentanoic acid(3,5-dimethylphenyl)amide | 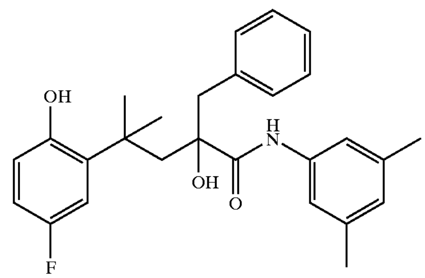 |
| 2-Cyclohexylmethyl-4-(5-fluoro-2-hydroxyphenyl)-2-hydroxy-4-methylpentanoic acid(3,5-dimethylphenyl)amide | 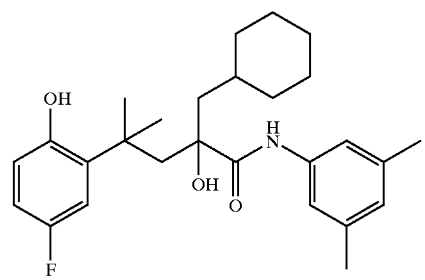 |
| 2-Benzyl-4-(5-fluoro-2-hydroxyphenyl)-2-hydroxy-4-methylpentanoic acid(3,5-bis-trifluoromethylphenyl)amide | 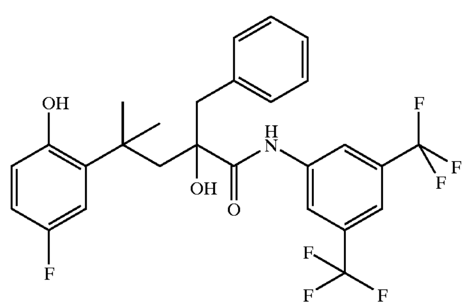 |
| 2-Cyclohexylmethyl-4-(5-fluoro-2-hydroxyphenyl)-2-hydroxy-4-methylpentanoic acid(3,5-bis-trifluoromethylphenyl)amide | 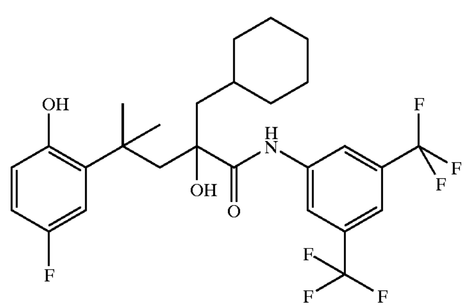 |

| Compound Name | Compound Structure |
|---|---|
| 2-Benzyl-4-(5-fluoro-2-hydroxyphenyl)-2-hydroxy-4-methylpentanoic acid(3,5-dihydroxyphenyl)amide | 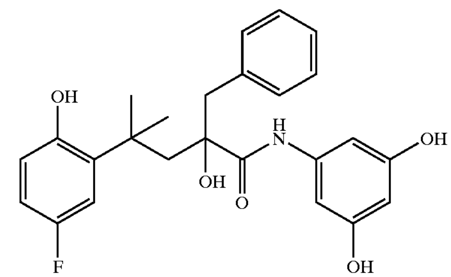 |
| 2-Cyclohexylmethyl-4-(5-fluoro-2-hydroxyphenyl)-2-hydroxy-4-methylpentanoic acid(3,5-dihydroxyphenyl)amide | 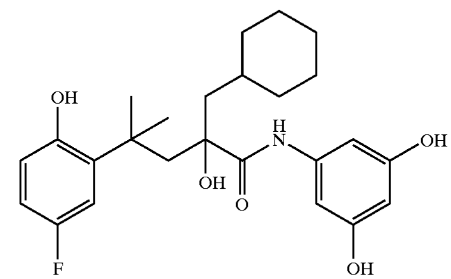 |
| 2-(5-Fluoro-2-methoxybenzyl)-2-hydroxy-4-methyl-4-phenylpentanoic acid(1-oxo-1,3-dihydroisobenzofuran-5-yl)amide | 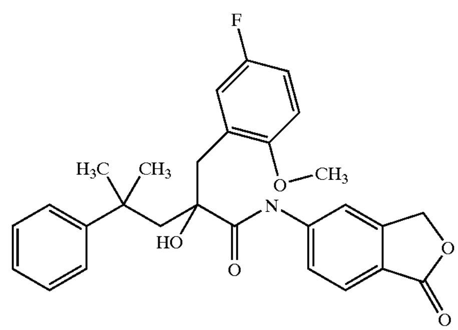 |
| 2-(5-Fluoro-2-hydroxybenzyl)-2-hydroxy-4-methyl-4-phenylpentanoic acid(1-oxo-1,3-dihydroisobenzofuran-5-yl)amide | 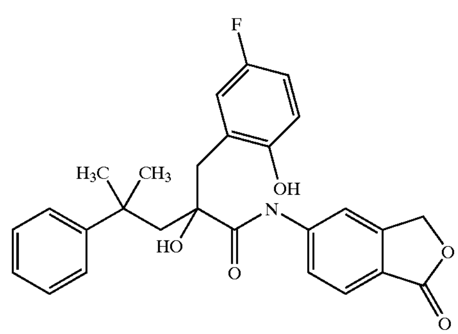 |
| 2-(5-Fluoro-2-methoxybenzyl)-4-(5-fluoro-2-methoxyphenyl)-2-hydroxy-4-methylpentanoic acid(1-oxo-1,3-dihydroisobenzofuran-5-yl)amide | 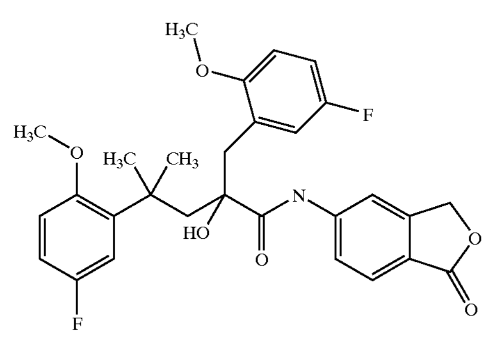 |

-continued

| Compound Name | Compound Structure |
|---|---|
| 2-(5-Fluoro-2-hydroxybenzyl)-4-(5-fluoro-2-hydroxyphenyl)-2-hydroxy-4-methylpentanoic acid(1-oxo-1,3-dihydroisobenzofuran-5-yl)amide | 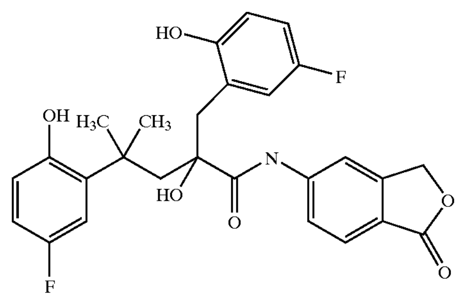 |
| 2-(3,5-Dimethoxybenzyl)-2-hydroxy-4-methyl-4-phenylpentanoic acid(1-oxo-1,3-dihydroisobenzofuran-5-yl)amide | 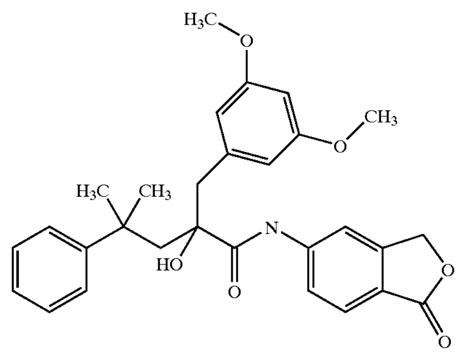 |
| 2-(3,5-Dihydroxybenzyl)-2-hydroxy-4-methyl-4-phenylpentanoic acid(1-oxo-1,3-dihydroisobenzofuran-5-yl)amide | 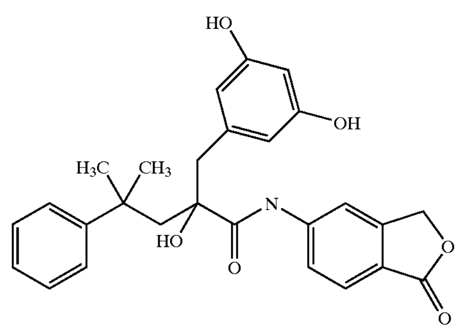 |
| 2-Hydroxy-2-(2-methoxybenzyl)-4-methyl-4-phenylpentanoic acid(1-oxo-1,3-dihydroisobenzofuran-5-yl)amide | 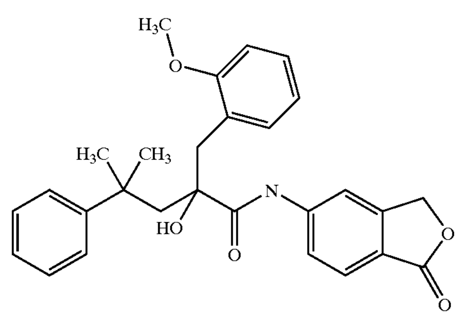 |
| 2-Hydroxy-2-(2-hydroxybenzyl)-4-methyl-4-phenylpentanoic acid(1-oxo-1,3-dihydroisobenzofuran-5-yl)amide | 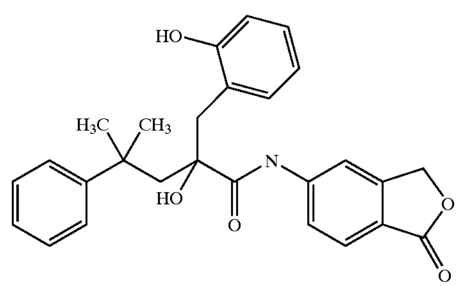 |

-continued

| Compound Name | Compound Structure |
|---|---|
| 2-Hydroxy-2-[2-(4-hydroxyphenyl)ethyl]-4-methyl-4-phenylpentanoic acid(1-oxo-1,3-dihydroisobenzofuran-5-yl)amide | 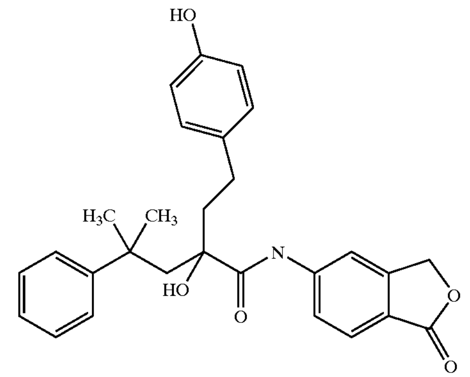 |
| 5-[2-Benzyl-4-(5-fluoro-2-methoxyphenyl)-2-hydroxy-4-methylpentylamino]-3H-isobenzofuran-1-one | 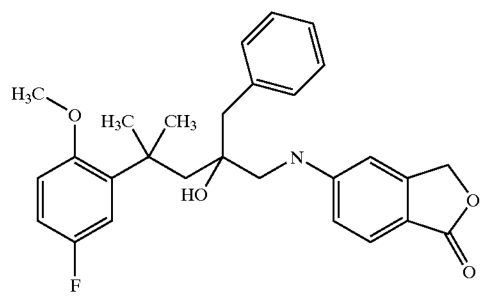 |
| 2-Benzyl-4-(5-fluoro-2-methoxyphenyl)-2-hydroxy-4-methylpentanoic acid(4-cyano-3-trifluoromethylphenyl)amide | 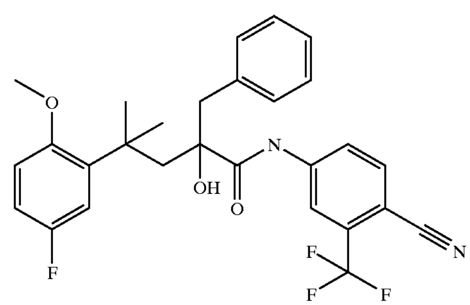 |
| 2-Benzyl-4-(5-fluoro-2-hydroxyphenyl)-2-hydroxy-4-methylpentanoic acid(4-cyano-3-trifluoromethylphenyl)amide | 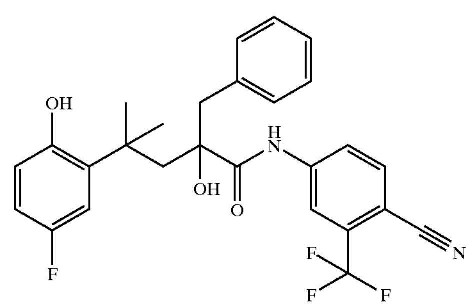 |
| 4-(5-Fluoro-2-methoxyphenyl)-2-hydroxy-4-methyl-2-(1-phenylvinyl)pentanoic acid(1-oxo-1,3-dihydroisobenzofuran-5-yl)amide | 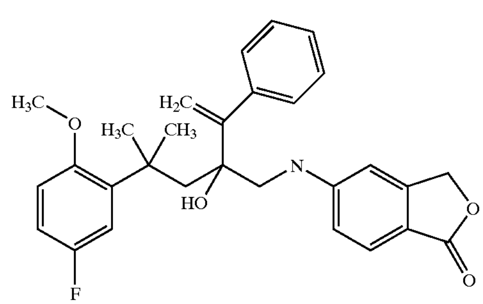 |

-continued

| Compound Name | Compound Structure |
|---|---|
| 2-Hydroxy-4-methyl-4-phenyl-2-pyridin-2-ylmethylpentanoic acid(1-oxo-1,3-dihydroisobenzofuran-5-yl)amide | 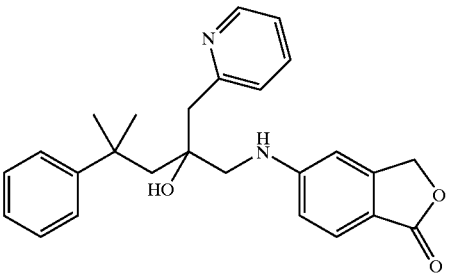 |
| 4-(5-Fluoro-2-methoxyphenyl)-2-hydroxy-4-methyl-2-(1-phenylethyl)pentanoic acid(1-oxo-1,3-dihydroisobenzofuran-5-yl)amide | 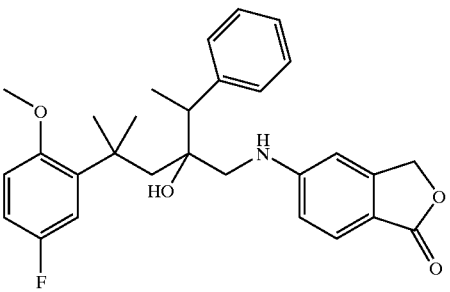 |
| 4-(5-Fluoro-2-hydroxyphenyl)-2-hydroxy-4-methyl-2-(1-phenylethyl)pentanoic acid(1-oxo-1,3-dihydroisobenzofuran-5-yl)amide | 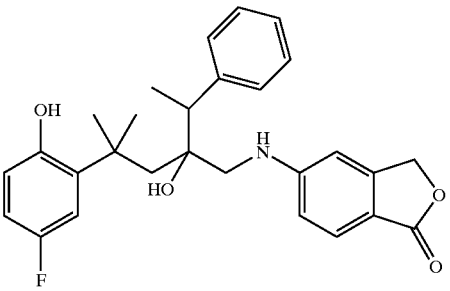 |
| 2-Benzyl-2-hydroxy-4-methyl-4-phenylpentanoic acid(4-methyl-1-oxo-1H-benzo[d][1,2]oxazin-6-yl)amide | 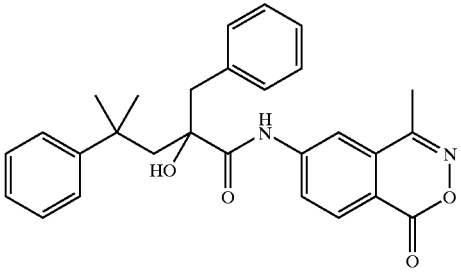 |
| 2-Cyclohexylmethyl-2-hydroxy-4-methyl-4-phenylpentanoic acid(4-methyl-1-oxo-1H-benzo[d][1,2]oxazin-6-yl)amide | 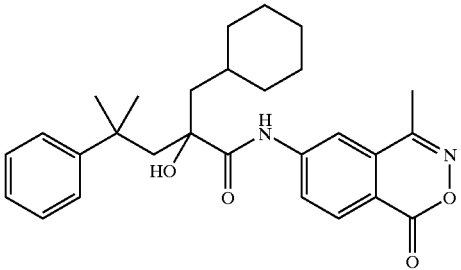 |

-continued

| Compound Name | Compound Structure |
|---|---|
| 2-Cyclohexylmethyl-4-(5-fluoro-2-methoxyphenyl)-2-hydroxy-4-methylpentanoic acid(4-cyano-3-trifluoromethylphenyl)amide | 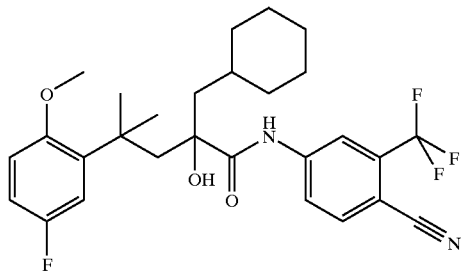 |
| 2-Cyclopentyl-4-(5-fluoro-2-methoxyphenyl)-2-hydroxy-4-methylpentanoic acid(1-oxo-1,3-dihydroisobenzofuran-5-yl)amide | 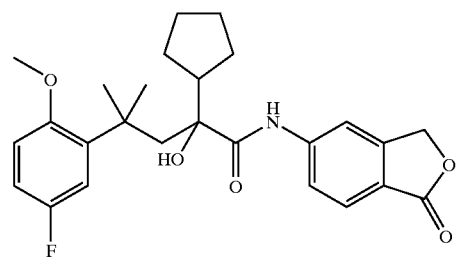 |
| 2-Cyclopentyl-4-(5-fluoro-2-hydroxyphenyl)-2-hydroxy-4-methylpentanoic acid(1-oxo-1,3-dihydroisobenzofuran-5-yl)amide | 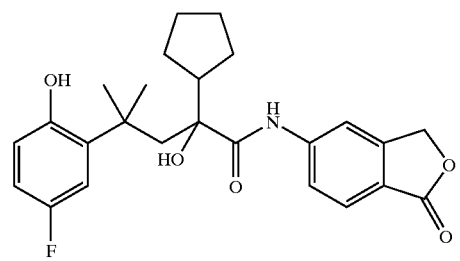 |
| 2-Cyclopentylmethyl-4-(5-fluoro-2-hydroxyphenyl)-2-hydroxy-4-methylpentanoic acid(1-oxo-1,3-dihydroisobenzofuran-5-yl)amide | 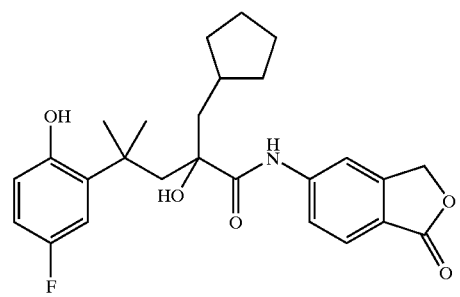 |
| 2-Benzyl-2-hydroxy-N-(1-oxo-1,3-dihydroisobenzofuran-5-yl)-4-phenyl-butyramide | 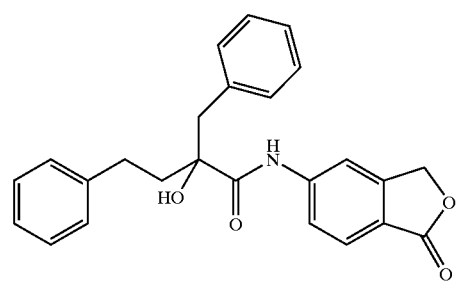 | or tautomer, prodrug, solvate, or salt thereof.

Preferred compounds include the following:

2-Benzyl-2-hydroxy-4-methyl-4-phenylpentanoic acid (1-oxo-1,3-dihydroisobenzofuran-5-yl)amide;

2-Hydroxy-4-methyl-2-phenethyl-4-phenylpentanoic acid (1-oxo-1,3-dihydroisobenzofuran-5-yl)amide;

2-Hydroxy-2-(3-methoxybenzyl)-4-methyl-4-phenylpentanoic acid (1-oxo-1,3-dihydroisobenzofuran-5-yl)amide;

2-Hydroxy-2-[2-(4-methoxyphenyl)ethyl]-4-methyl-4-phenylpentanoic acid (1-oxo-1,3-dihydroisobenzofuran-5-yl)amide;

2-Cyclohexylmethyl-2-hydroxy-4-methyl-4-phenylpentanoic acid (1-oxo-1,3-dihydroisobenzofuran-5-yl)amide;

2-(4-tert-Butylbenzyl)-2-hydroxy-4-methyl-4-phenylpentanoic acid (1-oxo-1,3-dihydroisobenzofuran-5-yl)amide;

2-Hydroxy-2-(3-hydroxybenzyl)-4-methyl-4-phenylpentanoic acid (1-oxo-1,3-dihydroisobenzofuran-5-yl)amide;

2-Hydroxy-4-methyl-2-(2-methyl-2-phenylpropyl)-4-phenylpentanoic acid (1-oxo-1,3-dihydroisobenzofuran-5-yl)amide;

2-Benzyl-4-(5-fluoro-2-methoxyphenyl)-2-hydroxy-4-methylpentanoic acid (1-oxo-1,3-dihydroisobenzofuran-5-yl)amide;

2-Cyclohexylmethyl-4-(5-fluoro-2-methoxyphenyl)-2-hydroxy-4-methylpentanoic acid (1-oxo-1,3-dihydroisobenzofuran-5-yl)amide;

2-Benzyl-4-(5-fluoro-2-hydroxyphenyl)-2-hydroxy-4-methylpentanoic acid (1-oxo-1,3-dihydroisobenzofuran-5-yl)amide;

2-Cyclohexylmethyl-4-(5-fluoro-2-hydroxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-4-methyl-2-(2-methyl-2-phenylpropyl)pentanoic acid (1-oxo-1,3-dihydroisobenzofuran-5-yl)amide;

2-(2-Chloro-6-fluorobenzyl)-4-(5-fluoro-2-methoxyphenyl)-2-hydroxy-4-methylpentanoic acid (1-oxo-1,3-dihydroisobenzofuran-5-yl)amide;

2-(3-Fluorobenzyl)-4-(5-fluoro-2-methoxyphenyl)-2-hydroxy-4-methylpentanoic acid (1-oxo-1,3-dihydroisobenzofuran-5-yl)amide;

2-(2-Fluorobenzyl)-4-(5-fluoro-2-methoxyphenyl)-2-hydroxy-4-methylpentanoic acid (1-oxo-1,3-dihydroisobenzofuran-5-yl)amide;

2-(3,4-Difluorobenzyl)-4-(5-fluoro-2-methoxyphenyl)-2-hydroxy-4-methylpentanoic acid (1-oxo-1,3-dihydroisobenzofuran-5-yl)amide;

2-(2-Chloro-6-fluorobenzyl)-4-(5-fluoro-2-hydroxyphenyl)-2-hydroxy-4-methylpentanoic acid (1-oxo-1,3-dihydroisobenzofuran-5-yl)amide;

2-(3-Fluorobenzyl)-4-(5-fluoro-2-hydroxyphenyl)-2-hydroxy-4-methylpentanoic acid (1-oxo-1,3-dihydroisobenzofuran-5-yl)amide;

2-(2-Fluorobenzyl)-4-(5-fluoro-2-hydroxyphenyl)-2-hydroxy-4-methylpentanoic acid (1-oxo-1,3-dihydroisobenzofuran-5-yl)amide;

2-(3,4-Difluorobenzyl)-4-(5-fluoro-2-hydroxyphenyl)-2-hydroxy-4-methylpentanoic acid (1-oxo-1,3-dihydroisobenzofuran-5-yl)amide;

2-(4-Fluorobenzyl)-4-(5-fluoro-2-methoxyphenyl)-2-hydroxy-4-methylpentanoic acid (1-oxo-1,3-dihydroisobenzofuran-5-yl)amide;

2-(4-Fluorobenzyl)-4-(5-fluoro-2-hydroxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-4-methyl-2-(3-methylbenzyl)pentanoic acid (1-oxo-1,3-dihydroisobenzofuran-5-yl)amide;

2-Benzyl-4-(5-fluoro-2-methoxyphenyl)-2-hydroxy-4-methylpentanoic acid (4-methyl-1-oxo-1H-benzo[d][1,2]oxazin-6-yl)amide;

2-Benzyl-4-(5-fluoro-2-hydroxyphenyl)-2-hydroxy-4-methylpentanoic acid (4-methyl-1-oxo-1H-benzo[d][1,2]oxazin-6-yl)amide;

2-Cyclohexylmethyl-4-(5-fluoro-2-methoxyphenyl)-2-hydroxy-4-methylpentanoic acid (4-methyl-1-oxo-1H-benzo[d][1,2]oxazin-6-yl)amide;

2-Benzyl-4-(5-fluoro-2-methoxyphenyl)-2-hydroxy-4-methylpentanoic acid (3,5-dichlorophenyl)amide;

4-(5-Fluoro-2-methoxyphenyl)-2-hydroxy-4-methyl-2-(2-methylbenzyl)pentanoic acid (1-oxo-1,3-dihydroisobenzofuran-5-yl)amide;

2-(2,5-Difluorobenzyl)-4-(5-fluoro-2-methoxyphenyl)-2-hydroxy-4-methylpentanoic acid (1-oxo-1,3-dihydroisobenzofuran-5-yl)amide;

2-(2,5-Difluorobenzyl)-4-(5-fluoro-2-hydroxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-4-methyl-2-(2-methylbenzyl)pentanoic acid (1-oxo-1,3-dihydroisobenzofuran-5-yl)amide;

2-Cyclohexylmethyl-4-(5-fluoro-2-methoxyphenyl)-2-hydroxy-4-methylpentanoic acid (3,5-dichlorophenyl)amide;

2-Cyclohexylmethyl-4-(5-fluoro-2-hydroxyphenyl)-2-hydroxy-4-methylpentanoic acid (4-methyl-1-oxo-1H-benzo[d][1,2]oxazin-6-yl)amide;

2-Cyclohexylmethyl-4-(5-fluoro-2-hydroxyphenyl)-2-hydroxy-4-methylpentanoic acid (3,5-dichlorophenyl)amide;

2-(3-Chlorobenzyl)-4-(5-fluoro-2-hydroxyphenyl)-2-hydroxy-4-methylpentanoic acid (1-oxo-1,3-dihydroisobenzofuran-5-yl)amide;

4-(5-Fluoro-2-methoxyphenyl)-2-hydroxy-2-(2-methoxybenzyl)-4-methylpentanoic acid (1-oxo-1,3-dihydroisobenzofuran-5-yl)amide;

4-(5-Fluoro-2-methoxyphenyl)-2-hydroxy-4-methyl-2-phenethylpentanoic acid (1-oxo-1,3-dihydroisobenzofuran-5-yl)amide;

2-(2-Chlorobenzyl)-4-(5-fluoro-2-methoxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-4-methyl-2-phenethylpentanoic acid (1-oxo-1,3-dihydroisobenzofuran-5-yl)amide;

4-(5-Fluoro-2-hydroxyphenyl)-2-hydroxy-2-[2-(4-hydroxyphenyl)ethyl]-4-methylpentanoic acid (1-oxo-1,3-dihydroisobenzofuran-5-yl)amide;

2-(2-Chlorobenzyl)-4-(5-fluoro-2-hydroxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-2-(2-hydroxybenzyl)-4-methylpentanoic acid (1-oxo-1,3-dihydroisobenzofuran-5-yl)amide;

2-(2-Bromobenzyl)-4-(5-fluoro-2-methoxyphenyl)-2-hydroxy-4-methylpentanoic acid (1-oxo-1,3-dihydroisobenzofuran-5-yl)amide;

2-(2-Bromobenzyl)-4-(5-fluoro-2-hydroxyphenyl)-2-hydroxy-4-methylpentanoic acid (1-oxo-1,3-dihydroisobenzofuran-5-yl)amide;

2-Cyclohexylmethyl-4-(5-fluoro-2-methoxyphenyl)-2-hydroxy-4-methylpentanoic acid (3,5-bis-trifluoromethylphenyl)amide;

2-Hydroxy-2-(2-methoxybenzyl)-4-methyl-4-phenylpentanoic acid (1-oxo-1,3-dihydroisobenzofuran-5-yl)amide;
2-Hydroxy-2-(2-hydroxybenzyl)-4-methyl-4-phenylpentanoic acid (1-oxo-1,3-dihydroisobenzofuran-5-yl)amide;
5-[2-Benzyl-4-(5-fluoro-2-methoxyphenyl)-2-hydroxy-4-methylpentylamino]-3H-isobenzofuran-1-one;
2-Benzyl-4-(5-fluoro-2-methoxyphenyl)-2-hydroxy-4-methylpentanoic acid (4-cyano-3-trifluoromethylphenyl)amide;
2-Benzyl-4-(5-fluoro-2-hydroxyphenyl)-2-hydroxy-4-methylpentanoic acid (4-cyano-3-trifluoromethylphenyl)amide;
4-(5-Fluoro-2-methoxyphenyl)-2-hydroxy-4-methyl-2-(1-phenylvinyl)pentanoic acid (1-oxo-1,3-dihydroisobenzofuran-5-yl)amide;
4-(5-Fluoro-2-hydroxyphenyl)-2-hydroxy-4-methyl-2-(1-phenylethyl)pentanoic acid (1-oxo-1,3-dihydroisobenzofuran-5-yl)amide;
2-Benzyl-2-hydroxy-4-methyl-4-phenylpentanoic acid (4-methyl-1-oxo-1H-benzo[d][1,2]oxazin-6-yl)amide;
2-Cyclohexylmethyl-2-hydroxy-4-methyl-4-phenylpentanoic acid (4-methyl-1-oxo-1H-benzo[d][1,2]oxazin-6-yl)amide;
2-Cyclohexylmethyl-4-(5-fluoro-2-methoxyphenyl)-2-hydroxy-4-methylpentanoic acid (4-cyano-3-trifluoromethylphenyl)amide;
2-Cyclopentyl-4-(5-fluoro-2-methoxyphenyl)-2-hydroxy-4-methylpentanoic acid (1-oxo-1,3-dihydroisobenzofuran-5-yl)amide;
2-Cyclopentyl-4-(5-fluoro-2-hydroxyphenyl)-2-hydroxy-4-methylpentanoic acid (1-oxo-1,3-dihydroisobenzofuran-5-yl)amide; and
2-Cyclopentylmethyl-4-(5-fluoro-2-hydroxyphenyl)-2-hydroxy-4-methylpentanoic acid (1-oxo-1,3-dihydroisobenzofuran-5-yl)amide,
or a tautomer, prodrug, solvate, or salt thereof.

More preferred compounds include:
2-Benzyl-2-hydroxy-4-methyl-4-phenylpentanoic acid (1-oxo-1,3-dihydroisobenzofuran-5-yl)amide;
2-Cyclohexylmethyl-2-hydroxy-4-methyl-4-phenylpentanoic acid (1-oxo-1,3-dihydroisobenzofuran-5-yl)amide;
2-Hydroxy-4-methyl-2-(2-methyl-2-phenylpropyl)-4-phenylpentanoic acid (1-oxo-1,3-dihydroisobenzofuran-5-yl)amide;
2-Benzyl-4-(5-fluoro-2-methoxyphenyl)-2-hydroxy-4-methylpentanoic acid (1-oxo-1,3-dihydroisobenzofuran-5-yl)amide;
2-Cyclohexylmethyl-4-(5-fluoro-2-methoxyphenyl)-2-hydroxy-4-methylpentanoic acid (1-oxo-1,3-dihydroisobenzofuran-5-yl)amide;
2-Cyclohexylmethyl-4-(5-fluoro-2-hydroxyphenyl)-2-hydroxy-4-methylpentanoic acid (1-oxo-1,3-dihydroisobenzofuran-5-yl)amide;
2-(3-Fluorobenzyl)-4-(5-fluoro-2-methoxyphenyl)-2-hydroxy-4-methylpentanoic acid (1-oxo-1,3-dihydroisobenzofuran-5-yl)amide;
2-(2-Fluorobenzyl)-4-(5-fluoro-2-methoxyphenyl)-2-hydroxy-4-methylpentanoic acid (1-oxo-1,3-dihydroisobenzofuran-5-yl)amide;
2-(2-Fluorobenzyl)-4-(5-fluoro-2-hydroxyphenyl)-2-hydroxy-4-methylpentanoic acid (1-oxo-1,3-dihydroisobenzofuran-5-yl)amide;
2-(3,4-Difluorobenzyl)-4-(5-fluoro-2-hydroxyphenyl)-2-hydroxy-4-methylpentanoic acid (1-oxo-1,3-dihydroisobenzofuran-5-yl)amide;
2-(4-Fluorobenzyl)-4-(5-fluoro-2-hydroxyphenyl)-2-hydroxy-4-methylpentanoic acid (1-oxo-1,3-dihydroisobenzofuran-5-yl)amide;
2-Benzyl-4-(5-fluoro-2-methoxyphenyl)-2-hydroxy-4-methylpentanoic acid (4-methyl-1-oxo-1H-benzo[d][1,2]oxazin-6-yl)amide;
2-Benzyl-4-(5-fluoro-2-hydroxyphenyl)-2-hydroxy-4-methylpentanoic acid (4-methyl-1-oxo-1H-benzo[d][1,2]oxazin-6-yl)amide;
2-Cyclohexylmethyl-4-(5-fluoro-2-methoxyphenyl)-2-hydroxy-4-methylpentanoic acid (4-methyl-1-oxo-1H-benzo[d][1,2]oxazin-6-yl)amide;
4-(5-Fluoro-2-methoxyphenyl)-2-hydroxy-4-methyl-2-(2-methylbenzyl)pentanoic acid (1-oxo-1,3-dihydroisobenzofuran-5-yl)amide;
4-(5-Fluoro-2-hydroxyphenyl)-2-hydroxy-4-methyl-2-(2-methylbenzyl)pentanoic acid (1-oxo-1,3-dihydroisobenzofuran-5-yl)amide;
2-Cyclohexylmethyl-4-(5-fluoro-2-hydroxyphenyl)-2-hydroxy-4-methylpentanoic acid (4-methyl-1-oxo-1H-benzo[d][1,2]oxazin-6-yl)amide;
2-(2-Chlorobenzyl)-4-(5-fluoro-2-methoxyphenyl)-2-hydroxy-4-methylpentanoic acid (1-oxo-1,3-dihydroisobenzofuran-5-yl)amide;
4-(5-Fluoro-2-hydroxyphenyl)-2-hydroxy-4-methyl-2-phenethylpentanoic acid (1-oxo-1,3-dihydroisobenzofuran-5-yl)amide;
2-(2-Chlorobenzyl)-4-(5-fluoro-2-hydroxyphenyl)-2-hydroxy-4-methylpentanoic acid (1-oxo-1,3-dihydroisobenzofuran-5-yl)amide;
4-(5-Fluoro-2-hydroxyphenyl)-2-hydroxy-2-(2-hydroxybenzyl)-4-methylpentanoic acid (1-oxo-1,3-dihydroisobenzofuran-5-yl)amide;
2-(2-Bromobenzyl)-4-(5-fluoro-2-methoxyphenyl)-2-hydroxy-4-methylpentanoic acid (1-oxo-1,3-dihydroisobenzofuran-5-yl)amide;
2-(2-Bromobenzyl)-4-(5-fluoro-2-hydroxyphenyl)-2-hydroxy-4-methylpentanoic acid (1-oxo-1,3-dihydroisobenzofuran-5-yl)amide;
5-[2-Benzyl-4-(5-fluoro-2-methoxyphenyl)-2-hydroxy-4-methylpentylamino]-3H-isobenzofuran-1-one;
4-(5-Fluoro-2-hydroxyphenyl)-2-hydroxy-4-methyl-2-(1-phenylethyl)pentanoic acid (1-oxo-1,3-dihydroisobenzofuran-5-yl)amide;
2-Benzyl-2-hydroxy-4-methyl-4-phenylpentanoic acid (4-methyl-1-oxo-1H-benzo[d][1,2]oxazin-6-yl)amide;
2-Cyclohexylmethyl-2-hydroxy-4-methyl-4-phenylpentanoic acid (4-methyl-1-oxo-1H-benzo[d][1,2]oxazin-6-yl)amide;
2-Cyclopentyl-4-(5-fluoro-2-hydroxyphenyl)-2-hydroxy-4-methylpentanoic acid (1-oxo-1,3-dihydroisobenzofuran-5-yl)amide; and
2-Cyclopentylmethyl-4-(5-fluoro-2-hydroxyphenyl)-2-hydroxy-4-methylpentanoic acid (1-oxo-1,3-dihydroisobenzofuran-5-yl)amide,
or a tautomer, prodrug, solvate, or salt thereof.

In another aspect of the invention, the compounds according to the invention are formulated into pharmaceutical compositions comprising an effective amount, preferably a pharmaceutically effective amount, of a compound according to the invention or a tautomer, prodrug, solvate, or salt thereof, and a pharmaceutically acceptable excipient or carrier.

The invention also provides a method of modulating the glucocorticoid receptor function in a patient, the method comprising administering to the patient an effective amount of a compound according to the invention or a tautomer, prodrug, solvate, or salt thereof.

The invention further provides a method of treating a disease-state or condition mediated by the glucocorticoid receptor function in a patient in need of such treatment, the method comprising administering to the patient an effective amount of a pharmaceutically acceptable compound according to the invention or a tautomer, prodrug, solvate, or salt thereof.

In addition, the invention also provides a method of treating a disease-state or condition selected from: type II diabetes, obesity, cardiovascular diseases, hypertension, arteriosclerosis, neurological diseases, adrenal and pituitary tumors, and glaucoma, in a patient in need of such treatment, the method comprising administering to the patient an effective amount of a pharmaceutically acceptable compound according to the invention or a tautomer, prodrug, solvate, or salt thereof.

The invention provides a method of treating a disease characterized by inflammatory, allergic, or proliferative processes, in a patient in need of such treatment, the method comprising administering to the patient an effective amount of a pharmaceutically acceptable compound according to the invention or a tautomer, prodrug, solvate, or salt thereof. In a preferred embodiment of the invention, the disease characterized by inflammatory, allergic, or proliferative processes is selected from: (i) lung diseases; (ii) rheumatic diseases or autoimmune diseases or joint diseases; (iii) allergic diseases; (iv) vasculitis diseases; (v) dermatological diseases; (vi) renal diseases; (vii) hepatic diseases; (viii) gastrointestinal diseases; (ix) proctological diseases; (x) eye diseases; (xi) diseases of the ear, nose, and throat (ENT) area; (xii) neurological diseases; (xiii) blood diseases; (xiv) tumor diseases; (xv) endocrine diseases; (xvi) organ and tissue transplantations and graft-versus-host diseases; (xvii) severe states of shock; (xviii) substitution therapy; and (xix) pain of inflammatory genesis. In another preferred embodiment of the invention, the disease characterized by inflammatory, allergic, or proliferative processes is selected from: type I diabetes, osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis, and syndromes associated with hemodialysis, leukopheresis, and granulocyte transfusion.

The invention further provides a method of assaying the glucocorticoid receptor function in a sample, comprising: (a) contacting the sample with a selected amount of a compound according to the invention or a tautomer, prodrug, solvate, or salt thereof; and (b) detecting the amount of the compound according to the invention or a tautomer, prodrug, solvate, or salt thereof bound to glucocorticoid receptors in the sample. In a preferred embodiment of the invention, the compound according to the invention or a tautomer, prodrug, solvate, or salt thereof is labeled with a detectable marker selected from: a radiolabel, fluorescent tag, a chemiluminescent tag, a chromophore, and a spin label.

The invention also provides a method of imaging the glucocorticoid receptor distribution in a sample or patient, the method comprising: (a) contacting the sample or administering to a patient a compound according to the invention or a tautomer, prodrug, solvate, or salt thereof having a detectable marker; (b) detecting the spatial distribution and amount of the compound according to the invention or a tautomer, prodrug, solvate, or salt thereof having a detectable marker bound to glucocorticoid receptors in the sample or patient using an imaging means to obtain an image; and (c) displaying an image of the spatial distribution and amount of the compound according to the invention or a tautomer, prodrug, solvate, or salt thereof having a detectable marker bound to glucocorticoid receptors in the sample. In a preferred embodiment of the invention, the imaging means is selected from: radioscintigraphy, nuclear magnetic resonance imaging (MRI), computed tomography (CT scan), or positron emission tomography (PET).

The invention also provides a kit for the in vitro diagnostic determination of the glucocorticoid receptor function in a sample, comprising: (a) a diagnostically effective amount of a compound according to the invention or a tautomer, prodrug, solvate, or salt thereof; and (b) instructions for use of the diagnostic kit.

The invention also provides a method of making a compound of Formula (I)

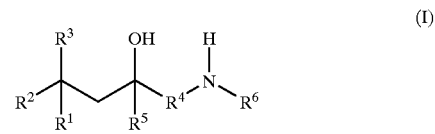

(I)

where $R^1$, $R^2$, $R^3$, $R^5$, and $R^6$ are as defined above and $R^4$ is C=O, the method comprising:

(a) reacting a compound of Formula (II) with diethyl oxalate in a suitable solvent to form a ketoester of Formula (III)

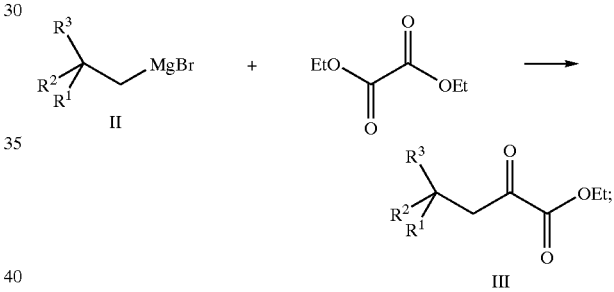

(b) hydrolyzing the ketoester of Formula (III) to form a carboxylic acid of Formula (IV)

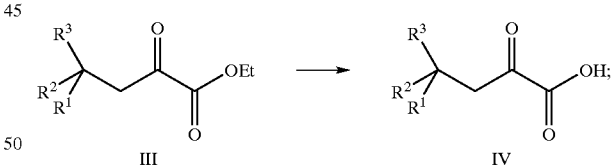

(c) coupling the carboxylic acid of Formula (IV) with an amine $R^6NH_2$ using suitable coupling conditions to form an amide of Formula (V)

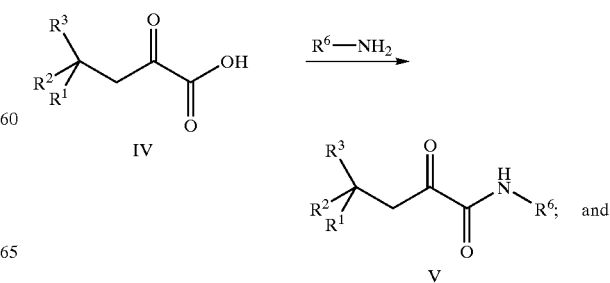

and (d) reacting the amide of Formula (V) with $R^5M$ where M is Li or MgX, and X is Cl, Br, or I, in a suitable solvent to form the compound of Formula (I) where $R^4$ is C=O

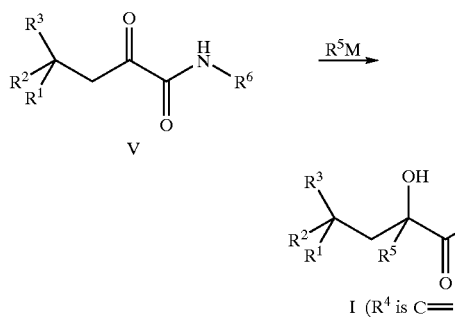

(a') reacting an aryl bromide $R^1Br$ with a suitable organometallic reagent in a suitable solvent and reacting the resulting anion with a ketone bearing $R^2$ and $R^3$ to give an alcohol of Formula (VI)

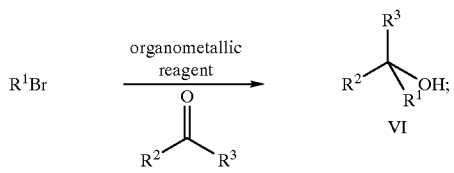

(b') reacting the alcohol of Formula (VI) with the trimethylsilyl enol ether derived from ethyl pyruvate, in the presence of a suitable Lewis acid, in a suitable solvent to provide a ketoester of Formula (III)

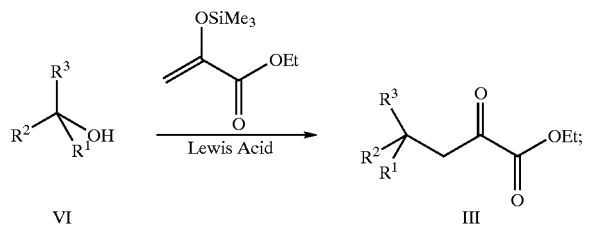

and performing steps (b), (c), and (d), as set forth above.

The invention further provides a method of making a compound of Formula (I)

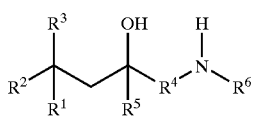

where $R^1$, $R^2$, $R^3$, $R^5$, and $R^6$ are as defined above and $R^4$ is $CH_2$, the method comprising:

(a) reacting an aryl or heteroaryl bromide with a suitable organometallic reagent in a suitable solvent and treating the resulting anion with a solution of cuprous iodide in dimethylsulfide followed by a methyl vinyl ketone of Formula (VII) bearing $R_2$ and $R_3$ to form a methyl ketone of Formula (VIII)

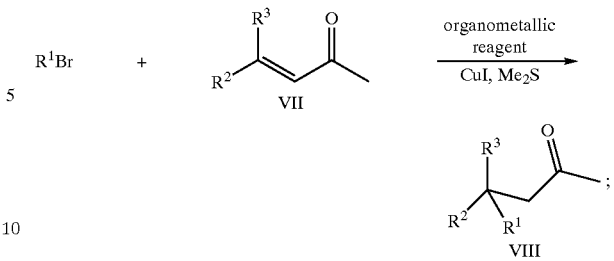

(b) reacting the methyl ketone of Formula (VIII) with a suitable brominating agent to form a bromoketone of Formula (IX)

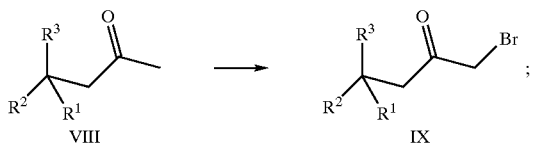

(c) reacting the bromoketone of Formula (IX) with an amine $R^6NH_2$ in a suitable solvent to form an aminoketone of Formula (X)

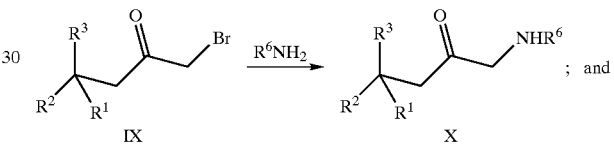

(d) reacting the aminoketone of Formula (X) with $R^5M$ where M is Li or MgX, and X is Cl, Br, or I, in a suitable solvent to form the compound of Formula (I) where $R^4$ is $CH_2$

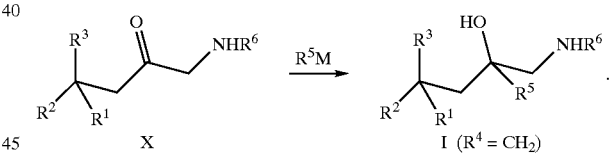

DETAILED DESCRIPTION OF THE INVENTION

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1$–$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar—, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, decenyl, and the like.

The terms "alkynyl" or "alkynyl group" mean a branched or straight-chain aliphatic hydrocarbon monovalent radical containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkenylene" or "alkenylene group" mean a branched or straight-chain aliphatic hydrocarbon divalent radical having the specified number of carbon atoms and at least one carbon-carbon double bond. This term is exemplified by groups such as ethenylene, propenylene, n-butenylene, and the like, and may alternatively and equivalently be denoted herein as -(alkylenyl)-.

The terms "alkynylene" or "alkynylene group" mean a branched or straight-chain aliphatic hydrocarbon divalent radical containing at least one carbon-carbon triple bond. This term is exemplified by groups such as ethynylene, propynylene, n-butynylene, 2-butynylene, 3-methylbutynylene, n-pentynylene, heptynylene, octynylene, decynylene, and the like, and may alternatively and equivalently be denoted herein as -(alkynyl)-.

The terms "alkoxy" or "alkoxy group" mean a monovalent radical of the formula AlkO—, where Alk is an alkyl group. This term is exemplified by groups such as methoxy, ethoxy, propoxy, isopropoxy, butoxy, sec-butoxy, tert-butoxy, pentoxy, and the like.

The terms "aryloxy", "aryloxy group", mean a monovalent radical of the formula ArO—, where Ar is aryl. This term is exemplified by groups such as phenoxy, naphthoxy, and the like.

The terms "alkylcarbonyl", "alkylcarbonyl group", "alkanoyl", or "alkanoyl group" mean a monovalent radical of the formula AlkC(O)—, where Alk is alkyl or hydrogen.

The terms "arylcarbonyl", "arylcarbonyl group", "aroyl" or "aroyl group" mean a monovalent radical of the formula ArC(O)—, where Ar is aryl.

The terms "acyl" or "acyl group" mean a monovalent radical of the formula RC(O)—, where R is a substituent selected from hydrogen or an organic substituent. Exemplary substituents include alkyl, aryl, arylalkyl, cycloalkyl, heterocyclyl, heteroaryl, heteroarylalkyl, and the like. As such, the terms comprise alkylcarbonyl groups and arylcarbonyl groups.

The terms "acylamino" or "acylamino group" mean a monovalent radical of the formula RC(O)N(R)—, where each R is a substituent selected from hydrogen or a substituent group.

The terms "alkoxycarbonyl" or "alkoxycarbonyl group" mean a monovalent radical of the formula AlkO—C(O)—, where Alk is alkyl. Exemplary alkoxycarbonyl groups include methoxycarbonyl, ethoxycarbonyl, tert-butyloxycarbonyl, and the like.

The terms "aryloxycarbonyl" or "aryloxycarbonyl group" mean a monovalent radical of the formula ArO—C(O)—, where Ar is aryl.

The terms "alkylcarbonyloxy" or "alkylcarbonyloxy group" or "alkanoyloxy" or "alkanoyloxy group" mean a monovalent radical of the formula AlkC(O)O—, where Alk is alkyl.

The terms "arylcarbonyloxy" or "arylcarbonyloxy group" or "aroyloxy" or "aroyloxy group" mean a monovalent radical of the formula ArC(O)O—, where Ar is aryl.

The terms "alkylaminocarbonyloxy" or "alkylaminocarbonyloxy group" mean a monovalent radical of the formula $R_2NC(O)O$—, where each R is independently hydrogen or lower alkyl.

The term "alkoxycarbonylamino" or "alkoxycarbonylamino group" mean a monovalent radical of the formula ROC(O)NH—, where R is lower alkyl.

The terms "alkylcarbonylamino" or "alkylcarbonylamino group" or "alkanoylamino" or "alkanoylamino groups" mean a monovalent radical of the formula AlkC(O)NH—, where Alk is alkyl. Exemplary alkylcarbonylamino groups include acetamido ($CH_3C(O)NH$—).

The terms "alkylaminocarbonyloxy" or "alkylaminocarbonyloxy group" mean a monovalent radical of the formula AlkNHC(O)O—, where Alk is alkyl.

The terms "amino" or "amino group" mean an —$NH_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —$NR_2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "alkoxycarbonylamino" or "alkoxycarbonylamino group" mean a monovalent radical of the formula AlkOC(O)NH—, where Alk is alkyl.

The terms "ureido" or "ureido group" mean a monovalent radical of the formula $R_2NC(O)NH$—, where each R is independently hydrogen or alkyl.

The terms "halogen" or "halogen group" mean a fluoro, chloro, bromo, or iodo group.

The term "halo" means one or more hydrogen atoms of the group are replaced by halogen groups.

The terms "haloalkyl" or "haloalkyl group" mean a branched or straight-chain saturated aliphatic hydrocarbon monovalent radical, wherein one or more hydrogen atoms thereof are each independently replaced with halogen atoms. This term is exemplified by groups such as chloromethyl, 1,2-dibromoethyl, 1,1,1-trifluoropropyl, 2-iodobutyl, 1-chloro-2-bromo-3-fluoropentyl, and the like.

The terms "sulfanyl", "sulfanyl group", "thioether", or "thioether group" mean a divalent radical of the formula —S—.

The terms "alkylthio" or "alkylthio group" mean a monovalent radical of the formula AlkS—, where Alk is alkyl. Exemplary groups include methylthio, ethylthio, n-propylthio, isopropylthio, n-butylthio, and the like.

The terms "arylthio" or "arylthio group" mean a monovalent radical of the formula ArS—, where Ar is aryl.

The terms "sulfinyl", "sulfinyl group", "thionyl", or "thionyl group" mean a divalent radical of the formula —SO—.

The terms "sulfonyl" or "sulfonyl group" mean a divalent radical of the formula —$SO_2$—.

The terms "sulfonylamino" or "sulfonylamino group" mean a divalent radical of the formula —$SO_2$NR—, where R is a hydrogen or a substituent group.

The terms "aminosulfonyl" or "aminosulfonyl group" mean a monovalent radical of the formula $NR_2SO_2$—, where R is each independently a hydrogen or a substituent group.

The terms "carbocycle" or "carbocyclic group" mean a stable aliphatic 3- to 15-membered monocyclic or polycyclic monovalent or divalent radical consisting solely of carbon and hydrogen atoms which may comprise one or more fused or bridged ring(s), preferably a 5- to 7-membered monocyclic or 7- to 10-membered bicyclic ring. Unless otherwise specified, the carbocycle may be attached at any carbon atom which results in a stable structure and, if substituted, may be substituted at any suitable carbon atom which results in a stable structure. The term comprises cycloalkyl (including spiro cycloalkyl), cycloalkylene, cycloalkenyl, cycloalkenylene, cycloalkynyl, and cycloalkynylene, and the like.

The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornyl, adamantyl, tetrahydronaphthyl (tetralin), 1-decalinyl, bicyclo[2.2.2]octanyl, 1-methylcyclopropyl, 2-methylcyclopentyl, 2-methylcyclooctyl, and the like.

The terms "cycloalkenyl" or "cycloalkenyl group" mean a stable aliphatic 5- to 15-membered monocyclic or polycyclic monovalent radical having at least one carbon-carbon double bond and consisting solely of carbon and hydrogen atoms which may comprise one or more fused or bridged ring(s), preferably a 5- to 7-membered monocyclic or 7- to 10-membered bicyclic ring. Unless otherwise specified, the cycloalkenyl ring may be attached at any carbon atom which results in a stable structure and, if substituted, may be substituted at any suitable carbon atom which results in a stable structure. Exemplary cycloalkenyl groups include cyclopentenyl, cyclohexenyl, cycloheptenyl, cyclooctenyl, cyclononenyl, cyclodecenyl, norbornenyl, 2-methylcyclopentenyl, 2-methylcyclooctenyl, and the like.

The terms "cycloalkynyl" or "cycloalkynyl group" mean a stable aliphatic 8- to 15-membered monocyclic or polycyclic monovalent radical having at least one carbon-carbon triple bond and consisting solely of carbon and hydrogen atoms which may comprise one or more fused or bridged ring(s), preferably a 8- to 10-membered monocyclic or 12- to 15-membered bicyclic ring. Unless otherwise specified, the cycloalkynyl ring may be attached at any carbon atom which results in a stable structure and, if substituted, may be substituted at any suitable carbon atom which results in a stable structure. Exemplary cycloalkynyl groups include, cyclooctynyl, cyclononynyl, cyclodecynyl, 2-methylcyclooctynyl, and the like.

The terms "cycloalkylene" or "cycloalkylene group" mean a stable saturated aliphatic 3- to 15-membered monocyclic or polycyclic divalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkylene groups include cyclopentylene, and the like.

The terms "cycloalkenylene" or "cycloalkenylene group" mean a stable aliphatic 5- to 15-membered monocyclic or polycyclic divalent radical having at least one carbon-carbon double bond and consisting solely of carbon and hydrogen atoms which may comprise one or more fused or bridged ring(s), preferably a 5- to 7-membered monocyclic or 7- to 10-membered bicyclic ring. Unless otherwise specified, the cycloalkenylene ring may be attached at any carbon atom which results in a stable structure and, if substituted, may be substituted at any suitable carbon atom which results in a stable structure. Exemplary cycloalkenylene groups include cyclopentenylene, cyclohexenylene, cycloheptenylene, cyclooctenylene, cyclononenylene, cyclodecenylene, norbornenylene, 2-methylcyclopentenylene, 2-methylcyclooctenylene, and the like.

The terms "cycloalkynylene" or "cycloalkynylene group" mean a stable aliphatic 8- to 15-membered monocyclic or polycyclic divalent radical having at least one carbon-carbon triple bond and consisting solely of carbon and hydrogen atoms which may comprise one or more fused or bridged ring(s), preferably a 8- to 10-membered monocyclic or 12- to 15-membered bicyclic ring. Unless otherwise specified, the cycloalkynylene ring may be attached at any carbon atom which results in a stable structure and, if substituted, may be substituted at any suitable carbon atom which results in a stable structure. Exemplary cycloalkynylene groups include cyclooctynylene, cyclononynylene, cyclodecynylene, 2-methylcyclooctynylene, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, and the like.

The term "compounds of the invention", and equivalent expressions, are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 $R^5$, then such group is optionally substituted with up to two $R^5$ groups and $R^5$ at each occurrence is selected independently from the defined list of possible $R^5$. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

B. Salt, Prodrug, Derivative, and Solvate Terms and Conventions

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309–396; *Burger's Medicinal Chemistry and Drug Discovery*, 5th Ed., M. Wolff (ed.), John Wiley & Sons, 1995, particularly Vol. 1 and pp. 172–178 and pp. 949–982; *Pro-Drugs as Novel Delivery Systems*, T. Higuchi and V. Stella (eds.), Am. Chem. Soc., 1975; and *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1–19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (for example, a compound of Formula (I)) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "hydrate" means a solvate wherein the solvent molecule(s) is/are $H_2O$.

The compounds of the present invention as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

The term "isomer" means compounds having the same number and kind of atoms, and hence the same molecular weight, but differing with respect to the arrangement or configuration of the atoms in space. The term includes stereoisomers and geometric isomers.

The term "stereoisomer" means a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to optical isomerism, the invention contemplates stereoisomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure optical isomers, i.e., as individual enantiomers or diastereomers, or as stereoisomer-enriched mixtures. Individual stereoisomers of compounds are prepared by synthesis from optically active starting materials containing the desired chiral centers or by preparation of mixtures of enantiomeric products followed by separation, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of optical isomers that are non-superimposable mirror images of each other.

The terms "diastereoisomers" or "diastereomers" mean stereoisomers which are not mirror images of each other.

The terms "racemic mixture" or "racemate" mean a mixture containing equal parts of individual enantiomers.

The term "non-racemic mixture" means a mixture containing unequal parts of individual enantiomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the invention, the invention contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, *Advanced Organic Chemistry: Reactions, Mechanisms, and Structure,* 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H NMR, and $^{13}$C NMR.

Some of the compounds of the invention can exist in more than one tautomeric form. As mentioned above, the compounds of the invention include all such tautomers.

In general, all tautomeric forms and isomeric forms and mixtures, whether individual geometric isomers or optical isomers or racemic or non-racemic mixtures, of a chemical structure or compound is intended, unless the specific stereochemistry or isomeric form is specifically indicated in the compound name or structure.

D. Pharmaceutical Administration and Diagnostic and Treatment Terms and Conventions The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The term "modulate" means the ability of a compound to alter the function of the glucocorticoid receptor by, for example, binding to and stimulating or inhibiting the glucocorticoid receptor functional responses.

The term "modulator" in the context of describing compounds according to the invention means a compound that modulates the glucocorticoid receptor function. As such, modulators include, but are not limited to, agonists, partial agonists, antagonists, and partial antagonists.

The term "agonist" in the context of describing compounds according to the invention means a compound that, when bound to the glucocorticoid receptor, enhances or increases the glucocorticoid receptor function. As such, agonists include partial agonists and full agonists.

The term "full agonist" in the context of describing compounds according to the invention means a compound that evokes the maximal stimulatory response from the glucocorticoid receptor, even when there are spare (unoccupied) glucocorticoid receptors present.

The term "partial agonist" in the context of describing compounds according to the invention means a compound that is unable to evoke the maximal stimulatory response from the glucocorticoid receptor, even at concentrations sufficient to saturate the glucocorticoid receptors present.

The term "antagonist" in the context of describing compounds according to the invention means a compound that directly or indirectly inhibits or suppresses the glucocorticoid receptor function. As such, antagonists include partial antagonists and full antagonists.

The term "full antagonist" in the context of describing compounds according to the invention means a compound that evokes the maximal inhibitory response from the glucocorticoid receptor, even when there are spare (unoccupied) glucocorticoid receptors present.

The term "partial antagonist" in the context of describing compounds according to the invention means a compound that is unable to evoke the maximal inhibitory response from the glucocorticoid receptor, even at concentrations sufficient to saturate the glucocorticoid receptors present.

The terms "treating" or "treatment" mean the treatment of a disease-state in a patient, and include:

(i) preventing the disease-state from occurring in a patient, in particular, when such patient is genetically or otherwise predisposed to the disease-state but has not yet been diagnosed as having it;

(ii) inhibiting or ameliorating the disease-state in a patient, i.e., arresting or slowing its development; or (iii) relieving the disease-state in a patient, i.e., causing regression or cure of the disease-state.

General Synthetic Methods

The invention also provides processes for making compounds of Formula (I). In all schemes, unless specified otherwise, $R^1$ to $R^6$ in the formulas below shall have the meaning of $R^1$ to $R^6$ in the Formula (I) of the invention described hereinabove. Intermediates used in the preparation of compounds of the invention are either commercially available or readily prepared by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

Compounds of Formula (I) where $R^4$ is C=O may be prepared by the method outlined in Scheme I.

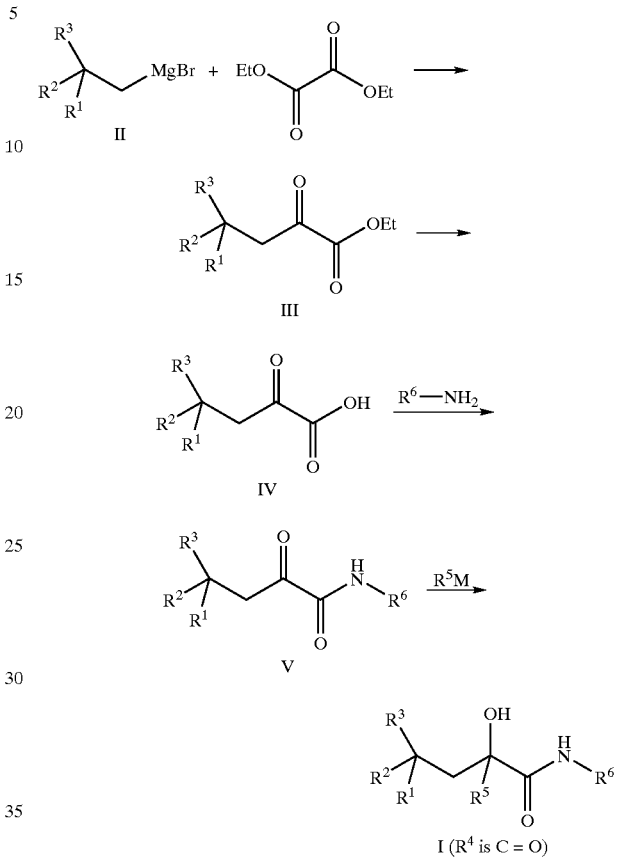

According to this method, one reacts an oxalate ester, preferably diethyl oxalate, with an alkylmagnesium halide, such as an alkylmagnesium bromide, that bears $R^1$, $R^2$, and $R^3$ (II). Such alkylmagnesium halides or Grignard reagents are well known in the art and are easily prepared by reacting the corresponding alkyl halide with magnesium metal in a suitable solvent, such as ether or THF, under anhydrous conditions. The resulting ketoester (III) is hydrolyzed, for example by refluxing with an aqueous base such as potassium hydroxide with a suitable co-solvent such as methanol. The resulting ketoacid (IV) may be coupled with an amine bearing $R^6$ under standard coupling conditions well-known in the art (see, for example, M. Bodanszky, *The Practice of Peptide Synthesis* (Springer-Verlag: 1984), which is hereby incorporated by reference in its entirety). For example, one may convert the carboxylic acid to an acid chloride with an activating agent such as thionyl chloride, in a suitable solvent such as dimethylacetamide, followed by reaction of the acid chloride with $R^6NH_2$. The resulting ketoamide (V) is then reacted with a suitable organometallic reagent $R^5M$ where M is Li or MgX, and X is Cl, Br, or I, that is, an organolithium reagent or alkylmagnesium halide bearing $R^5$, to produce the desired compound of Formula (I) where $R^4$ is C=O.

An alternative approach that may be used to obtain the ketoester intermediate used in the scheme above is outlined in Scheme II.

Scheme II

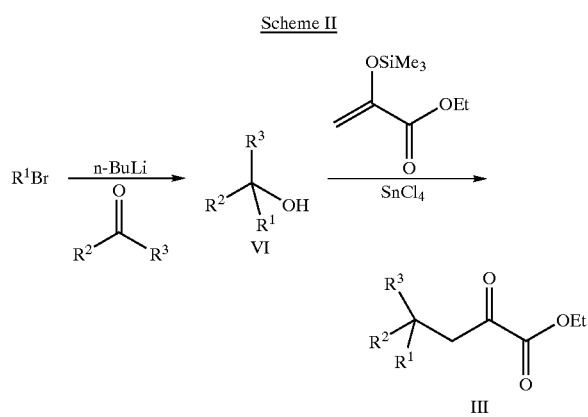

According to this method, an aryl bromide (R¹Br) is reacted with an organometallic reagent such as n-butyllithium in a suitable solvent such as THF, preferably at about −78° C. The resulting anion is reacted with a ketone bearing R² and R³ to give an alcohol bearing R¹, R², and R³ (VI). This alcohol is reacted with a silyl enol ether derived from ethyl pyruvate, in the presence of a Lewis acid such as stannic chloride, in a suitable solvent such as methylene chloride at about −78° C. to −50° C. to provide the ketoester intermediate bearing R¹, R², and R³ (III). The preparation of silyl enol ethers is known in the art, for example ethyl pyruvate may be reacted with trimethylsilyl trifluoromethylsulfonate in a suitable solvent such as methylene chloride.

Compounds of Formula (I) where $R^4$ is $CH_2$ may be prepared by the method outlined in Scheme III.

Scheme III

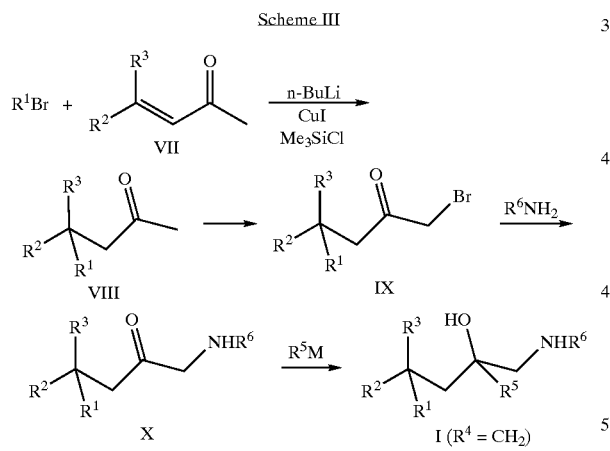

According to this method, the aryl or heteroaryl bromide R¹Br is treated with an organometallic reagent such as n-butyl lithium in a suitable solvent such as THF at about −78° C. The resulting anion undergoes addition to a methyl vinyl ketone bearing R² and R³ (VII), for example, by treating with cuprous iodide in dimethylsulfide followed by chlorotrimethyl silane and then the ketone. The resulting methyl ketone (VIII) is brominated by treating with a suitable brominating agent such as benzyltrimethylammonium tribromide in a suitable solvent such as methylene chloride. The resulting bromoketone (IX) is reacted with an amine bearing R⁶ in a suitable solvent such as acetonitrile at a temperature of from about ambient to about the reflux temperature of the solvent, to provide the corresponding aminoketone (X). Treatment of the resulting aminoketone (X) with a suitable organometallic reagent R⁵M where M is Li or MgX, and X is Cl, Br, or I, that is, an organolithium reagent or alkylmagnesium halide bearing R⁵, produces the desired compound of Formula (I) where $R^4$ is $CH_2$.

In order that this invention be more fully understood, the following examples are set forth. These examples are for the purpose of illustrating embodiments of this invention, and are not to be construed as limiting the scope of the invention in any way since, as recognized by one skilled in the art, particular reagents or conditions could be modified as needed for individual compounds. Starting materials used are either commercially available or easily prepared from commercially available materials by those skilled in the art.

EXPERIMENTAL EXAMPLES

Example 1

Synthesis of 2-benzyl-2-hydroxy-4-methyl-4-phenylpentanoic acid (1-oxo-1,3-dihydroisobenzofuran-5-yl)amide

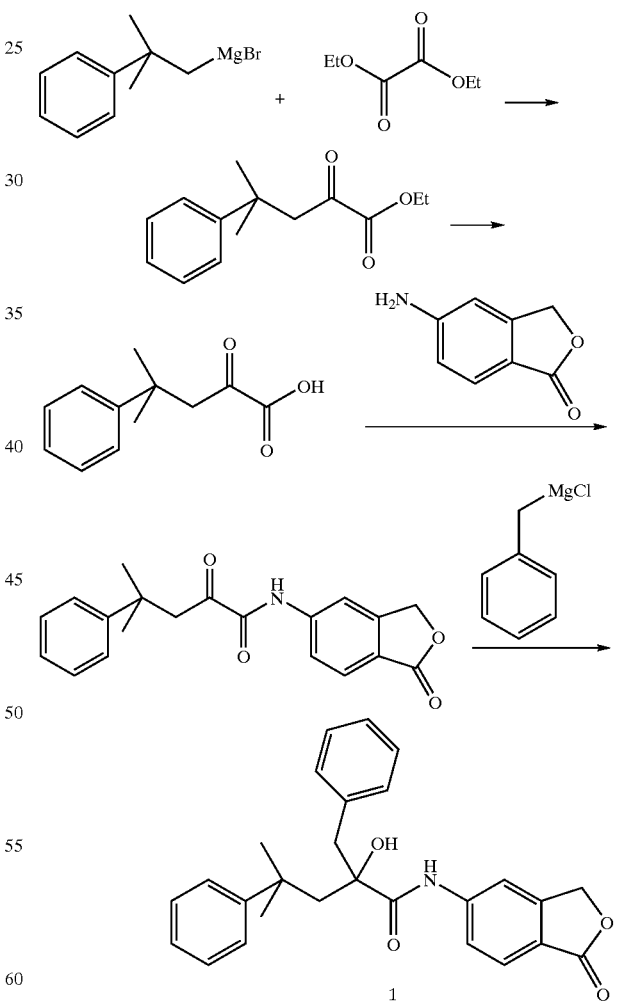

2-Phenyl-2,2-dimethylethylmagnesium bromide (10 mmol, 20 mL of 0.5 M solution in diethyl ether) was added to solution of diethyl oxalate (1.5 g, 10.5 mmol) in anhydrous THF (20 mL) cooled to −78° C. and maintained under argon. After 1 hour, TLC in hexanes-EtOAc (7:1) indicated most of the diethyl oxalate had been consumed. The reaction mixture was quenched with a saturated solution of ammonium chloride and extracted with three 50 mL portions of EtOAc. The combined extracts were dried over anhydrous sodium sulfate and concentrated in vacuo to give a light brown, thick oil which was purified by flash column chromatography over silica gel eluting with 5% EtOAc in hexanes to yield 4-methyl-2-oxo-4-phenylpentanoic acid ethyl ester as a light yellow oil (1.1 g, 51%).

Potassium hydroxide (1.6 g in 5 mL of water, 28.2 mmol) was added to a solution of the above ketoester (1.1 g, 4.7 mmol) in MeOH (15 mL) and the mixture was refluxed for 1 hour. The reaction mixture was cooled to room temperature, concentrated in vacuo, acidified with dilute HCl, extracted with three 30 mL portions of methylene chloride, dried over anhydrous sodium sulfate, and concentrated in vacuo to give 4-methyl-2-oxo-4-phenylpentanoic acid (0.9 g, 93%).

To a solution of the above ketoacid (0.1 g, 0.48 mmol) in dimethylacetamide (5 mL), cooled to −8° C. under argon, was added thionyl chloride (0.04 mL, 0.52 mmol). After 20 minutes stirring at −4° C., the 5-aminophthalide was added and the mixture was stirred at room temperature for 1.5 hours. The reaction mixture was treated with water (50 mL) and extracted with three 50 mL portions of EtOAc. The combined extracts were dried over anhydrous sodium sulfate and concentrated in vacuo to give a light brown thick oil which was purified by flash column chromatography over silica gel eluting with 25% EtOAc in hexanes to yield 4-methyl-2-oxo-4-phenylpentanoic acid (1-oxo-1,3-dihydroisobenzofuran-5-yl)amide (60%) as a light yellow solid, m.p. 132° C.–134° C.

To a solution of the above ketoamide (80 mg, 0.24 mmol) in dry THF (5 mL) and cooled on ice, benzylmagnesium chloride (0.26 mL of 1 M solution in ether, 0.26 mmol) was added. The reaction was stirred at room temperature for 5 hours and then quenched with a saturated solution of ammonium chloride and extracted with three 10 mL portions of EtOAc. The combined extracts were dried over anhydrous sodium sulfate and concentrated in vacuo to give a light brown, thick oil which was purified by preparative TLC over silica gel eluting with hexanes-EtOAc (1:1) to give the title compound as a light yellow solid (31 mg).

Example 2

Synthesis of 4-(5-fluoro-2-methoxyphenyl)-4-methyl-2-oxopentanoic acid ethyl ester

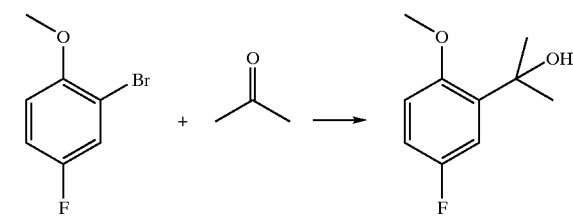

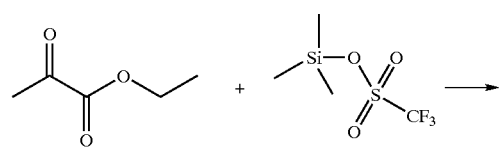

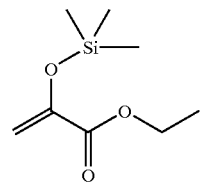

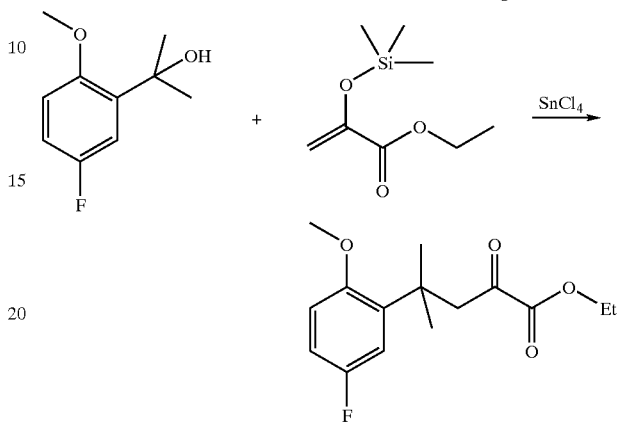

To a stirred solution of 2-bromo-4-fluoro anisole (4.1 g, 20 mmol) in anhydrous THF (40 mL) cooled to −78° C. and maintained under an atmosphere of argon was added n-butyl lithium (8.8 mL of 2.5 M solution in hexanes, 22 mmol). After stirring at −78° C. for 45 minutes, the reaction mixture was treated with anhydrous acetone (5 mL). After 15 minutes, the reaction mixture was quenched with a saturated solution of ammonium chloride and extracted with three 50 mL portions of methylene chloride. Combined extracts were washed with three 25 mL portions of water, dried over anhydrous sodium sulfate, and the solvent was evaporated to give 2-(5-fluoro-2-methoxyphenyl)propan-2-ol as a light brown thick oil (85% yield) which solidified on standing. The crude product was used for the next reaction without further purification.

A solution of trimethylsilyl trifluoromethylsulfonate (9.52 mL, 52.5 mmol) in anhydrous methylene chloride (10 mL) was added to a stirred ice-cooled solution of ethyl pyruvate (5.56 mL, 50 mmol) and diisopropylethyl amine (9.6 mL, 55 mmol) in anhydrous methylene chloride (100 mL) over a period of 15 minutes. The reaction was stirred on ice for 1.5 hours and then at room temperature for 3 hours. The solvent was evaporated at room temperature and the residue treated with anhydrous pentane (200 mL) and cooled in ice. The precipitated solid was filtered off. The filtrate was collected and the pentane evaporated to give 2-trimethylsilanyloxyacrylic acid ethyl ester as a light brown liquid (90% yield). The crude product was used for the next reaction without further purification.

Stannic chloride (5 mL of 1 M solution in methylene chloride, 5 mmol) was added to a stirred solution of 2-(5-fluoro-2-methoxyphenyl)propan-2-ol (2.85 g, 15.5 mmol) and 2-trimethylsilanyloxy-acrylic acid ethyl ester (23.3 mmol, 4.37 g) in anhydrous methylene chloride (45 mL) cooled to −78° C. After 7 hours with the temperature maintained in the range of −78° C. to −50° C., TLC in hexanes-EtOAc (9:1) indicated that a significant amount of starting material remained. More stannic chloride (5 mL of 1 M solution in methylene chloride, 5 mmol) was added with the temperature around −50° C. After 2 hours, all the starting material had been consumed. The reaction mixture was treated with water (100 mL), stirred for 15 minutes and diluted with methylene chloride. The methylene chloride layer was separated, washed with two 50 mL portions of the water, dried over anhydrous sodium sulfate, and concentrated in vacuo to give a light brown oil. The crude product was purified by flash column chromatography over silica gel eluting with 10% EtOAc in hexanes and a fraction corresponding to $R_f$=0.28 was collected to give the title compound (35%) as a light brown oil.

This ester was converted to the ketoamide by hydrolysis and coupling to the desired amine and then to the desired hydroxy amide by reaction with the appropriate Grignard reagent by procedures described in Example 1.

Example 3

Synthesis of 2-benzyl-4-(5-fluoro-2-hydroxyphenyl)-2-hydroxy-4-methylpentanoic acid (1-oxo-1,3-dihydroisobenzofuran-5-yl)amide

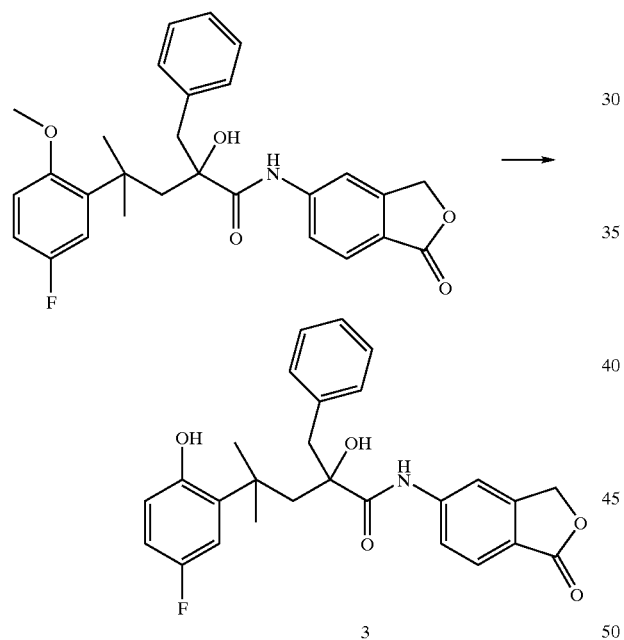

To a stirred solution of 2-benzyl-4-(5-fluoro-2-methoxyphenyl)-2-hydroxy-4-methylpentanoic acid (1-oxo-1,3-dihydroisobenzofuran-5-yl)amide (25 mg, 0.053 mmol) in anhydrous methylene chloride (1 mL) and cooled in ice was added boron tribromide (0.3 mL of 1 M solution in methylene chloride, 0.3 mmol). The reaction was stirred at room temperature for 3 hours and then quenched with water (5 mL). Methylene chloride (25 mL) was added, the organic layer separated, dried over anhydrous sodium sulfate and concentrated in vacuo to give a light brown oil which was purified by preparative TLC eluting with methylene chloride-EtOAc (9:1) to give the title compound as a light, cream colored solid.

Example 4

Synthesis of 5-[2-benzyl-4-(5-fluoro-2-methoxyphenyl)-2-hydroxy-4-methylpentylamino]-3H-isobenzofuran-1-one

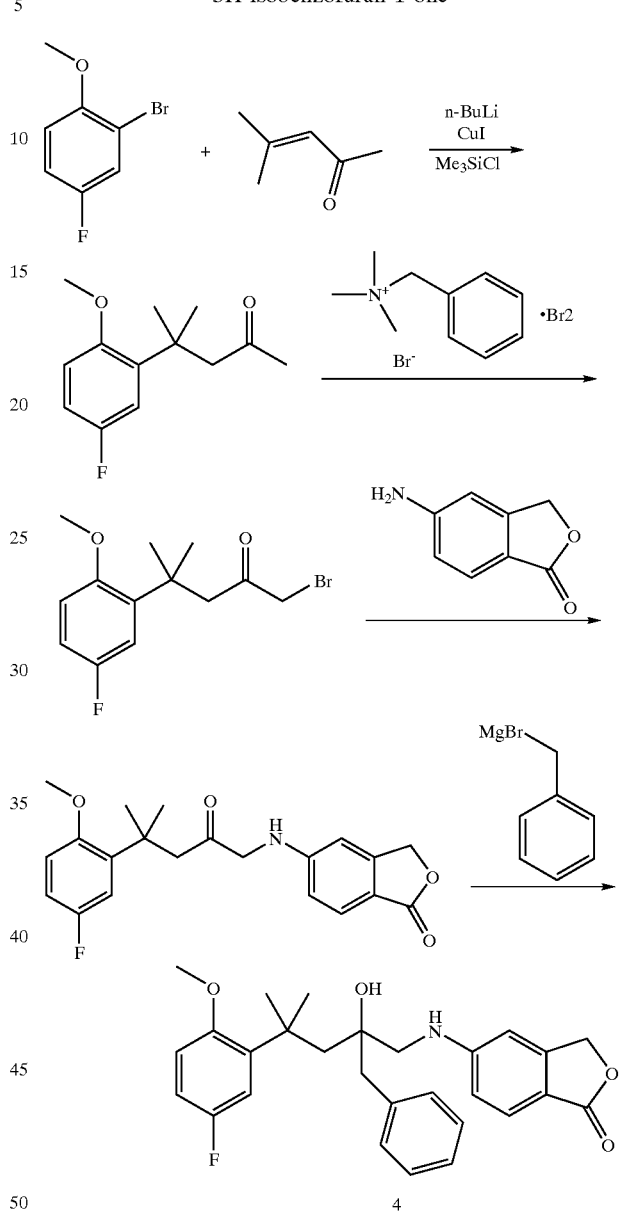

To a stirred solution of 2-bromo-4-fluoro anisole (3.24 mL, 25 mmol) in anhydrous THF (40 mL) cooled to —78° C. and maintained under argon was added n-butyl lithium (17.2 mL of 1.6 M solution in hexanes, 27.5 mmol). After stirring at −78° C. for 45 minutes, the reaction mixture was treated with a solution of cuprous iodide in dimethyl sulfide (4.76 g in 15 mL, 25 mmol) and stirred for 15 minutes at −78° C. Then chlorotrimethylsilane (6.4 mL, 50 mmol) was added, followed by a solution of mesityl oxide (2.9 mL, 25 mmol) in anhydrous THF (5 mL). The reaction was stirred at −78° C. to −60° C. for 4 hours and then quenched with a saturated solution of ammonium chloride and extracted with three 50 mL portions of methylene chloride. The combined extracts were washed with three 25 mL portions of water, dried over anhydrous sodium sulfate, and concentrated in vacuo to give 4-(5-fluoro-2-methoxyphenyl)-4-methylpentan-2-one as a light brown liquid (85% yield) which was used in the next reaction without further purification.

To a stirred solution of the above ketone (1.34 g, 6 mmol) in methylene chloride (35 mL) and MeOH (5 mL), benzyltrimethylammonium tribromide (2.57 g, 6.6 mmol) was added at ambient temperature. After 30 minutes, TLC (hexanes-EtOAc (9:1)) showed complete disappearance of the starting material. The reaction mixture was diluted with methylene chloride (50 mL), washed with two 50 mL portions of water, dried over anhydrous sodium sulfate, and concentrated in vacuo to give 1-bromo-4-(5-fluoro-2-methoxyphenyl)-4-methylpentan-2-one as a light brown liquid (80%) which was used for the next reaction without further purification.

A solution of the above bromoketone (0.912 g, 3 mmol), the isobenzofuranone amine (0.447 g, 3 mmol) and diisopropylethylamine (4.5 mmol 0.743 mL) in acetonitrile (5 mL) was heated in an oil bath maintained at 85° C. for 12 hours. After cooling to room temperature, solvent was evaporated and the crude material was purified by column chromatography over silica gel, eluting with methylene chloride-EtOAc (95:5). The fraction corresponding to $R_f$=0.5 was collected to give 5-[4-(5-fluoro-2-methoxyphenyl)-4-methyl-2-oxopentylamino]-3H-isobenzofuran-1-one as a light brown liquid which solidified on standing (40%).

To a solution of the above ketone (74 mg, 0.2 mmol) in dry THF (1 mL) and cooled on ice, benzylmagnesium bromide (0.3 mL of 2 M solution in THF, 0.6 mmol) was added. The reaction was stirred at room temperature for 3 hours, and then quenched with ammonium chloride and extracted with methylene chloride (5 mL). The organic fraction was collected and purified by preparative TLC eluting with hexanes-EtOAc (55:45) to give the title compound as a light cream colored solid.

The following compounds were also prepared by methods analogous to those described in the above examples:
2-Benzyl-2-hydroxy-4-methyl-4-phenylpentanoic acid (1-oxo-1,3-dihydroisobenzofuran-5-yl)amide;
2-Hydroxy-4-methyl-2,4-diphenylpentanoic acid (1-oxo-1,3-dihydroisobenzofuran-5-yl)amide;
2-Hydroxy-4-methyl-2-phenethyl-4-phenylpentanoic acid (1-oxo-1,3-dihydroisobenzofuran-5-yl)amide;
2-Hydroxy-2-(3-methoxybenzyl)-4-methyl-4-phenylpentanoic acid (1-oxo-1,3-dihydroisobenzofuran-5-yl)amide;
2-Hydroxy-2-(4-methoxybenzyl)-4-methyl-4-phenylpentanoic acid (1-oxo-1,3-dihydroisobenzofuran-5-yl)amide;
2-Hydroxy-2-[2-(4-methoxyphenyl)ethyl]-4-methyl-4-phenylpentanoic acid (1-oxo-1,3-dihydroisobenzofuran-5-yl)amide;
2-Cyclohexylmethyl-2-hydroxy-4-methyl-4-phenylpentanoic acid (1-oxo-1,3-dihydroisobenzofuran-5-yl)amide;
2-(4-tert-Butylbenzyl)-2-hydroxy-4-methyl-4-phenylpentanoic acid (1-oxo-1,3-dihydroisobenzofuran-5-yl)amide;
2-Biphenyl-4-ylmethyl-2-hydroxy-4-methyl-4-phenylpentanoic acid (1-oxo-1,3-dihydroisobenzofuran-5-yl)amide;
2-Hydroxy-4-methyl-2-naphthalen-2-ylmethyl-4-phenylpentanoic acid (1-oxo-1,3-dihydroisobenzofuran-5-yl)amide;
2-Hydroxy-2-(3-hydroxybenzyl)-4-methyl-4-phenylpentanoic acid (1-oxo-1,3-dihydroisobenzofuran-5-yl)amide;
2-Hydroxy-4-methyl-2-(2-methyl-2-phenylpropyl)-4-phenylpentanoic acid (1-oxo-1,3-dihydroisobenzofuran-5-yl)amide;
2-Benzyl-4-(5-fluoro-2-methoxyphenyl)-2-hydroxy-4-methylpentanoic acid (1-oxo-1,3-dihydroisobenzofuran-5-yl)amide;
2-Cyclohexylmethyl-4-(5-fluoro-2-methoxyphenyl)-2-hydroxy-4-methylpentanoic acid (1-oxo-1,3-dihydroisobenzofuran-5-yl)amide;
2-Benzyl-4-(5-fluoro-2-hydroxyphenyl)-2-hydroxy-4-methylpentanoic acid (1-oxo-1,3-dihydroisobenzofuran-5-yl)amide;
2-Cyclohexylmethyl-4-(5-fluoro-2-hydroxyphenyl)-2-hydroxy-4-methylpentanoic acid (1-oxo-1,3-dihydroisobenzofuran-5-yl)amide;
4-(5-Fluoro-2-hydroxyphenyl)-2-hydroxy-4-methyl-2-(2-methyl-2-phenylpropyl)pentanoic acid (1-oxo-1,3-dihydroisobenzofuran-5-yl)amide;
2-(2-Chloro-6-fluorobenzyl)-4-(5-fluoro-2-methoxyphenyl)-2-hydroxy-4-methylpentanoic acid (1-oxo-1,3-dihydroisobenzofuran-5-yl)amide;
2-(3-Fluorobenzyl)-4-(5-fluoro-2-methoxyphenyl)-2-hydroxy-4-methylpentanoic acid (1-oxo-1,3-dihydroisobenzofuran-5-yl)amide;
2-(2-Fluorobenzyl)-4-(5-fluoro-2-methoxyphenyl)-2-hydroxy-4-methylpentanoic acid (1-oxo-1,3-dihydroisobenzofuran-5-yl)amide;
2-(3,4-Difluorobenzyl)-4-(5-fluoro-2-methoxyphenyl)-2-hydroxy-4-methylpentanoic acid (1-oxo-1,3-dihydroisobenzofuran-5-yl)amide;
2-(2-Chloro-6-fluorobenzyl)-4-(5-fluoro-2-hydroxyphenyl)-2-hydroxy-4-methylpentanoic acid (1-oxo-1,3-dihydroisobenzofuran-5-yl)amide;
2-(3-Fluorobenzyl)-4-(5-fluoro-2-hydroxyphenyl)-2-hydroxy-4-methylpentanoic acid (1-oxo-1,3-dihydroisobenzofuran-5-yl)amide;
2-(2-Fluorobenzyl)-4-(5-fluoro-2-hydroxyphenyl)-2-hydroxy-4-methylpentanoic acid (1-oxo-1,3-dihydroisobenzofuran-5-yl)amide;
2-(3,4-Difluorobenzyl)-4-(5-fluoro-2-hydroxyphenyl)-2-hydroxy-4-methylpentanoic acid (1-oxo-1,3-dihydroisobenzofuran-5-yl)amide;
2-(4-Fluorobenzyl)-4-(5-fluoro-2-methoxyphenyl)-2-hydroxy-4-methylpentanoic acid (1-oxo-1,3-dihydroisobenzofuran-5-yl)amide;
4-(5-Fluoro-2-methoxyphenyl)-2-hydroxy-4-methyl-2-(3-methylbenzyl)pentanoic acid (1-oxo-1,3-dihydroisobenzofuran-5-yl)amide;
2-(4-Fluorobenzyl)-4-(5-fluoro-2-hydroxyphenyl)-2-hydroxy-4-methylpentanoic acid (1-oxo-1,3-dihydroisobenzofuran-5-yl)amide;
4-(5-Fluoro-2-hydroxyphenyl)-2-hydroxy-4-methyl-2-(3-methylbenzyl)pentanoic acid (1-oxo-1,3-dihydroisobenzofuran-5-yl)amide;
2-(3,5-Difluorophenyl)-4-(5-fluoro-2-hydroxyphenyl)-2-hydroxy-4-methylpentanoic acid (1-oxo-1,3-dihydroisobenzofuran-5-yl)amide;
2-Benzyl-4-(5-fluoro-2-methoxyphenyl)-2-hydroxy-4-methylpentanoic acid (4-methyl-1-oxo-1H-benzo[d][1,2]oxazin-6-yl)amide;
2-Benzyl-4-(5-fluoro-2-hydroxyphenyl)-2-hydroxy-4-methylpentanoic acid (4-methyl-1-oxo-1H-benzo[d][1,2]oxazin-6-yl)amide;
2-Cyclohexylmethyl-4-(5-fluoro-2-methoxyphenyl)-2-hydroxy-4-methylpentanoic acid (4-methyl-1-oxo-1H-benzo[d][1,2]oxazin-6-yl)amide;
2-Benzyl-4-(5-fluoro-2-methoxyphenyl)-2-hydroxy-4-methylpentanoic acid (3,5-dichlorophenyl)amide;

4-(5-Fluoro-2-methoxyphenyl)-2-hydroxy-4-methyl-2-(2-methylbenzyl)pentanoic acid (1-oxo-1,3-dihydroisobenzofuran-5-yl)amide;

2-(3,5-Dimethylbenzyl)-4-(5-fluoro-2-methoxyphenyl)-2-hydroxy-4-methylpentanoic acid (1-oxo-1,3-dihydroisobenzofuran-5-yl)amide;

2-(2,5-Difluorobenzyl)-4-(5-fluoro-2-methoxyphenyl)-2-hydroxy-4-methylpentanoic acid (1-oxo-1,3-dihydroisobenzofuran-5-yl)amide;

2-(2,5-Difluorobenzyl)-4-(5-fluoro-2-hydroxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-4-methyl-2-(2-methylbenzyl)pentanoic acid (1-oxo-1,3-dihydroisobenzofuran-5-yl)amide;

2-(3,5-Dimethylbenzyl)-4-(5-fluoro-2-hydroxyphenyl)-2-hydroxy-4-methylpentanoic acid (1-oxo-1,3-dihydroisobenzofuran-5-yl)amide;

2-Cyclohexylmethyl-4-(5-fluoro-2-methoxyphenyl)-2-hydroxy-4-methylpentanoic acid (3,5-dichlorophenyl)amide;

2-Cyclohexylmethyl-4-(5-fluoro-2-hydroxyphenyl)-2-hydroxy-4-methylpentanoic acid (4-methyl-1-oxo-1H-benzo[d][1,2]oxazin-6-yl)amide;

2-Benzyl-4-(5-fluoro-2-hydroxyphenyl)-2-hydroxy-4-methylpentanoic acid (3,5-dichlorophenyl)amide;

2-Cyclohexylmethyl-4-(5-fluoro-2-hydroxyphenyl)-2-hydroxy-4-methylpentanoic acid (3,5-dichlorophenyl)amide;

2-Benzyl-4-(5-fluoro-2-methoxyphenyl)-2-hydroxy-4-methylpentanoic acid phenylamide;

2-Cyclohexylmethyl-4-(5-fluoro-2-methoxyphenyl)-2-hydroxy-4-methylpentanoic acid phenylamide;

2-(3-Chlorobenzyl)-4-(5-fluoro-2-hydroxyphenyl)-2-hydroxy-4-methylpentanoic acid (1-oxo-1,3-dihydroisobenzofuran-5-yl)amide;

4-(5-Fluoro-2-methoxyphenyl)-2-hydroxy-2-[2-(4-methoxyphenyl)ethyl]-4-methylpentanoic acid (1-oxo-1,3-dihydroisobenzofuran-5-yl)amide;

4-(5-Fluoro-2-methoxyphenyl)-2-hydroxy-2-(2-methoxybenzyl)-4-methylpentanoic acid (1-oxo-1,3-dihydroisobenzofuran-5-yl)amide;

2-Benzyl-4-(5-fluoro-2-hydroxyphenyl)-2-hydroxy-4-methylpentanoic acid phenylamide;

2-Cyclohexylmethyl-4-(5-fluoro-2-hydroxyphenyl)-2-hydroxy-4-methylpentanoic acid phenylamide;

4-(5-Fluoro-2-methoxyphenyl)-2-hydroxy-4-methyl-2-phenethylpentanoic acid (1-oxo-1,3-dihydroisobenzofuran-5-yl)amide;

2-(2-Chlorobenzyl)-4-(5-fluoro-2-methoxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-4-methyl-2-phenethylpentanoic acid (1-oxo-1,3-dihydroisobenzofuran-5-yl)amide;

4-(5-Fluoro-2-hydroxyphenyl)-2-hydroxy-2-[2-(4-hydroxyphenyl)ethyl]-4-methylpentanoic acid (1-oxo-1,3-dihydroisobenzofuran-5-yl)amide;

2-(2-Chlorobenzyl)-4-(5-fluoro-2-hydroxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-2-(2-hydroxybenzyl)-4-methylpentanoic acid (1-oxo-1,3-dihydroisobenzofuran-5-yl)amide;

2-(2-Bromobenzyl)-4-(5-fluoro-2-methoxyphenyl)-2-hydroxy-4-methylpentanoic acid (1-oxo-1,3-dihydroisobenzofuran-5-yl)amide;

2-(2-Bromobenzyl)-4-(5-fluoro-2-hydroxyphenyl)-2-hydroxy-4-methylpentanoic acid (1-oxo-1,3-dihydroisobenzofuran-5-yl)amide;

2-Benzyl-4-(5-fluoro-2-methoxyphenyl)-2-hydroxy-4-methylpentanoic acid (3,5-dimethylphenyl)amide;

2-Cyclohexylmethyl-4-(5-fluoro-2-methoxyphenyl)-2-hydroxy-4-methylpentanoic acid (3,5-dimethylphenyl)amide;

2-Benzyl-4-(5-fluoro-2-methoxyphenyl)-2-hydroxy-4-methylpentanoic acid (3,5-bis-trifluoromethylphenyl)amide;

2-Cyclohexylmethyl-4-(5-fluoro-2-methoxyphenyl)-2-hydroxy-4-methylpentanoic acid (3,5-bis-trifluoromethylphenyl)amide;

2-Benzyl-4-(5-fluoro-2-methoxyphenyl)-2-hydroxy-4-methylpentanoic acid (3,5-dimethoxyphenyl)amide;

2-Cyclohexylmethyl-4-(5-fluoro-2-methoxyphenyl)-2-hydroxy-4-methylpentanoic acid (3,5-dimethoxyphenyl)amide;

2-Benzyl-4-(5-fluoro-2-hydroxyphenyl)-2-hydroxy-4-methylpentanoic acid (3,5-dimethylphenyl)amide;

2-Cyclohexylmethyl-4-(5-fluoro-2-hydroxyphenyl)-2-hydroxy-4-methylpentanoic acid (3,5-dimethylphenyl)amide;

2-Benzyl-4-(5-fluoro-2-hydroxyphenyl)-2-hydroxy-4-methylpentanoic acid (3,5-bis-trifluoromethylphenyl)amide;

2-Cyclohexylmethyl-4-(5-fluoro-2-hydroxyphenyl)-2-hydroxy-4-methylpentanoic acid (3,5-bis-trifluoromethylphenyl)amide;

2-Benzyl-4-(5-fluoro-2-hydroxyphenyl)-2-hydroxy-4-methylpentanoic acid (3,5-dihydroxyphenyl)amide;

2-Cyclohexylmethyl-4-(5-fluoro-2-hydroxyphenyl)-2-hydroxy-4-methylpentanoic acid (3,5-dihydroxyphenyl)amide;

2-(5-Fluoro-2-methoxybenzyl)-2-hydroxy-4-methyl-4-phenylpentanoic acid (1-oxo-1,3-dihydroisobenzofuran-5-yl)amide;

2-(5-Fluoro-2-hydroxybenzyl)-2-hydroxy-4-methyl-4-phenylpentanoic acid (1-oxo-1,3-dihydroisobenzofuran-5-yl)amide;

2-(5-Fluoro-2-methoxybenzyl)-4-(5-fluoro-2-methoxyphenyl)-2-hydroxy-4-methylpentanoic acid (1-oxo-1,3-dihydroisobenzofuran-5-yl)amide;

2-(5-Fluoro-2-hydroxybenzyl)-4-(5-fluoro-2-hydroxyphenyl)-2-hydroxy-4-methylpentanoic acid (1-oxo-1,3-dihydroisobenzofuran-5-yl)amide;

2-(3,5-Dimethoxybenzyl)-2-hydroxy-4-methyl-4-phenylpentanoic acid (1-oxo-1,3-dihydroisobenzofuran-5-yl)amide;

2-(3,5-Dihydroxybenzyl)-2-hydroxy-4-methyl-4-phenylpentanoic acid (1-oxo-1,3-dihydroisobenzofuran-5-yl)amide;

2-Hydroxy-2-(2-methoxybenzyl)-4-methyl-4-phenylpentanoic acid (1-oxo-1,3-dihydroisobenzofuran-5-yl)amide;

2-Hydroxy-2-(2-hydroxybenzyl)-4-methyl-4-phenylpentanoic acid (1-oxo-1,3-dihydroisobenzofuran-5-yl)amide;

2-Hydroxy-2-[2-(4-hydroxyphenyl)ethyl]-4-methyl-4-phenylpentanoic acid (1-oxo-1,3-dihydroisobenzofuran-5-yl)amide;

5-[2-Benzyl-4-(5-fluoro-2-methoxyphenyl)-2-hydroxy-4-methylpentylamino]-3H-isobenzofuran-1-one;

2-Benzyl-4-(5-fluoro-2-methoxyphenyl)-2-hydroxy-4-methylpentanoic acid (4-cyano-3-trifluoromethylphenyl)amide;

2-Benzyl-4-(5-fluoro-2-hydroxyphenyl)-2-hydroxy-4-methylpentanoic acid (4-cyano-3-trifluoromethylphenyl)amide;
4-(5-Fluoro-2-methoxyphenyl)-2-hydroxy-4-methyl-2-(1-phenylvinyl)pentanoic acid (1-oxo-1,3-dihydroisobenzofuran-5-yl)amide;
2-Hydroxy-4-methyl-4-phenyl-2-pyridin-2-ylmethylpentanoic acid (1-oxo-1,3-dihydroisobenzofuran-5-yl)amide;
4-(5-Fluoro-2-methoxyphenyl)-2-hydroxy-4-methyl-2-(1-phenylethyl)pentanoic acid (1-oxo-1,3-dihydroisobenzofuran-5-yl)amide;
4-(5-Fluoro-2-hydroxyphenyl)-2-hydroxy-4-methyl-2-(1-phenylethyl)pentanoic acid (1-oxo-1,3-dihydroisobenzofuran-5-yl)amide;
4-(5-Fluoro-2-hydroxyphenyl)-2-hydroxy-4-methyl-2-(1-phenylethyl)pentanoic acid (1-oxo-1,3-dihydroisobenzofuran-5-yl)amide;
2-Benzyl-2-hydroxy-4-methyl-4-phenylpentanoic acid (4-methyl-1-oxo-1H-benzo[d][1,2]oxazin-6-yl)amide;
2-Cyclohexylmethyl-2-hydroxy-4-methyl-4-phenylpentanoic acid (4-methyl-1-oxo-1H-benzo[d][1,2]oxazin-6-yl)amide;
2-Cyclohexylmethyl-4-(5-fluoro-2-methoxyphenyl)-2-hydroxy-4-methylpentanoic acid (4-cyano-3-trifluoromethylphenyl)amide;
2-Cyclopentyl-4-(5-fluoro-2-methoxyphenyl)-2-hydroxy-4-methylpentanoic acid (1-oxo-1,3-dihydroisobenzofuran-5-yl)amide;
2-Cyclopentyl-4-(5-fluoro-2-hydroxyphenyl)-2-hydroxy-4-methylpentanoic acid (1-oxo-1,3-dihydroisobenzofuran-5-yl)amide;
2-Cyclopentylmethyl-4-(5-fluoro-2-hydroxyphenyl)-2-hydroxy-4-methylpentanoic acid (1-oxo-1,3-dihydroisobenzofuran-5-yl)amide; and
2-Benzyl-2-hydroxy-N-(1-oxo-1,3-dihydroisobenzofuran-5-yl)-4-phenyl-butyramide.

The following compounds may also be prepared by methods analogous to those described in the above examples:

i: 2-benzyl-2-hydroxy-4-(2-methoxyphenyl)-4-methylpentanoic acid (1-oxo-1,3-dihydroisobenzofuran-5-yl)amide;
ii: 2-benzyl-2-hydroxy-4-(2-methoxyphenyl)-4-methylpentanoic acid (4-methyl-1-oxo-1H-benzo[d][1,2]oxazin-6-yl)amide;
iii: 2-cyclohexylmethyl-2-hydroxy-4-(2-methoxyphenyl)-4-methylpentanoic acid (1-oxo-1,3-dihydroisobenzofuran-5-yl)amide;
iv: 2-cyclohexylmethyl-2-hydroxy-4-(2-methoxyphenyl)-4-methylpentanoic acid (4-methyl-1-oxo-1H-benzo[d][1,2]oxazin-6-yl)amide;
v: 2-cyclopentylmethyl-2-hydroxy-4-(2-methoxyphenyl)-4-methylpentanoic acid (1-oxo-1,3-dihydroisobenzofuran-5-yl)amide;
vi: 2-cyclopentylmethyl-2-hydroxy-4-(2-methoxyphenyl)-4-methylpentanoic acid (4-methyl-1-oxo-1H-benzo[d][1,2]oxazin-6-yl)amide;
vii: 2-cyclopentyl-2-hydroxy-4-(2-methoxyphenyl)-4-methylpentanoic acid (1-oxo-1,3-dihydroisobenzofuran-5-yl)amide;
viii: 2-cyclopentyl-2-hydroxy-4-(2-methoxyphenyl)-4-methylpentanoic acid (4-methyl-1-oxo-1H-benzo[d][1,2]oxazin-6-yl)amide;
ix: 2-hydroxy-4-(2-methoxyphenyl)-4-methyl-2-phenethylpentanoic acid (1-oxo-1,3-dihydroisobenzofuran-5-yl)amide;
x: 2-hydroxy-4-(2-methoxyphenyl)-4-methyl-2-phenethylpentanoic acid (4-methyl-1-oxo-1H-benzo[d][1,2]oxazin-6-yl)amide;
xi: 2-(2-chlorobenzyl)-2-hydroxy-4-(2-methoxyphenyl)-4-methylpentanoic acid (1-oxo-1,3-dihydroisobenzofuran-5-yl)amide;
xii: 2-(2-chlorobenzyl)-2-hydroxy-4-(2-methoxyphenyl)-4-methylpentanoic acid (4-methyl-1-oxo-1H-benzo[d][1,2]oxazin-6-yl)amide;
xiii: 2-benzyl-4-(2,3-dihydro-benzofuran-7-yl)-2-hydroxy-4-methylpentanoic acid (1-oxo-1,3-dihydroisobenzofuran-5-yl)amide;
xiv: 2-benzyl-4-(2,3-dihydro-benzofuran-7-yl)-2-hydroxy-4-methylpentanoic acid (4-methyl-1-oxo-1H-benzo[d][1,2]oxazin-6-yl)amide;
xv: 2-cyclohexylmethyl-4-(2,3-dihydro-benzofuran-7-yl)-2-hydroxy-4-methylpentanoic acid (1-oxo-1,3-dihydroisobenzofuran-5-yl)amide;
xvi: 2-cyclohexylmethyl-4-(2,3-dihydro-benzofuran-7-yl)-2-hydroxy-4-methylpentanoic acid (4-methyl-1-oxo-1H-benzo[d][1,2]oxazin-6-yl)amide;
xvii: 2-cyclopentylmethyl-4-(2,3-dihydro-benzofuran-7-yl)-2-hydroxy-4-methylpentanoic acid (1-oxo-1,3-dihydroisobenzofuran-5-yl)amide;
xviii: 2-cyclopentylmethyl-4-(2,3-dihydro-benzofuran-7-yl)-2-hydroxy-4-methylpentanoic acid (4-methyl-1-oxo-1H-benzo[d][1,2]oxazin-6-yl)amide;
xix: 2-cyclopentyl-4-(2,3-dihydro-benzofuran-7-yl)-2-hydroxy-4-methylpentanoic acid (1-oxo-1,3-dihydroisobenzofuran-5-yl)amide;
xx: 2-cyclopentyl-4-(2,3-dihydro-benzofuran-7-yl)-2-hydroxy-4-methylpentanoic acid (4-methyl-1-oxo-1H-benzo[d][1,2]oxazin-6-yl)amide;
xxi: 4-(2,3-dihydro-benzofuran-7-yl)-2-hydroxy-4-methyl-2-phenethylpentanoic acid (1-oxo-1,3-dihydroisobenzofuran-5-yl)amide;
xxii: 4-(2,3-dihydro-benzofuran-7-yl)-2-hydroxy-4-methyl-2-phenethylpentanoic acid (4-methyl-1-oxo-1H-benzo[d][1,2]oxazin-6-yl)amide;
xxiii: 2-(2-chlorobenzyl)-4-(2,3-dihydro-benzofuran-7-yl)-2-hydroxy-4-methylpentanoic acid (1-oxo-1,3-dihydroisobenzofuran-5-yl)amide;
xxiv: 2-(2-chlorobenzyl)-4-(2,3-dihydro-benzofuran-7-yl)-2-hydroxy-4-methylpentanoic acid (4-methyl-1-oxo-1H-benzo[d][1,2]oxazin-6-yl)amide;
xxv: 4-benzofuran-7-yl-2-benzyl-2-hydroxy-4-methylpentanoic acid (1-oxo-1,3-dihydroisobenzofuran-5-yl)amide;
xxvi: 4-benzofuran-7-yl-2-benzyl-2-hydroxy-4-methylpentanoic acid (4-methyl-1-oxo-1H-benzo[d][1,2]oxazin-6-yl)amide;
xxvii: 4-benzofuran-7-yl-2-cyclohexylmethyl-2-hydroxy-4-methylpentanoic acid (1-oxo-1,3-dihydroisobenzofuran-5-yl)amide;
xxviii: 4-benzofuran-7-yl-2-cyclohexylmethyl-2-hydroxy-4-methylpentanoic acid (4-methyl-1-oxo-1H-benzo[d][1,2]oxazin-6-yl)amide;
xxix: 4-benzofuran-7-yl-2-cyclopentylmethyl-2-hydroxy-4-methylpentanoic acid (1-oxo-1,3-dihydroisobenzofuran-5-yl)amide;
xxx: 4-benzofuran-7-yl-2-cyclopentylmethyl-2-hydroxy-4-methylpentanoic acid (4-methyl-1-oxo-1H-benzo[d][1,2]oxazin-6-yl)amide;
xxxi: 4-benzofuran-7-yl-2-cyclopentyl-2-hydroxy-4-methylpentanoic acid (1-oxo-1,3-dihydroisobenzofuran-5-yl)amide;
xxxii: 4-benzofuran-7-yl-2-cyclopentyl-2-hydroxy-4-methylpentanoic acid (4-methyl-1-oxo-1H-benzo[d][1,2]oxazin-6-yl)amide;
xxxiii: 4-benzofuran-7-yl-2-hydroxy-4-methyl-2-phenethylpentanoic acid (1-oxo-1,3-dihydroisobenzofuran-5-yl)amide;

xxxiv: 4-benzofuran-7-yl-2-hydroxy-4-methyl-2-phenethylpentanoic acid (4-methyl-1-oxo-1H-benzo[d][1,2]oxazin-6-yl)amide;

xxxv: 4-benzofuran-7-yl-2-(2-chlorobenzyl)-2-hydroxy-4-methylpentanoic acid (1-oxo-1,3-dihydroisobenzofuran-5-yl)amide;

xxxvi: 4-benzofuran-7-yl-2-(2-chlorobenzyl)-2-hydroxy-4-methylpentanoic acid (4-methyl-1-oxo-1H-benzo[d][1,2]oxazin-6-yl)amide;

xxxvii: 2-benzyl-4-(5-chloro-2-methoxyphenyl)-2-hydroxy-4-methylpentanoic acid (1-oxo-1,3-dihydroisobenzofuran-5-yl)amide;

xxxviii: 2-benzyl-4-(5-chloro-2-methoxyphenyl)-2-hydroxy-4-methylpentanoic acid (4-methyl-1-oxo-1H-benzo[d][1,2]oxazin-6-yl)amide;

xxxix: 4-(5-chloro-2-methoxyphenyl)-2-cyclohexylmethyl-2-hydroxy-4-methylpentanoic acid (1-oxo-1,3-dihydroisobenzofuran-5-yl)amide;

xxxx: 4-(5-chloro-2-methoxyphenyl)-2-cyclohexylmethyl-2-hydroxy-4-methylpentanoic acid (4-methyl-1-oxo-1H-benzo[d][1,2]oxazin-6-yl)amide;

xxxxi: 4-(5-chloro-2-methoxyphenyl)-2-cyclopentylmethyl-2-hydroxy-4-methylpentanoic acid (1-oxo-1,3-dihydroisobenzofuran-5-yl)amide;

xxxxii: 4-(5-chloro-2-methoxyphenyl)-2-cyclopentylmethyl-2-hydroxy-4-methylpentanoic acid (4-methyl-1-oxo-1H-benzo[d][1,2]oxazin-6-yl)amide;

xxxxiii: 4-(5-chloro-2-methoxyphenyl)-2-cyclopentyl-2-hydroxy-4-methylpentanoic acid (1-oxo-1,3-dihydroisobenzofuran-5-yl)amide;

xxxxiv: 4-(5-chloro-2-methoxyphenyl)-2-cyclopentyl-2-hydroxy-4-methylpentanoic acid (4-methyl-1-oxo-1H-benzo[d][1,2]oxazin-6-yl)amide;

xxxxv: 4-(5-chloro-2-methoxyphenyl)-2-hydroxy-4-methyl-2-phenethylpentanoic acid (1-oxo-1,3-dihydroisobenzofuran-5-yl)amide;

xxxxvi: 4-(5-chloro-2-methoxyphenyl)-2-hydroxy-4-methyl-2-phenethylpentanoic acid (4-methyl-1-oxo-1H-benzo[d][1,2]oxazin-6-yl)amide;

xxxxvii: 2-(2-chlorobenzyl)-4-(5-chloro-2-methoxyphenyl)-2-hydroxy-4-methylpentanoic acid (1-oxo-1,3-dihydroisobenzofuran-5-yl)amide; and xxxxviii: 2-(2-chlorobenzyl)-4-(5-chloro-2-methoxyphenyl)-2-hydroxy-4-methylpentanoic acid (4-methyl-1-oxo-1H-benzo[d][1,2]oxazin-6-yl)amide.

Assessment of Biological Properties

Compounds of the invention were evaluated for binding to the steroid receptor by a fluorescence polarization competitive binding assay. Detailed descriptions for preparation of recombinant glucocorticoid receptor (GR) complex used in the assay is described in U.S. provisional application No. 60/291,877, filed May 18, 2001, and incorporated herein by reference in its entirety. Preparation of the tetramethyl rhodamine (TAMRA)-labeled dexamethasone probe was accomplished using a standard literature procedure (M. Pons et al., J. Steroid Biochem., 1985, 22, pp. 267–273).

A. Glucocorticoid Receptor Competitive Binding Assay

Step 1. Characterization of the Fluorescent Probe

The wavelengths for maximum excitation and emission of the fluorescent probe should first be measured. An example of such a probe is rhodamine (TAMRA)-labeled dexamethasone.

The affinity of the probe for the steroid receptor was then determined in a titration experiment. The fluorescence polarization value of the probe in assay buffer was measured on an SLM-8100 fluorometer using the excitation and emission maximum values described above. Aliquots of expression vector lysate were added and fluorescence polarization was measured after each addition until no further change in polarization value was observed. Non-linear least squares regression analysis was used to calculate the dissociation constant of the probe from the polarization values obtained for lysate binding to the probe.

Step 2. Screening for Inhibitors of Probe Binding

This assay uses fluorescence polarization (FP) to quantitate the ability of test compounds to compete with tetramethyl rhodamine (TAMRA)-labeled dexamethasone for binding to a human glucocorticoid receptor (GR) complex prepared from an insect expression system. The assay buffer was: 10 mM TES, 50 mM KCl, 20 mM $Na_2MoO_4.2H_2O$, 1.5 mM EDTA, 0.04% w/v CHAPS, 10% v/v glycerol, 1 mM dithiothreitol, pH 7.4. Test compounds were dissolved to 1 mM in neat DMSO and then further diluted to 10× assay concentration in assay buffer supplemented with 10% v/v DMSO. Test compounds were serially diluted at 10× assay concentrations in 10% DMSO-containing buffer in 96-well polypropylene plates. Binding reaction mixtures were prepared in 96-well black Dynex microtiter plates by sequential addition of the following assay components to each well: 15 μL of 10× test compound solution, 85 μL of GR-containing baculovirus lysate diluted 1:170 in assay buffer, and 50 μL of 15 nM TAMRA-labeled dexamethasone. Positive controls were reaction mixtures containing no test compound; negative controls (blanks) were reaction mixtures containing 0.7 μM to 2 μM dexamethasone. The binding reactions were incubated for 1 hour at room temperature and then read for fluorescence polarization in the LJL Analyst set to 550 nm excitation and 580 nm emission, with the Rhodamine 561 dichroic mirror installed. $IC_{50}$ values were determined by iterative non-linear curve fitting of the FP signal data to a 4-parameter logistic equation.

Compounds found to bind to the glucocorticoid receptor may be evaluated for binding to the progesterone receptor (PR), estrogen receptor (ER), and mineralocorticoid receptors to evaluate the compound's selectivity for GR. The protocols for PR and MR are identical to the above GR method, with the following exceptions: PR insect cell lysate is diluted 1:7.1 and MR lysate diluted 1:9.4. PR probe is TAMRA-labeled mifepristone, used at a final concentration of 5 nM in the assay, and the negative controls (blanks) were reactions containing mifepristone at 0.7 μM to 2 μM.

The ER protocol is similar to the above protocols, but uses PanVera kit receptor, fluorescein-labeled probe. The assay components are made in the same volumes as above, to produce final assay concentrations for ER of 15 nM and ES2 probe of 1 nM. In addition, the component order of addition is modified from the above assays: probe is added to the plate first, followed by receptor and test compound. The plates are read in the LJL Analyst set to 485 nm excitation and 530 nm emission, with the Fluorescein 505 dichroic mirror installed.

Compounds found to bind to the glucocorticoid receptor may be evaluated for dissociation of transactivation and transrepression by assays cited in the Background of the Invention (C. M. Bamberger and H. M. Schulte, Eur. J. Clin. Invest., 2000, 30 (suppl. 3) 6–9) or by the assays described below.

B. Glucocorticoid Receptor Cell Assays

1. Induction of Aromatase in Fibroblasts (Cell Assay for Transactivation)

Dexamethasone, a synthetic ligand to the glucocorticoid receptor (GR), induces expression of aromatase in human foreskin fibroblast cells. The activity of aromatase is measured by the conversion of testosterone to estradiol in culture media. Compounds that exhibit binding to GR are evaluated for their ability to induce aromatase activity in human foreskin fibroblasts.

Human foreskin fibroblast cells (ATCC Cat. No. CRL-2429, designation CCD112SK) are plated on 96 well plates at 50,000 cells per well 5 days before use, in Iscove's Modified Dulbecco's Media (GibcoBRL Life Technologies Cat No. 12440-053) supplemented with 10% charcoal filtered FBS (Clonetech Cat No. SH30068) and Gentamycin (GibcoBRL Life Technologies Cat. No. 15710-064). On the day of the experiment, the media in the wells is replaced with fresh media. Cells are treated with test compounds to final concentrations of $10^{-5}$ M to $10^{-8}$ M, and testosterone to a final concentration of 300 ng/mL. Each well has a total volume of 100 µL. Samples are made in duplicates. Control wells include: (a) wells that receive testosterone only, and (b) wells that receive testosterone plus 2 µM of dexamethasone to provide maximum induction of aromatase. Plates are incubated at 37° C. overnight (15 to 18 hours), and supernatants are harvested at the end of incubation. Estradiol in the supernatant is measured using ELISA kits for estradiol (made by ALPCO, obtained from American Laboratory Products Cat. No. 020-DR-2693) according to the manufacture's instruction. The amount of estradiol is inversely proportional to the ELISA signals in each well. The extent of aromatase induction by test compounds is expressed as a relative percentage to dexamethasone. $EC_{50}$ values of test compounds are derived by non-linear curve fitting.

2. Inhibition of IL-6 Production in Fibroblasts (Cell Assay for Transrepression)

Human foreskin fibroblast cells produce IL-6 in response to stimulation by pro-inflammatory cytokine IL-1. This inflammatory response, as measured by the production of IL-6, can be effectively inhibited by dexamethasone, a synthetic ligand to the glucocorticoid receptor (GR). Compounds that exhibit binding to GR are evaluated for their ability to inhibit IL-6 production in human foreskin fibroblasts.

Human foreskin fibroblast cells (ATCC Cat. No. CRL-2429) are plated on 96 well plates at 5,000 cells per well the day before use, in Iscove's Modified Dulbecco's Media (GibcoBRL Life Technologies Cat. No. 12440-053) supplemented with 10% charcoal filtered FBS (Clonetech Cat. No. SH30068) and Gentamycin (GibcoBRL Life Technologies Cat. No. 15710-064). On the next day, media in the wells is replaced with fresh media. Cells are treated with IL-1 (rhIL-1α, R&D Systems Cat. No. 200-LA) to a final concentration of 1 ng/mL, and with test compounds to final concentrations of $10^{-5}$ M to $10^{-8}$ M, in a total volume of 200 µL per well. Samples are done in duplicates. Background control wells do not receive test compounds or IL-1. Positive control wells receive IL-1 only and represent maximum (or 100%) amount of IL-6 production. Plates are incubated at 37° C. overnight (15 to 18 hours), and supernatants are harvested at the end of incubation. IL-6 levels in the supernatants are determined by the ELISA kits for IL-6 (MedSystems Diagnostics GmbH, Vienna, Austria, Cat. No. BMS213TEN) according to manufacture's instructions. The extent of inhibition of IL-6 by test compounds is expressed in percentage relative to positive controls. $IC_{50}$ values of test compounds are derived by non-linear curve fitting.

Evaluation of agonist or antagonist activity of compounds binding to the glucocorticoid receptor may be determined by any of the assays.

3. Modulation of Tyrosine Aminotransferase (TAT) Induction in Rat Hepatoma Cells Testing of compounds for agonist or antagonist activity in induction of tyrosine aminotransferase (TAT) in rat hepatoma cells.

H4-II-E-$C_3$ cells were incubated overnight in 96 well plates (20,000 cells/100 µL/well) in MEM medium containing 10% heat inactivated FBS and 1% nonessential amino acids. On the next day, cells were stimulated with the indicated concentrations of dexamethasone or test compound (dissolved in DMSO, final DMSO concentration 0.2%) for 18 hours. Control cells were treated with 0.2% DMSO. After 18 hours, the cells were lysed in a buffer containing 0.1% Triton X-100 and the TAT activity was measured in a photometric assay using tyrosine and alpha-ketoglutarate as substrates.

For measuring antagonist activity, the hepatoma cells were pre-stimulated by addition of dexamethasone (concentration ranges from $3\times10^{-9}$ M to $3\times10^{-8}$ M) shortly before the test compound was applied to the cells. The steroidal non-selective GR/PR antagonist mifepristone was used as control.

4. Modulation of MMTV-Luc Induction in HeLa Cells

Testing of compounds for agonist or antagonist activity in stimulation of MMTV-(mouse mammary tumor virus) promoter in HeLa cells.

HeLa cells were stably co-transfected with the pHHLuc-plasmid containing a fragment of the MMTV-LTR (−200 to +100 relative to the transcription start site) cloned in front of the luciferase gene (Norden, 1988) and the pcDNA3.1 plasmid (Invitrogen) constitutively expressing the resistance for the selective antibiotic GENETICIN®. Clones with best induction of the MMTV-promoter were selected and used for further experiments.

Cells were cultured overnight in DMEM medium without phenol red, supplemented with 3% CCS (charcoal treated calf serum) and then transferred to 96 well plates (15,000 cells/100 µL/well). On the next day, activation of the MMTV-promoter was stimulated by addition of test compound or dexamethasone dissolved in DMSO (final concentration 0.2%). Control cells were treated with DMSO only. After 18 hours, the cells were lysed with cell lysis reagent (Promega, Cat. No. E1531), luciferase assay reagent (Promega, Cat. No. E1501) was added and the glow luminescence was measured using a luminometer (BMG, Offenburg).

For measuring antagonist activity, the MMTV-promoter was pre-stimulated by adding dexamethasone ($3\times10^{-9}$ M to $3\times10^{-8}$ M) shortly before the test compound was applied to the cells. The steroidal non-selective GR/PR antagonist mifepristone was used as control.

5. Modulation of IL-8 Production in U937 Cells

Testing of compounds for agonist or antagonist activity in GR-mediated inhibition of LPS-induced IL-8 secretion in U-937 cells.

U-937 cells were incubated for 2 to 4 days in RPMI1640 medium containing 10% CCS (charcoal treated calf serum). The cells were transferred to 96 well plates (40,000 cells/100 µL/well) and stimulated with 1 µg/mL LPS (dissolved in PBS) in the presence or absence of dexamethasone or test compound (dissolved in DMSO, final concentration 0.2%). Control cells were treated with 0.2% DMSO. After 18 hours, the IL-8 concentration in the cell supernatant was measured by ELISA, using the "OptEIA human IL-8 set" (Pharmingen, Cat. No. 2654KI).

For measuring antagonist activity, the LPS-induced IL-8 secretion was inhibited by adding dexamethasone ($3\times10^{-9}$ M to $3\times10^{-8}$ M) shortly before the test compound was applied to the cells. The steroidal non-selective GR/PR antagonist mifepristone was used as control.

6. Modulation of ICAM-Luc Expression in HeLa Cells

Testing of compounds for agonist or antagonist activity in inhibition of TNF-alpha-induced activation of the ICAM-promoter in HeLa cells.

HeLa cells were stably co-transfected with a plasmid containing a 1.3 kb fragment of the human ICAM-promoter (−1353 to −9 relative to the transcription start site, Ledebur and Parks, 1995) cloned in front of the luciferase gene and the pcDNA3.1 plasmid (Invitrogen) which constitutively expresses the resistance for the antibiotic GENETICIN®. Clones with best induction of the ICAM-promoter were selected and used for further experiments. Cells were transferred to 96 well plates (15,000 cells/100 μL/well) in DMEM medium supplemented with 3% CCS. On the following day the activation of the ICAM-promoter was induced by addition of 10 ng/mL recombinant TNF-alpha (R&D System, Cat. No. 210-TA). Simultaneously the cells were treated with the test compound or dexamethasone (dissolved in DMSO, final concentration 0.2%). Control cells were treated with DMSO only. After 18 hours, the cells were lysed with cell lysis reagent (Promega, Cat. No. E1531), luciferase assay reagent (Promega, Cat. No. E1501) was added and glow luminescence was measured using a luminometer (BMG, Offenburg).

For measuring antagonist activity, the TNF-alpha-induced activation of the ICAM-promoter was inhibited by adding dexamethasone ($3 \times 10^{-9}$ M to $3 \times 10^{-8}$ M) shortly before the test compound was applied to the cells. The steroidal nonselective GR/PR antagonist mifepristone was used as control.

In general, the preferred potency range in the above assays is between 0.1 nM and 10 μM, the more preferred potency range is 0.1 nM to 1 μM, and the most preferred potency range is 0.1 nM to 100 nM.

Representative compounds of the invention have been tested and have shown activity as modulators of the glucocorticoid receptor function in one or more of the above assays. For example, the following compounds of the invention have demonstrated potent activity in the GR binding assay:

2-Benzyl-2-hydroxy-4-methyl-4-phenylpentanoic acid (1-oxo-1,3-dihydroisobenzofuran-5-yl)amide;

2-Cyclohexylmethyl-2-hydroxy-4-methyl-4-phenylpentanoic acid (1-oxo-1,3-dihydroisobenzofuran-5-yl)amide;

2-Hydroxy-4-methyl-2-(2-methyl-2-phenylpropyl)-4-phenylpentanoic acid (1-oxo-1,3-dihydroisobenzofuran-5-yl)amide;

2-Benzyl-4-(5-fluoro-2-methoxyphenyl)-2-hydroxy-4-methylpentanoic acid (1-oxo-1,3-dihydroisobenzofuran-5-yl)amide;

2-Cyclohexylmethyl-4-(5-fluoro-2-methoxyphenyl)-2-hydroxy-4-methylpentanoic acid (1-oxo-1,3-dihydroisobenzofuran-5-yl)amide;

2-Cyclohexylmethyl-4-(5-fluoro-2-hydroxyphenyl)-2-hydroxy-4-methylpentanoic acid (1-oxo-1,3-dihydroisobenzofuran-5-yl)amide;

2-(3-Fluorobenzyl)-4-(5-fluoro-2-methoxyphenyl)-2-hydroxy-4-methylpentanoic acid (1-oxo-1,3-dihydroisobenzofuran-5-yl)amide;

2-(2-Fluorobenzyl)-4-(5-fluoro-2-methoxyphenyl)-2-hydroxy-4-methylpentanoic acid (1-oxo-1,3-dihydroisobenzofuran-5-yl)amide;

2-(2-Fluorobenzyl)-4-(5-fluoro-2-hydroxyphenyl)-2-hydroxy-4-methylpentanoic acid (1-oxo-1,3-dihydroisobenzofuran-5-yl)amide;

2-(3,4-Difluorobenzyl)-4-(5-fluoro-2-hydroxyphenyl)-2-hydroxy-4-methylpentanoic acid (1-oxo-1,3-dihydroisobenzofuran-5-yl)amide;

2-(4-Fluorobenzyl)-4-(5-fluoro-2-hydroxyphenyl)-2-hydroxy-4-methylpentanoic acid (1-oxo-1,3-dihydroisobenzofuran-5-yl)amide;

2-Benzyl-4-(5-fluoro-2-methoxyphenyl)-2-hydroxy-4-methylpentanoic acid (4-methyl-1-oxo-1H-benzo[d][1,2]oxazin-6-yl)amide;

2-Benzyl-4-(5-fluoro-2-hydroxyphenyl)-2-hydroxy-4-methylpentanoic acid (4-methyl-1-oxo-1H-benzo[d][1,2]oxazin-6-yl)amide;

2-Cyclohexylmethyl-4-(5-fluoro-2-methoxyphenyl)-2-hydroxy-4-methylpentanoic acid (4-methyl-1-oxo-1H-benzo[d][1,2]oxazin-6-yl)amide;

4-(5-Fluoro-2-methoxyphenyl)-2-hydroxy-4-methyl-2-(2-methylbenzyl)pentanoic acid (1-oxo-1,3-dihydroisobenzofuran-5-yl)amide;

4-(5-Fluoro-2-hydroxyphenyl)-2-hydroxy-4-methyl-2-(2-methylbenzyl)pentanoic acid (1-oxo-1,3-dihydroisobenzofuran-5-yl)amide;

2-Cyclohexylmethyl-4-(5-fluoro-2-hydroxyphenyl)-2-hydroxy-4-methylpentanoic acid (4-methyl-1-oxo-1H-benzo[d][1,2]oxazin-6-yl)amide;

2-(2-Chlorobenzyl)-4-(5-fluoro-2-methoxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-4-methyl-2-phenethylpentanoic acid (1-oxo-1,3-dihydroisobenzofuran-5-yl)amide;

2-(2-Chlorobenzyl)-4-(5-fluoro-2-hydroxyphenyl)-2-hydroxy-4-methylpentanoic acid (1-oxo-1,3-dihydroisobenzofuran-5-yl)amide;

4-(5-Fluoro-2-hydroxyphenyl)-2-hydroxy-2-(2-hydroxybenzyl)-4-methylpentanoic acid (1-oxo-1,3-dihydroisobenzofuran-5-yl)amide;

2-(2-Bromobenzyl)-4-(5-fluoro-2-methoxyphenyl)-2-hydroxy-4-methylpentanoic acid (1-oxo-1,3-dihydroisobenzofuran-5-yl)amide;

2-(2-Bromobenzyl)-4-(5-fluoro-2-hydroxyphenyl)-2-hydroxy-4-methylpentanoic acid (1-oxo-1,3-dihydroisobenzofuran-5-yl)amide;

5-[2-Benzyl-4-(5-fluoro-2-methoxyphenyl)-2-hydroxy-4-methylpentylamino]-3H-isobenzofuran-1-one;

4-(5-Fluoro-2-hydroxyphenyl)-2-hydroxy-4-methyl-2-(1-phenylethyl)pentanoic acid (1-oxo-1,3-dihydroisobenzofuran-5-yl)amide;

2-Benzyl-2-hydroxy-4-methyl-4-phenylpentanoic acid (4-methyl-1-oxo-1H-benzo[d][1,2]oxazin-6-yl)amide;

2-Cyclohexylmethyl-2-hydroxy-4-methyl-4-phenylpentanoic acid (4-methyl-1-oxo-1H-benzo[d][1,2]oxazin-6-yl)amide;

2-Cyclopentyl-4-(5-fluoro-2-hydroxyphenyl)-2-hydroxy-4-methylpentanoic acid (1-oxo-1,3-dihydroisobenzofuran-5-yl)amide; and 2-Cyclopentylmethyl-4-(5-fluoro-2-hydroxyphenyl)-2-hydroxy-4-methylpentanoic acid (1-oxo-1,3-dihydroisobenzofuran-5-yl)amide.

In addition, the following compounds of the invention have been tested and have shown activity as antagonists of the glucocorticoid receptor function in one or more of the above assays:

2-Benzyl-2-hydroxy-4-methyl-4-phenylpentanoic acid (1-oxo-1,3-dihydroisobenzofuran-5-yl)amide; and 2-Cyclohexylmethyl-2-hydroxy-4-methyl-4-phenylpentanoic acid (1-oxo-1,3-dihydroisobenzofuran-5-yl)amide.

The invention also provides methods of modulating the glucocorticoid receptor function in a patient comprising administering to the patient a compound according to the invention. If the purpose of modulating the glucocorticoid receptor function in a patient is to treat a disease-state or condition, the administration preferably comprises a therapeutically or pharmaceutically effective amount of a pharmaceutically acceptable compound according to the invention. If the purpose of modulating the glucocorticoid receptor function in a patient is for a diagnostic or other purpose (e.g., to determine the patient's suitability for therapy or sensitivity to various sub-therapeutic doses of the compounds according to the invention), the administration preferably comprises an effective amount of a compound according to the invention, that is, the amount necessary to obtain the desired effect or degree of modulation.

Methods of Therapeutic Use

As pointed out above, the compounds of the invention are useful in modulating the glucocorticoid receptor function. In doing so, these compounds have therapeutic use in treating disease-states and conditions mediated by the glucocorticoid receptor function or that would benefit from modulation of the glucocorticoid receptor function.

As the compounds of the invention modulate the glucocorticoid receptor function, they have very useful anti-inflammatory and antiallergic, immune-suppressive, and anti-proliferative activity and they can be used in patients as drugs, particularly in the form of pharmaceutical compositions as set forth below, for the treatment of disease-states and conditions.

The agonist compounds according to the invention can be used in patients as drugs for the treatment of the following disease-states or indications that are accompanied by inflammatory, allergic, and/or proliferative processes:

(i) Lung diseases: chronic, obstructive lung diseases of any genesis, particularly bronchial asthma and chronic obstructive pulmonary disease (COPD); adult respiratory distress syndrome (ARDS); bronchiectasis; bronchitis of various genesis; all forms of restrictive lung diseases, particularly allergic alveolitis; all forms of lung edema, particularly toxic lung edema; all forms of interstitial lung diseases of any genesis, e.g., radiation pneumonitis; and sarcoidosis and granulomatoses, particularly Boeck disease;

(ii) Rheumatic diseases or autoimmune diseases or joint diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); traumatic arthritis; collagenoses of any genesis, e.g., systemic lupus erythematosus, scleroderma, polymyositis, dermatomyositis, Sjögren syndrome, Still disease, and Felty syndrome;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vasculitis diseases: panarteritis nodosa, polyarteritis nodosa, arteritis temporalis, Wegner granulomatosis, giant cell arthritis, and erythema nodosum;

(v) Dermatological diseases: atopic dermatitis, particularly in children; psoriasis; pityriasis rubra pilaris; erythematous diseases triggered by various noxa, e.g., rays, chemicals, burns, etc.; bullous dermatoses; diseases of the lichenoid complex; pruritus (e.g., of allergic genesis); seborrheic dermatitis; rosacea; pemphigus vulgaris; erythema multiforme exudativum; balanitis; vulvitis; hair loss, such as occurs in alopecia areata; and cutaneous T cell lymphomas;

(vi) Renal diseases: nephrotic syndrome; and all types of nephritis, e.g., glomerulonephritis;

(vii) Hepatic diseases: acute liver cell disintegration; acute hepatitis of various genesis, e.g., viral, toxic, drug-induced; and chronically aggressive and/or chronically intermittent hepatitis;

(viii) Gastrointestinal diseases: inflammatory bowel diseases, e.g., regional enteritis (Crohn disease), colitis ulcerosa; gastritis; peptic esophagitis (refluxoesophagitis); and gastroenteritis of other genesis, e.g., nontropical sprue;

(ix) Proctological diseases: anal eczema; fissures; hemorrhoids; and idiopathic proctitis;

(x) Eye diseases: allergic keratitis, uveitis, or iritis; conjunctivitis; blepharitis; neuritis nervi optici; choroiditis; and sympathetic ophthalmia;

(xi) Diseases of the ear, nose, and throat (ENT) area: allergic rhinitis or hay fever; otitis externa, e.g., caused by contact eczema, infection, etc.; and otitis media;

(xii) Neurological diseases: brain edema, particularly tumor-related brain edema; multiple sclerosis; acute encephalomyelitis; meningitis; acute spinal cord injury; stroke; and various forms of seizures, e.g., nodding spasms;

(xiii) Blood diseases: acquired hemolytic anemia; and idiopathic thrombocytopenia;

(xiv) Tumor diseases: acute lymphatic leukemia; malignant lymphoma; lymphogranulomatoses; lymphosarcoma; extensive metastases, particularly in mammary, bronchial, and prostatic carcinoma;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Grave disease;

(xvi) Organ and tissue transplantations and graft-versus-host diseases;

(xvii) Severe states of shock, e.g., septic shock, anaphylactic shock, and systemic inflammatory response syndrome (SIRS);

(xviii) Substitution therapy in: congenital primary adrenal insufficiency, e.g., adrenogenital syndrome; acquired primary adrenal insufficiency, e.g., Addison disease, autoimmune adrenalitis, post-infection, tumors, metastases, etc.; congenital secondary adrenal insufficiency, e.g., congenital hypopituitarism; and acquired secondary adrenal insufficiency, e.g., post-infection, tumors, metastases, etc.;

(xix) Pain of inflammatory genesis, e.g., lumbago; and (xx) various other disease-states or conditions including type I diabetes (insulin-dependent diabetes), osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis and syndromes associated with hemodialysis, leukopheresis, and granulocyte transfusion.

In addition, the compounds according to the invention can be used for the treatment of any other disease-states or conditions not mentioned above which have been treated, are treated, or will be treated with synthetic glucocorticoids (see, e.g., H. J. Hatz, *Glucocorticoide: Immunologische Grundlagen, Pharmakologie und Therapierichtlinien* [Glucocorticoids: Immunological Fundamentals, Pharmacology, and Therapeutic Guidelines], Stuttgart: Verlagsgesellschaft mbH, 1998, which is hereby incorporated by reference in its entirety). Most or all of the indications (i)

through (xx) mentioned above are described in detail in H. J. Hatz, *Glucocorticoide: Immunologische Grundiagen Pharmakologie und Therapierichtlinien*. Furthermore, the compounds of the invention can also be used to treat disorders other than those listed above or mentioned or discussed herein, including in the Background of the Invention.

The antagonist compounds according to the invention, whether full antagonists or partial antagonists, can be used in patients as drugs for the treatment of the following disease-states or indications, without limitation: type II diabetes (non-insulin-dependent diabetes); obesity; cardiovascular diseases; hypertension; arteriosclerosis; neurological diseases, such as psychosis and depression; adrenal and pituitary tumors; glaucoma; and Cushing syndrome based on an ACTH-secreting tumor like pituitary adenoma. In particular, the compounds of the invention are useful for treating obesity and all disease-states and indications related to a deregulated fatty acids metabolism such as hypertension, atherosclerosis, and other cardiovascular diseases. Using the compounds of the invention that are GR antagonists, it should be possible to antagonize both the carbohydrate metabolism and fatty acids metabolism. Thus, the antagonist compounds of the invention are useful in treating all disease-states and conditions that involve increased carbohydrate, protein, and lipid metabolism and would include disease-states and conditions leading to catabolism like muscle frailty (as an example of protein metabolism).

Methods of Diagnostic Use

The compounds of the invention may also be used in diagnostic applications and for commercial and other purposes as standards in competitive binding assays. In such uses, the compounds of the invention may be used in the form of the compounds themselves or they may be modified by attaching a radioisotope, luminescence, fluorescent label or the like in order to obtain a radioisotope, luminescence, or fluorescent probe, as would be known by one of skill in the art and as outlined in *Handbook of Fluorescent Probes and Research Chemicals*, 6th Edition, R. P. Haugland (ed.), Eugene: Molecular Probes, 1996; *Fluorescence and Luminescence Probes for Biological Activity*, W. T. Mason (ed.), San Diego: Academic Press, 1993; *Receptor-Ligand Interaction, A Practical Approach*, E. C. Hulme (ed.), Oxford: IRL Press, 1992, each of which is hereby incorporated by reference in their entireties.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sublingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Generally, a therapeutically effective daily dose is from about 0.001 mg to about 15 mg/kg of body weight per day of a compound of the invention; preferably, from about 0.1 mg to about 10 mg/kg of body weight per day; and most preferably, from about 0.1 mg to about 1.5 mg/kg of body weight per day. For example, for administration to a 70 kg person, the dosage range would be from about 0.07 mg to about 1050 mg per day of a compound of the invention, preferably from about 7.0 mg to about 700 mg per day; and most preferably from about 7.0 mg to about 105 mg per day. Some degree of routine dose optimization may be required to determine an optimal dosing level and pattern.

Pharmaceutically acceptable carriers and excipients encompass all the foregoing additives and the like.

EXAMPLES OF PHARMACEUTICAL FORMULATIONS

| A. TABLETS | |
| --- | --- |
| Component | Amount per tablet (mg) |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
|---|---|
| active substance | 80 |
| Lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
|---|---|
| active substance | 5 |
| Lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
|---|---|
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
|---|---|
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
|---|---|
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
|---|---|
| active substance | 0.005 |
| sorbitan trioleate | 0.1 |
| monofluorotrichloromethane and difluorodichloromethane (2:3) | to 100 |

The suspension is transferred into a conventional aerosol container with a metering valve. Preferably, 50 μL of suspension are delivered per spray. The active substance may also be metered in higher doses if desired (e.g., 0.02% by weight).

| Component | Amount |
|---|---|
| H. POWDER FOR INHALATION | |
| active substance | 1.0 mg |
| lactose monohydrate | to 25 mg |
| I. POWDER FOR INHALATION | |
| active substance | 2.0 mg |
| lactose monohydrate | to 25 mg |
| J. POWDER FOR INHALATION | |
| active substance | 1.0 mg |
| lactose monohydrate | to 5 mg |
| K. POWDER FOR INHALATION | |
| active substance | 2.0 mg |
| lactose monohydrate | to 5 mg |

We claim:

1. A compound of Formula (I)

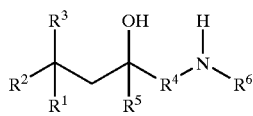

wherein:

$R^1$ is an aryl or heteroaryl group, each optionally independently substituted with one to three substituent groups, wherein each substituent group of $R^1$ is independently $C_1$–$C_5$ alkyl, $C_2$–$C_5$ alkenyl, $C_2$–$C_5$ alkynyl, $C_3$–$C_8$ cycloalkyl, aryl, $C_1$–$C_5$ alkoxy, aryloxy, $C_1$–$C_5$ alkanoyl, aroyl, $C_1$–$C_5$ alkoxycarbonyl, $C_1$–$C_5$ alkanoyloxy, aminocarbonyloxy, $C_1$–$C_5$ alkylaminocarbonyloxy, aminocarbonyl, $C_1$–$C_5$ alkylaminocarbonyl, $C_1$–$C_5$ alkanoylamino, $C_1$–$C_5$ alkoxycarbonylamino, $C_1$–$C_5$ alkylsulfonylamino, $C_1$–$C_5$ alkylaminosulfonyl, halogen, hydroxy, carboxy, cyano, trifluoromethyl, nitro, amino wherein the nitrogen atom is optionally independently mono- or di-substituted by $C_1$–$C_5$ alkyl or aryl; or ureido wherein either nitrogen atom is optionally independently substituted with $C_1$–$C_5$ alkyl; or $C_1$–$C_5$ alkylthio wherein the sulfur atom is optionally oxidized to a sulfoxide or sulfone, wherein each substituent group of $R^1$ is optionally independently substituted with one to three substituent groups selected from methyl, halogen, hydroxy, oxo, cyano, trifluoromethyl, and amino;

$R^2$ and $R^3$ are each independently hydrogen or $C_1$–$C_5$ alkyl, or $R^2$ and $R^3$ together with the carbon atom they are commonly attached to form a $C_3$–$C_8$ spiro cycloalkyl ring;

$R^4$ is $CH_2$ or $C=O$;

$R^5$ is carbocycle, heterocyclyl, aryl, heteroaryl, carbocycle-$C_1$–$C_8$ alkyl, aryl-$C_1$–$C_8$ alkyl, aryl-$C_1$–$C_8$ haloalkyl, heterocyclyl-$C_1$–$C_8$ alkyl, heteroaryl-$C_1$–$C_8$ alkyl, carbocycle-$C_2$–$C_8$ alkenyl, aryl-$C_2$–$C_8$ alkenyl, heterocyclyl-$C_2$–$C_8$ alkenyl, or heteroaryl-$C_2$–$C_8$ alkenyl, each optionally independently substituted with one to three substituent groups, wherein each substituent group of $R^5$ is independently $C_1$–$C_5$ alkyl, $C_2$–$C_5$ alkenyl, $C_2$–$C_5$ alkynyl, $C_3$–$C_8$ cycloalkyl, phenyl, $C_1$–$C_5$ alkoxy, phenoxy, $C_1$–$C_5$ alkanoyl, aroyl, $C_1$–$C_5$ alkoxycarbonyl, $C_1$–$C_5$ alkanoyloxy, aminocarbonyloxy, $C_1$–$C_5$ alkylaminocarbonyloxy, aminocarbonyl, $C_1$–$C_5$ alkylaminocarbonyl, $C_1$–$C_5$ alkanoylamino, $C_1$–$C_5$ alkoxycarbonylamino, $C_1$–$C_5$ alkylsulfonylamino, $C_1$–$C_5$ alkylaminosulfonyl, halogen, hydroxy, carboxy, cyano, trifluoromethyl, nitro, amino wherein the nitrogen atom is optionally independently mono- or di-substituted by $C_1$–$C_5$ alkyl; or ureido wherein either nitrogen atom is optionally independently substituted with $C_1$–$C_5$ alkyl; or $C_1$–$C_5$ alkylthio wherein the sulfur atom is optionally oxidized to a sulfoxide or sulfone; and

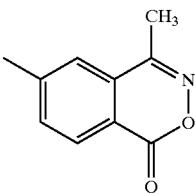

or a tautomer, prodrug, or salt thereof.

2. The compound of Formula (I) according to claim 1, wherein:

$R^1$ is phenyl, naphthyl, indanyl, indenyl, chromanyl, dihydrobenzofuranyl, dihydroindolyl, dihydroquinolinyl, dihydroisoquinolinyl, tetrahydroquinolinyl, tetrahydroisoquinolinyl, thienyl, furanyl, pyrrolyl, pyridinyl, pyrazinyl, pyrimidinyl, pyrazinyl, indolyl, benzofuranyl, or benzothienyl, each optionally independently substituted with one to three substituent groups, wherein each substituent group of $R^1$ is independently $C_1$–$C_3$ alkyl, $C_2$–$C_3$ alkenyl, $C_2$–$C_3$ alkynyl, $C_1$–$C_3$ alkoxy, $C_1$–$C_3$ alkanoyl, $C_1$–$C_3$ alkanoylamino, halogen, hydroxy, cyano, trifluoromethyl, or amino wherein the nitrogen atom is optionally independently mono- or di-substituted by $C_1$–$C_3$ alkyl; or $C_1$–$C_3$ alkylthio wherein the sulfur atom is optionally oxidized to a sulfoxide or sulfone, wherein each substituent group of $R^1$ is optionally independently substituted with one to three substituent groups selected from methyl, fluoro, chloro, bromo, hydroxy, oxo, cyano, trifluoromethyl, and amino;

$R^2$ and $R^3$ are each independently $C_1$–$C_3$ alkyl, or $R^2$ and $R^3$ together with the carbon atom they are commonly attached to form a $C_3$–$C_6$ spiro cycloalkyl ring;

$R^4$ is $CH_2$ or $C=O$; and $R^5$ is cyclopropyl, cyclobutyl, cyclopentyl, cyclohexyl, cyclopentylmethyl, cyclohexylmethyl, benzyl, cyclopentylethyl, cyclohexylethyl, phenethyl, or phenyl-difluoromethyl, each optionally independently substituted with one to three substituent groups, wherein each substituent group of $R^5$ is independently methyl, methoxy, hydroxy, halogen, cyano, or trifluoromethyl, or a tautomer, prodrug, or salt thereof.

3. The compound of Formula (I) according to claim 1, wherein $R^2$ and $R^3$ together with the carbon atom they are commonly attached to form a $C_3$–$C_8$ spiro cycloalkyl ring.

4. The compound of Formula (I) according to claim 1, wherein $R^2$ and $R^3$ are each independently hydrogen or $C_1$–$C_5$ alkyl.

5. The compound of Formula (I) according to claim 1, wherein $R^4$ is $CH_2$.

6. The compound of Formula (I) according to claim 1, wherein $R^4$ is $C=O$.

7. A compound selected from:

2-Benzyl-4-(5-fluoro-2-methoxyphenyl)-2-hydroxy-4-methylpentanoic acid (4-methyl-1-oxo-1-oxo-1H-benzo[d][1,2]oxazin-6-yl)amide;

2-Benzyl-4-(5-fluoro-2-hydroxyphenyl)-2-hydroxy-4-methylpentanoic acid (4-methyl-1-oxo-1H-benzo[d][1,2]oxazin-6-yl)amide;

2-Cyclohexylmethyl-4-(5-fluoro-2-methoxyphenyl)-2-hydroxy-4-methylpentanoic acid (4-methyl-1-oxo-1H-benzo[d][1,2]oxazin-6-yl)amide;

2-Cyclohexylmethyl-4-(5-fluoro-2-hydroxyphenyl)-2-hydroxy-4-methylpentanoic acid (4-methyl-1-oxo-1H-benzo[d][1,2]oxazin-6-yl)amide;

2-Benzyl-2-hydroxy-4-methyl-4-phenylpentanoic acid (4-methyl-1-oxo-1H-benzo[d][1,2]oxazin-6-yl)amide; and 2-Cyclohexylmethyl-2-hydroxy-4-methyl-4-phenylpentanoic acid (4-methyl-1-oxo-1H-benzo[d][1,2]oxazin-6-yl)amide, or the tautomers, prodrugs, solvates, or salts thereof.

8. A pharmaceutical composition comprising an effective amount of a compound according to one of claim 1 to 6 and 8 to 10, or a tautomer, prodrug, solvate, or salt thereof, and a pharmaceutically acceptable excipient or carrier.

9. A method of modulating the glucocorticoid receptor function in a patient, the method comprising administering to the patient an effective amount of a pharmaceutically acceptable compound according to one of claim 1 to 6 and 8 to 10, or a tautomer, prodrug, solvate, or salt thereof.

10. A method of treating a disease-state or condition mediated by the glucocorticoid receptor function in a patient in need of such treatment, the method comprising administering to the patient an effective amount of a pharmaceutically acceptable compound according to one of claim 1 to 6 or to 10, or a tautomer, prodrug, solvate, or salt thereof.

11. A method of treating a disease-state or condition selected from: type II diabetes, obesity, hypertension, arteriosclerosis, and glaucoma, in a patient in need of such treatment, the method comprising administering to the patient an effective amount of a pharmaceutically acceptable compound according to one of claim 1 to 6 or 8 to 10, or a tautomer, prodrug, solvate, or salt thereof.

12. A method of making a compound of Formula (I)

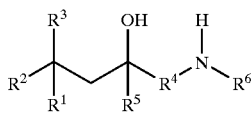

where $R^1$, $R^2$, $R^3$, $R^5$, and $R^6$ are as defined in claim 1 and $R^4$ is C=O, the method comprising:

(a) reacting a compound of Formula (II) with diethyl oxalate in a suitable solvent to form a ketoester of Formula (III)

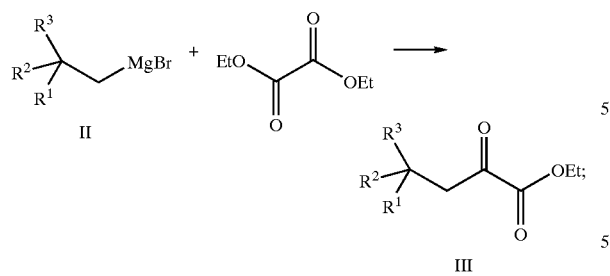

(b) hydrolyzing the ketoester of Formula (III) to form a carboxylic acid of Formula (IV)

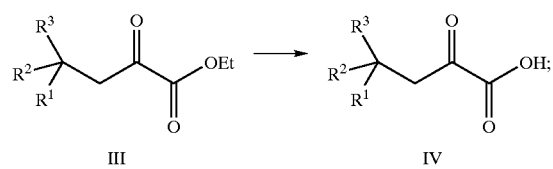

(c) coupling the carboxylic acid of Formula (IV) with an amine $R^6NH_2$ using suitable coupling conditions to form an amide of Formula (V)

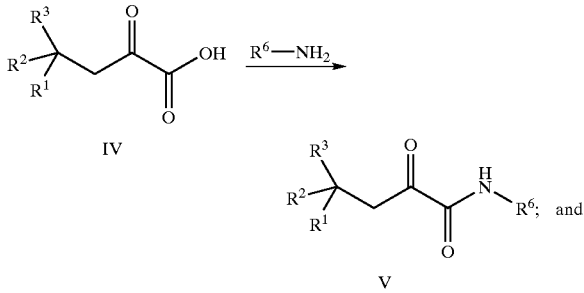

(d) reacting the amide of Formula (V) with $R^5M$ where M is Li or MgX, and X is Cl, Br, or I, in a suitable solvent to form the compound of Formula (I) where $R^4$ is C=O

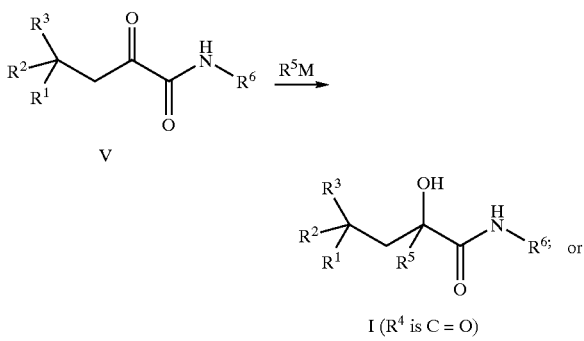

(a') reacting an aryl bromide $R^1Br$ with a suitable organometallic reagent in a suitable solvent and reacting the resulting anion with a ketone bearing $R^2$ and $R^3$ to give an alcohol of Formula (VI)

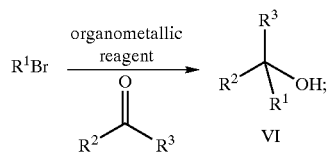

(b') reacting the alcohol of Formula (VI) with the trimethylsilyl enol ether derived from ethyl pyruvate, in the presence of a suitable Lewis acid, in a suitable solvent to provide a ketoester of Formula (III)

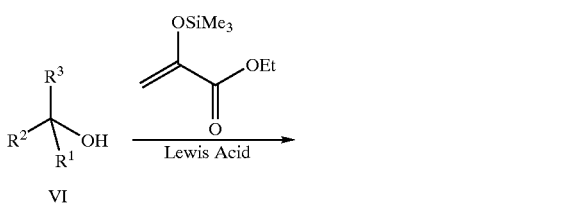

and performing steps (b), (c), and (d), as set forth above.

* * * * *